United States Patent [19]

Boden

[11] 4,390,462

[45] Jun. 28, 1983

[54] ALIPHATIC BRANCHED OLEFIN DIOXOLANES, DITHIOLANES, AND OXATHIOLANES AND USES THEREOF IN AUGMENTING OR ENHANCING THE AROMA AND/OR TASTE OF CONSUMABLE MATERIALS

[75] Inventor: Richard M. Boden, Monmouth Beach, N.J.

[73] Assignee: International Flavors & Fragrances Inc., New York, N.Y.

[21] Appl. No.: 322,726

[22] Filed: Nov. 19, 1981

Related U.S. Application Data

[63] Continuation-in-part of Ser. No. 212,993, Dec. 4, 1980, Pat. No. 4,315,952.

[51] Int. Cl.[3] .............. A61K 7/46
[52] U.S. Cl. .............. 252/522 R
[58] Field of Search .............. 252/522 R

[56] References Cited

U.S. PATENT DOCUMENTS

| | | | |
|---|---|---|---|
| 3,658,849 | 4/1972 | Leffingwell | 252/522 R X |
| 3,769,303 | 10/1973 | Easter, Jr. et al. | 252/522 R X |
| 3,863,013 | 1/1975 | Wilson et al. | 252/522 R X |
| 4,220,561 | 9/1980 | Winter | 252/522 R |

FOREIGN PATENT DOCUMENTS

| | | | |
|---|---|---|---|
| 2648109 | 4/1978 | Fed. Rep. of Germany | 252/522 R |
| 3004661 | 8/1981 | Fed. Rep. of Germany | 252/522 R |
| 7305488 | 10/1974 | Netherlands | 252/522 R |

OTHER PUBLICATIONS

Arctander, *Perfume and Flavor Chemicals*, Monograph No. 1402 (1969).
Kulka, CA 66: 37850r (1967).

*Primary Examiner*—Thomas A. Waltz
*Attorney, Agent, or Firm*—Arthur L. Liberman

[57] ABSTRACT

Described is the genus of compound having the structure:

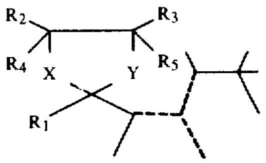

wherein $R_1$ represents $C_1$–$C_3$ lower alkyl, $R_2$, $R_3$, $R_4$ and $R_5$ represent the same or different hydrogen or $C_1$–$C_3$ lower alkyl; X and Y represent the same or different oxygen or sulfur; and one of the dashed lines represents a carbon-carbon double bond and the other of the dashed lines represent carbon-carbon single bonds as well as methods for augmenting or enhancing the aroma and/or taste of consumable materials including foodstuffs, chewing gums, medicinal products, toothpastes, chewing tobaccos, perfume compositions, perfumed articles, smoking tobaccos and smoking tobacco articles using such dioxolanes, oxathiolanes and dithiolanes. The perfumed articles include solid or liquid anionic, cationic, nonionic or zwitterionic detergents, fabric softener compositions, dryer-added fabric softener articles, hair preparations, deodorant compositions, as well as bleaching compositions containing the same.

5 Claims, 40 Drawing Figures

GLC PROFILE FOR EXAMPLE I.

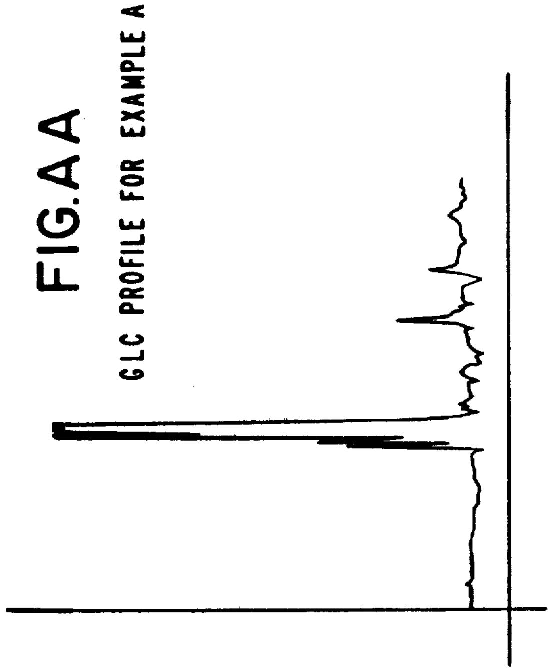
FIG. AA
GLC PROFILE FOR EXAMPLE A
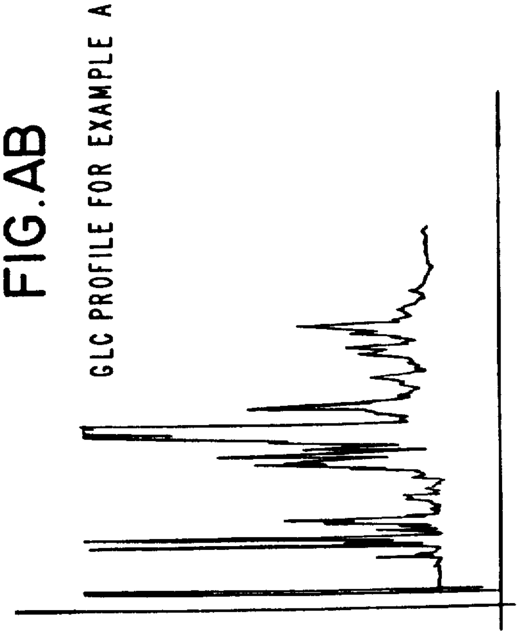
FIG. AB
GLC PROFILE FOR EXAMPLE A
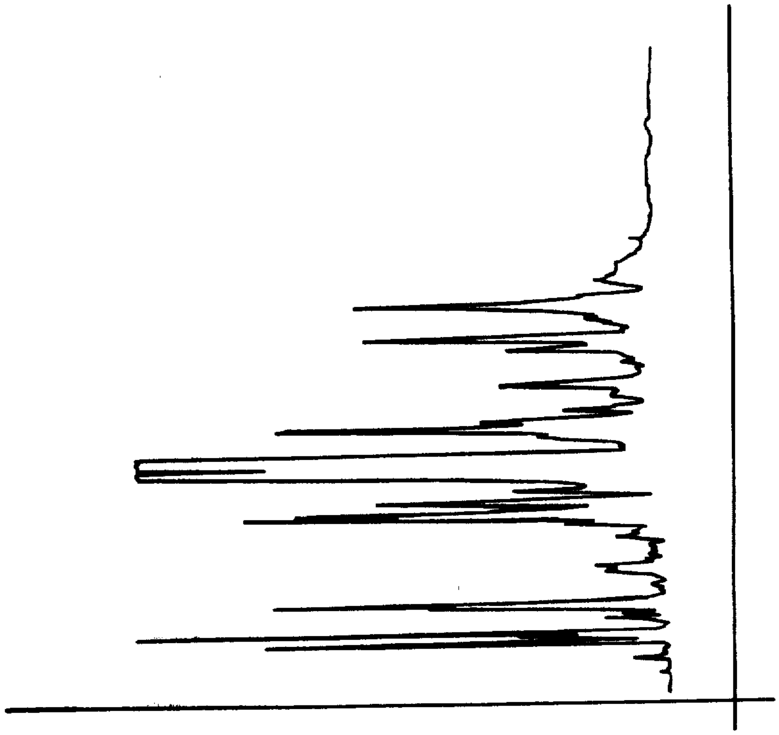
GLC PROFILE FOR EXAMPLE A.
FIG. AC FIG. AE
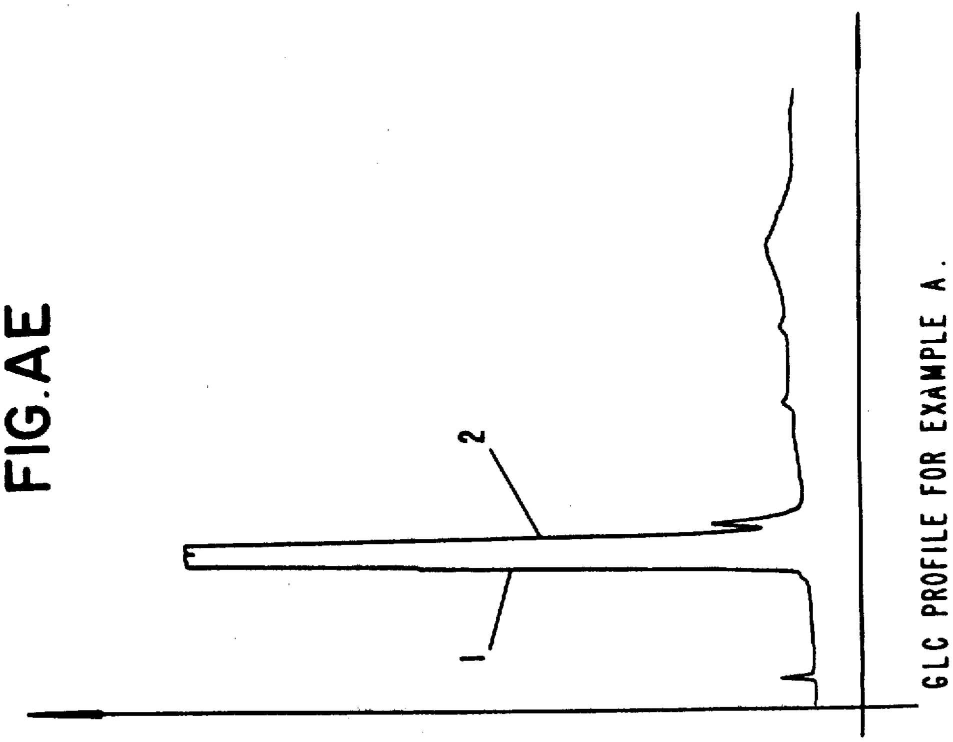
GLC PROFILE FOR EXAMPLE A. DISTILLATION PRODUCT
FIG. AD
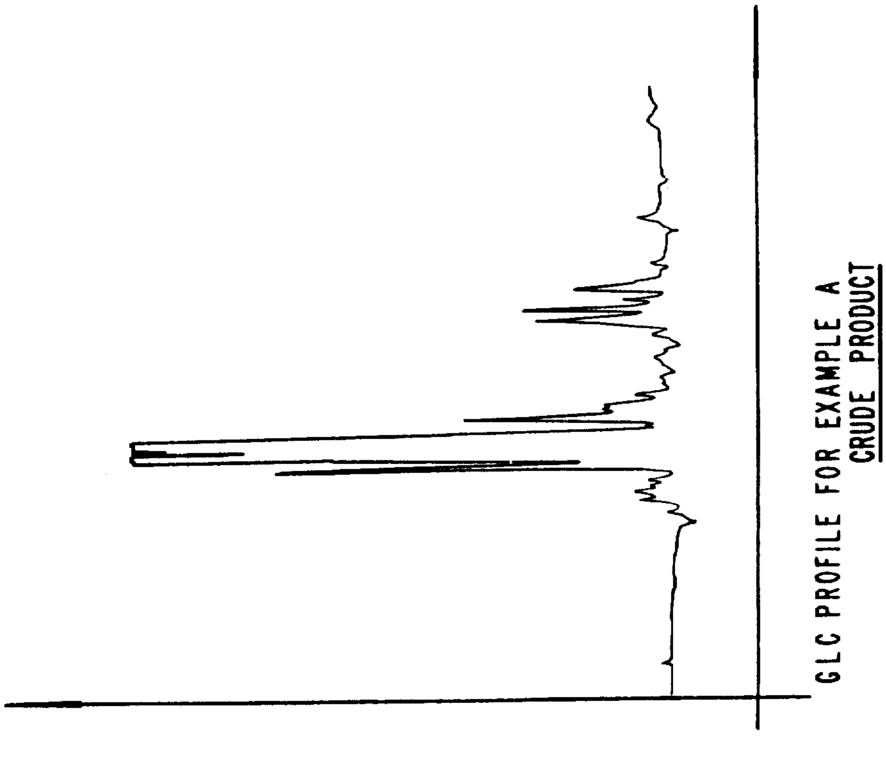
GLC PROFILE FOR EXAMPLE A CRUDE PRODUCT FIG.BA
NMR SPECTRUM FOR PEAK I OF EXAMPLE A, OF GLC OF FIG.AE
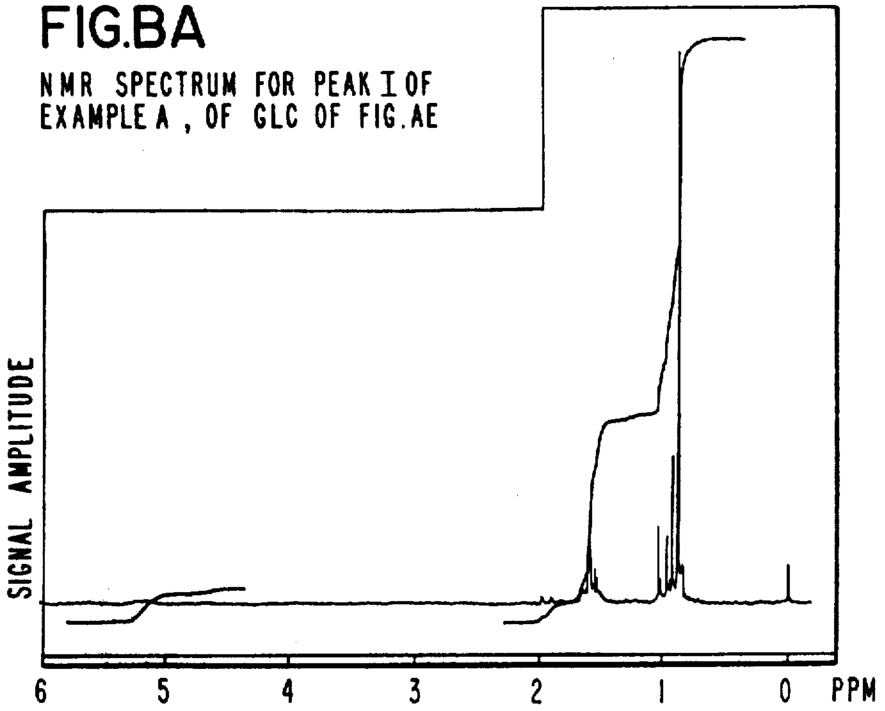
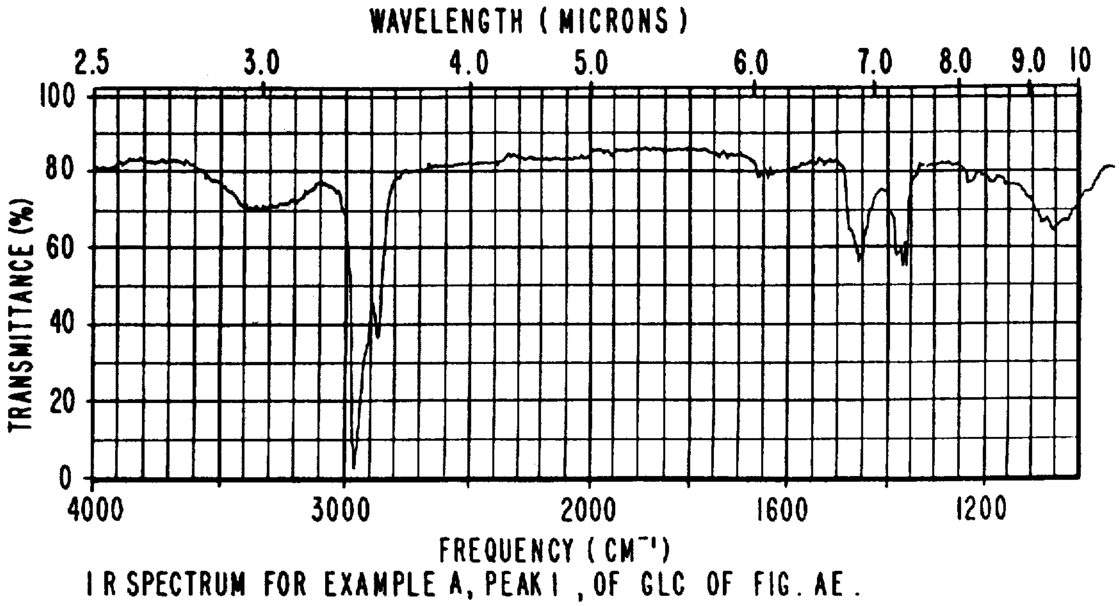
I R SPECTRUM FOR EXAMPLE A, PEAK I, OF GLC OF FIG. AE.
FIG.BB FIG.CA
NMR SPECTRUM FOR EXAMPLE A, PEAK 2, OF GLC OF FIG. AE
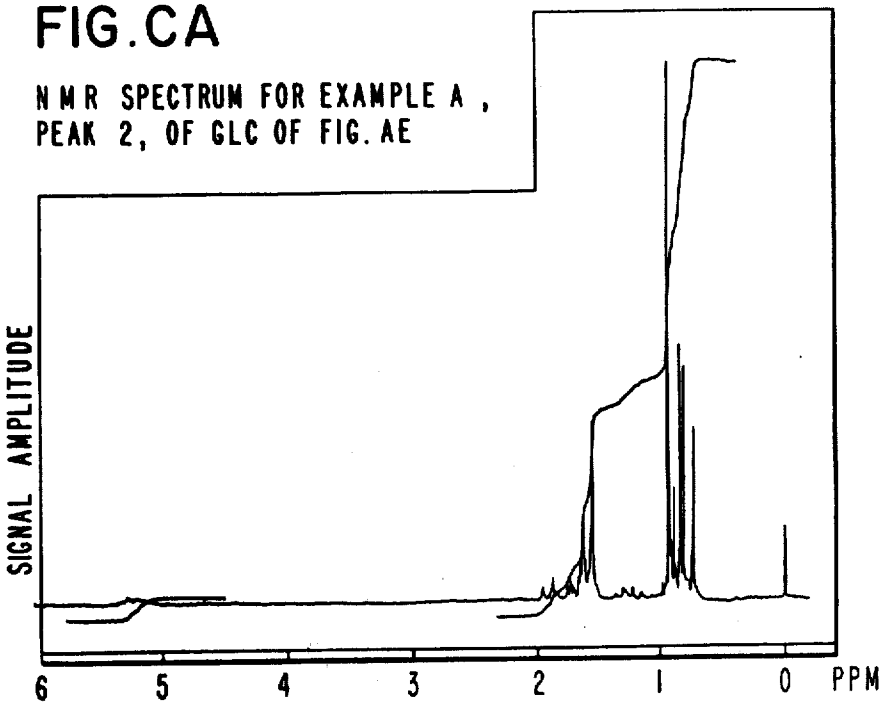
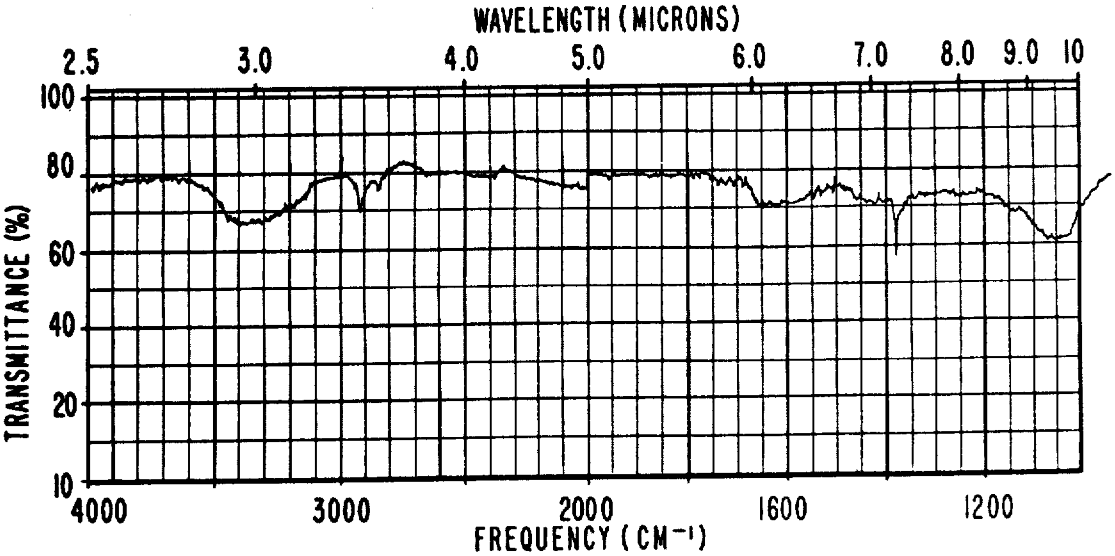
IR SPECTRUM FOR EXAMPLE I, PEAK 2 OF GLC OF FIG. AE
FIG.CB FIG. D
NMR SPECTRUM FOR PEAK 2 OF EXAMPLE I, OF GLC OF FIG. AB.
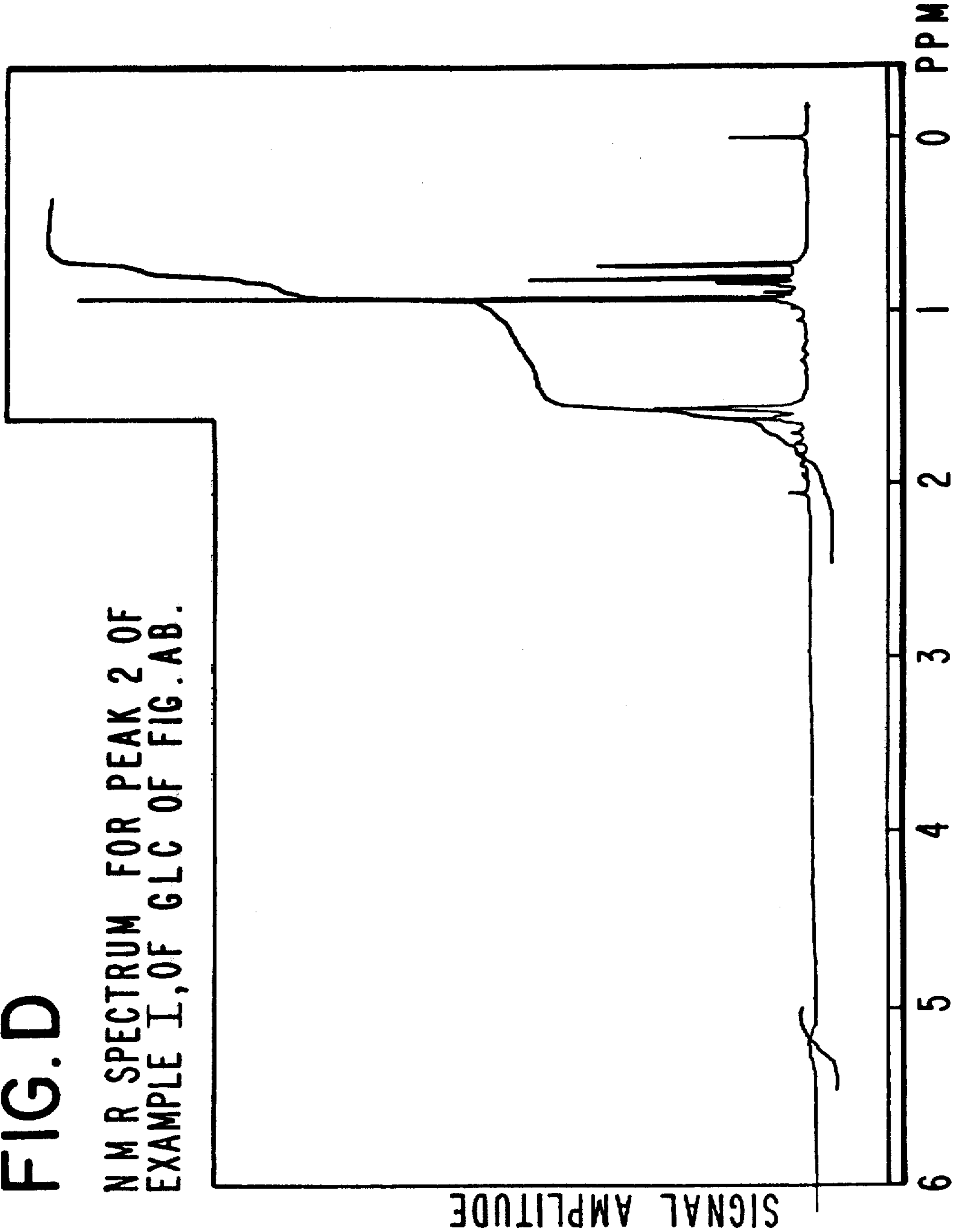

GLC PROFILE FOR EXAMPLE I.

IR SPECTRUM FOR PEAK 3 OF EXAMPLE I.

IR SPECTRUM FOR PEAK 4 OF EXAMPLE I

IR SPECTRUM FOR PEAK 5 OF EXAMPLE I

IR SPECTRUM FOR PEAK 6 OF EXAMPLE I.

IR SPECTRUM FOR PEAK 7 OF EXAMPLE I.

I R SPECTRUM FOR PEAK 8 OF EXAMPLE I.

I R SPECTRUM FOR PEAK 9 OF EXAMPLE I.

I R SPECTRUM FOR PEAK 10 OF EXAMPLE I.

NMR SPECTRUM FOR EXAMPLE I.

NMR SPECTRUM FOR EXAMPLE I.

NMR SPECTRUM FOR EXAMPLE I

GLC PROFILE FOR EXAMPLE II.

I R SPECTRUM FOR EXAMPLE II.

MASS SPECTRUM FOR EXAMPLE III.

GLC PROFILE FOR EXAMPLE IV.

MASS SPECTRUM FOR EXAMPLE II.

GLC PROFILE FOR EXAMPLE III.

FIG. 7
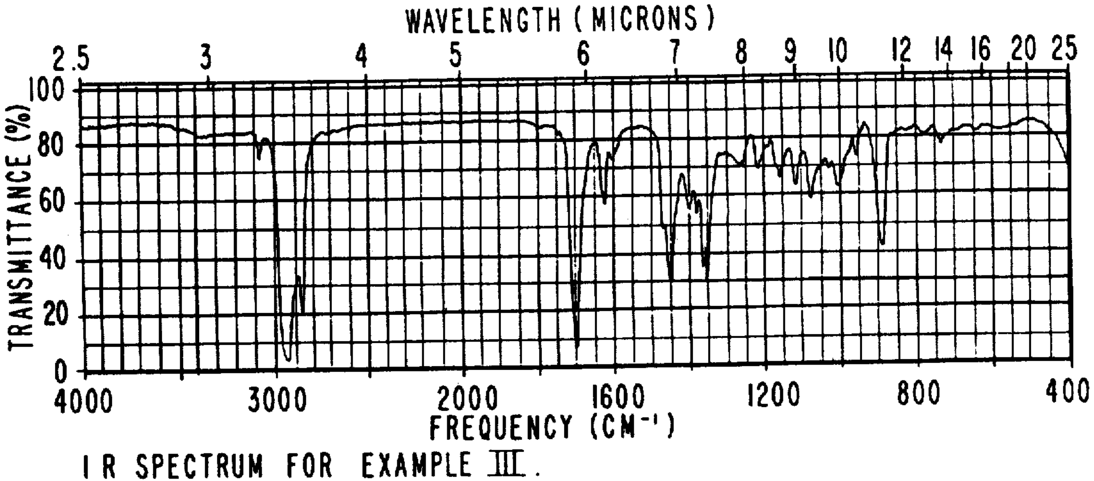
I R SPECTRUM FOR EXAMPLE III.
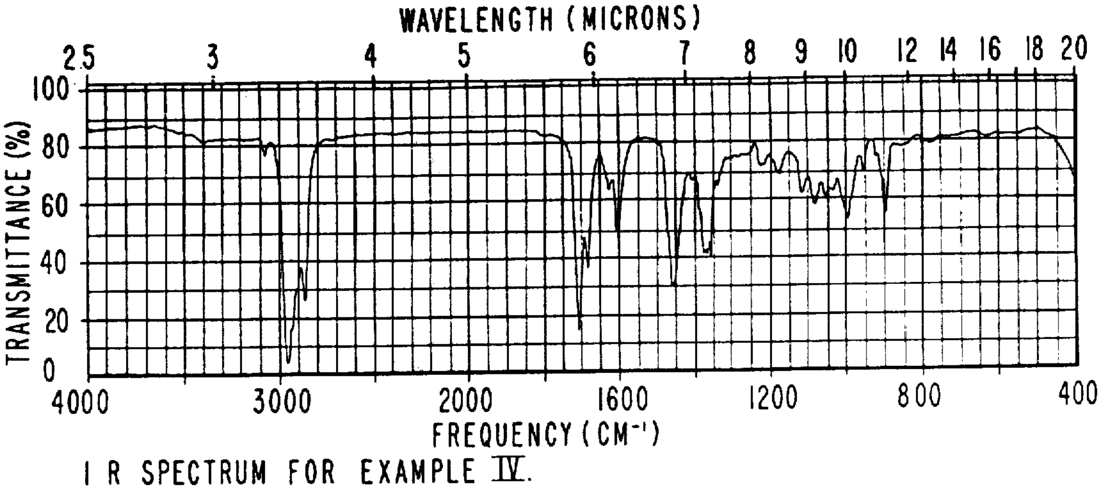
I R SPECTRUM FOR EXAMPLE IV.
FIG. 10

FIG. 11
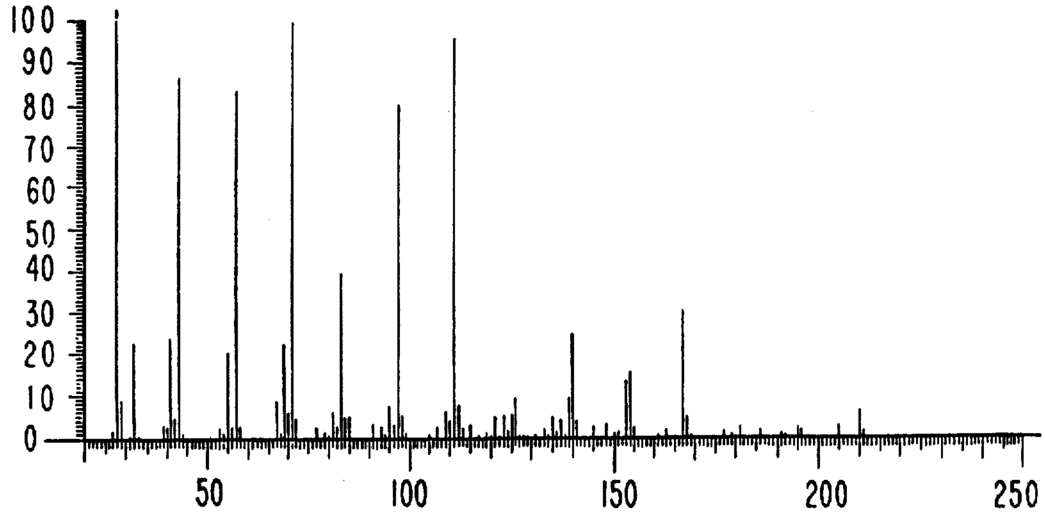
MASS SPECTRUM FOR EXAMPLE IV.
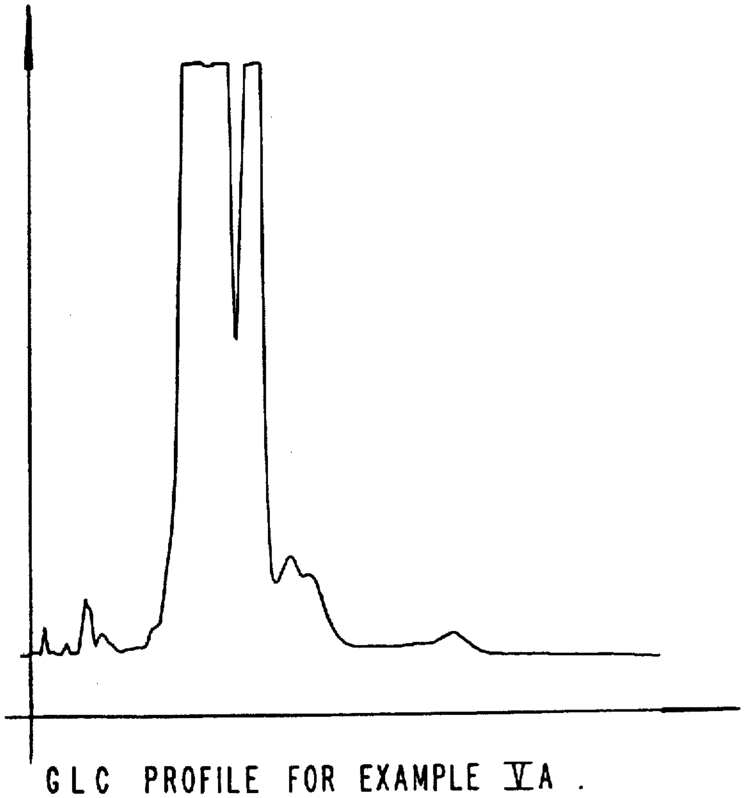
GLC PROFILE FOR EXAMPLE VA.
FIG. 12

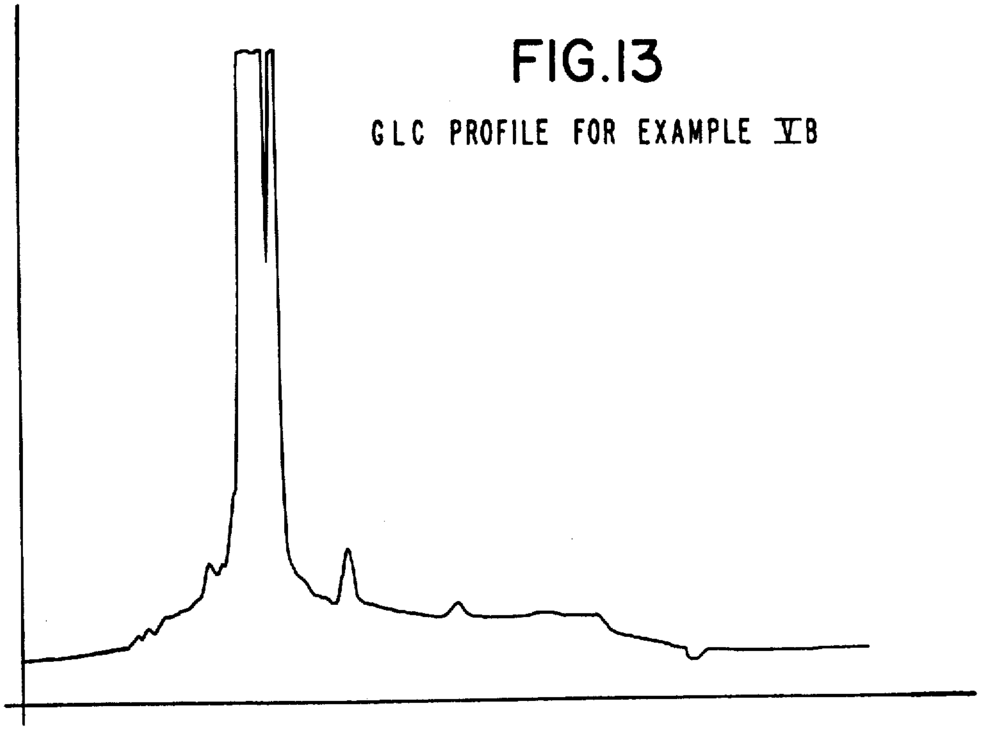
FIG.13
GLC PROFILE FOR EXAMPLE ⅤB
FIG.14
GLC PROFILE FOR EXAMPLE ⅦA.
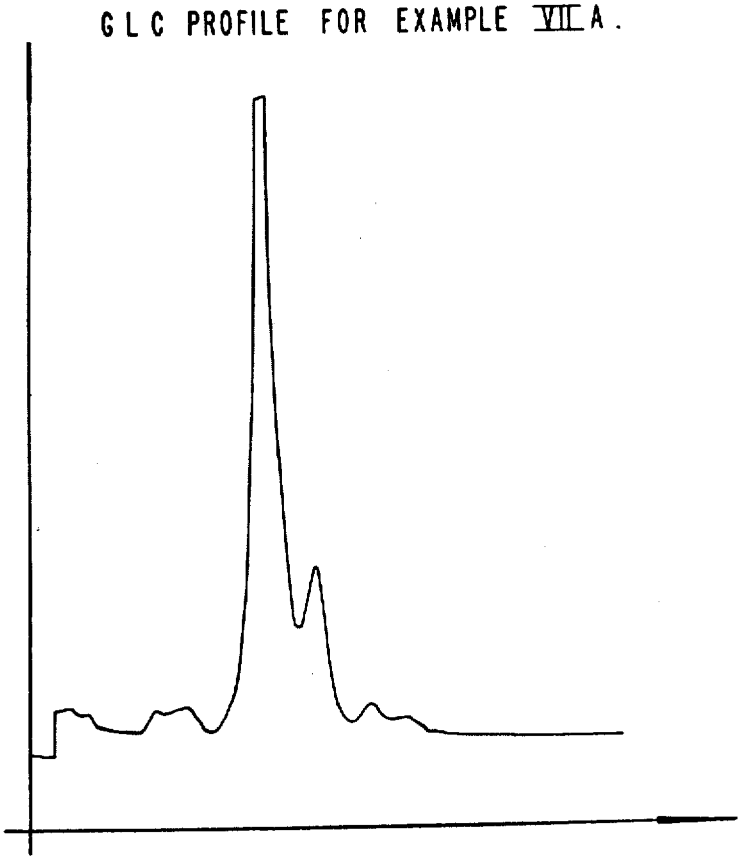

GLC PROFILE FOR EXAMPLE IX (B).

GLC PROFILE FOR EXAMPLE IX.

GLC PROFILE FOR EXAMPLE X.
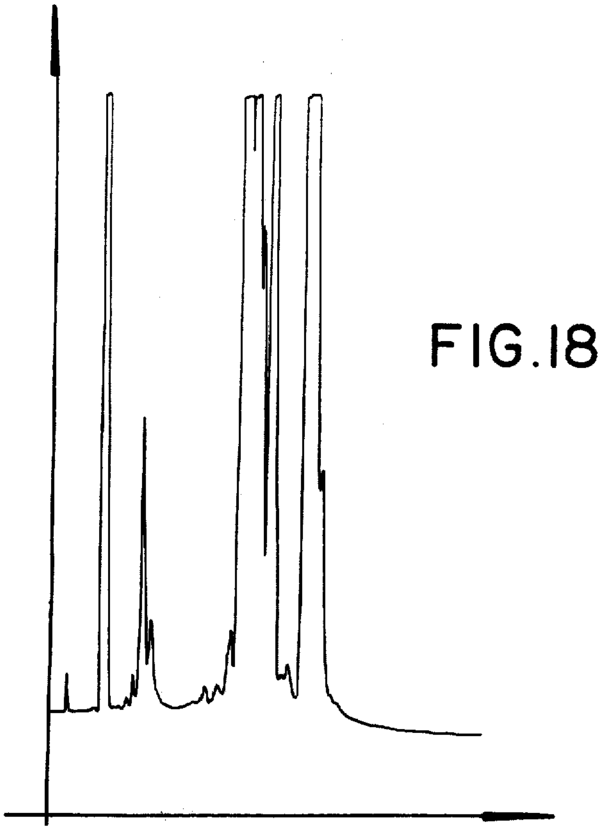
FIG.18
FIG.16
NMR SPECTRUM FOR EXAMPLE IX.
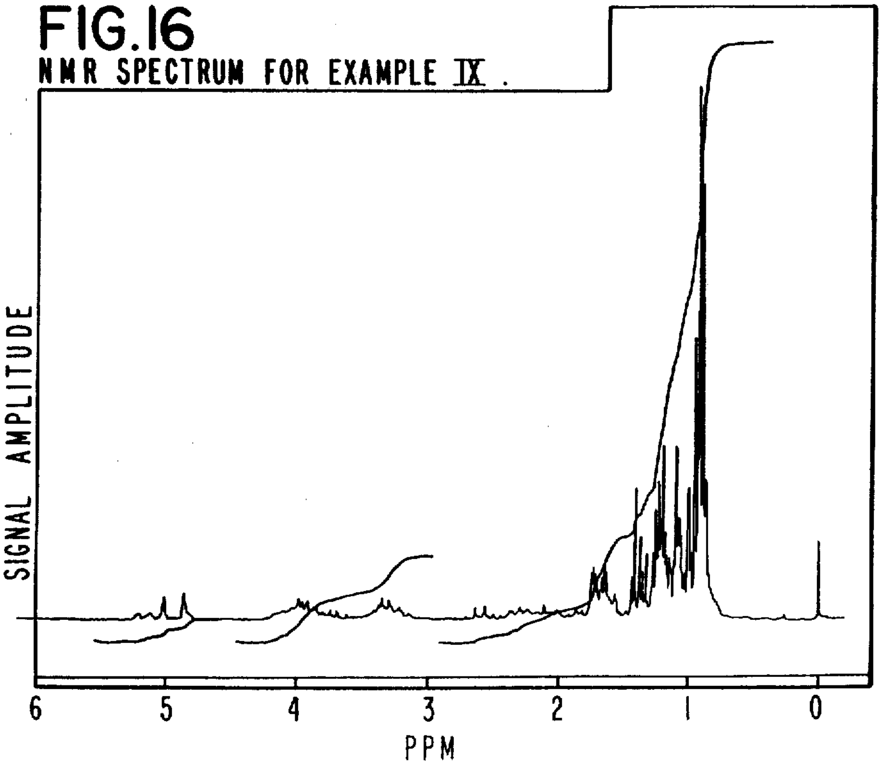

I R SPECTRUM FOR EXAMPLE IX.

GLC PROFILE FOR FRACTION 9, EXAMPLE IX (B).

ALIPHATIC BRANCHED OLEFIN DIOXOLANES, DITHIOLANES, AND OXATHIOLANES AND USES THEREOF IN AUGMENTING OR ENHANCING THE AROMA AND/OR TASTE OF CONSUMABLE MATERIALS

This application is a continuation-in-part of application for United States Letters Patent Serial No. 212,993 filed on Dec. 4, 1980, now U.S. Pat. No. 4,315,952.

BACKGROUND OF THE INVENTION

The instant invention provides branched chain olefin dioxolanes, dithiolanes and oxathiolanes which are used to augment or enhance the aroma and/or taste of consumable materials including foodstuffs, chewing gums, medicinal products, toothpastes, chewing tobaccos, perfume compositions, colognes, perfumed articles, smoking tobaccos and smoking tobacco articles.

Materials which can provide pleasant cedar, amber, woody, sweet, patchouli-like fragrance notes are known in the art of perfumery. Many of the natural materials which provide such fragrances and contribute desired nuances to perfumery compositions are high in cost, vary in quality from one batch to another and/or are generally subject to the usual variations of natural products.

There is, accordingly, a continuing effort to find synthetic materials which will replace the essential fragrance notes provided by natural essential oils or compositions thereof. Unfortunately, many of the synthetic materials either have the desired nuances only to a relatively small degree or else contribute undesirable or unwanted odor to the composition. The search for materials which can provide a more refined patchouli-like fragrance has been difficult and relatively costly in the areas of both natural products and synthetic products.

In addition, artificial flavoring agents for foodstuffs have received increasing attention in recent years. In many places such food flavoring agents have been preferred over natural flavoring agents at least in part due to their diminished cost and their reproducible flavor qualities. For example, natural food flavoring agents such as extracts, concentrates and the like are often subject to wide variations due to changes in the quality, type and treatment of the raw materials.

Such variations can be reflected in the end product and result in unfavorable flavor characteristics in said end product. Additionally, the presence of the natural product in the ultimate food may be undesirable because of increased tendency to spoil. This is particularly troublesome in food and food uses where such products as dips, soups, chips sausages, gravies and the like are apt to be stored prior to use.

The fundamental problem in creating artificial flavoring agents is that the artificial flavor to be achieved be as natural as possible. This generally proves to be a difficult task since the mechanism for flavor development in many foods is not completely known. This is particularly noticable in products having nutty, earthy, woody-balsamic, fresh walnut kernel and walnut skin flavor characteristics.

Reproduction of nutty, earthy, woody-balsamic, fresh walnut kernel and walnut skin flavor and aroma has been the subject of long and continuing searches by those engaged in the production of foodstuffs and beverages. The severe shortages of food in many parts of the world has given rise to the development of previously unused sources of protein which are unpalatable. Accordingly, the need has arisen for the use of flavoring materials which will make such sources of protein palatable to human sensory organs.

Furthermore, chemical compounds which can provide sweet, woody, vetiver and cedar-like aroma and taste nuances to smoking tobacco both prior to and on smoking in both the main stream and the side stream particularly where black tobacco aroma and taste nuances are desired and natural cigar-like taste nuances are desirable in the art of smoking tobacco aromatization. Many of the natural materials which provide such aroma and taste nuances are high in cost, unobtainable at times, vary in quality from one batch to another and/or are generally subject to the usual variations of natural products.

U.S. Pat. No. 3,760,303 (1971) discloses the cyclic acetal of 2,4-hexadienal with ethylene glycol and discloses its use in the bouquet of citrus-type odorant formulations. This compound has the structure:

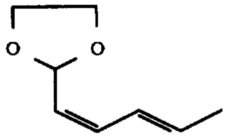

Netherlands published application No. 6,406,295 (1965) discloses gamma, delta-unsaturated aldehyde derivatives for use as perfumes, for example in soaps. These derivatives are cyclic acetals and have the structures:

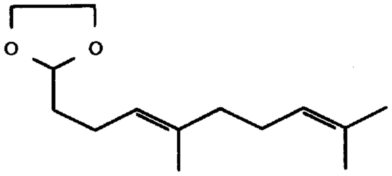

(and)

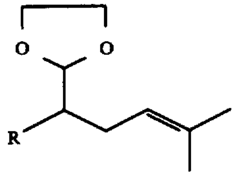

wherein R is hydrogen or methyl.

German Offenlegungschrift No. 2,103,567 (1971) discloses the use as perfumes of 2-(1-alkyl-2-alkenyl)-1,3-dioxolanes having the structure:

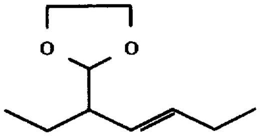

In the Federal Register 31,7563 (May 26, 1966) and in Chem. Abstracts 62, 11055e the compound having the structure:

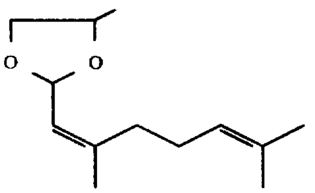

is disclosed to be useful as a synthetic food flavoring substance.

Beilstein, Vol. E II19 at page 16:5(2) discloses 2-(1-methyl-1-butenyl)1,3-dioxolane having the structure:

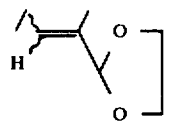

The Beilstein Abstract summarizes the article by Hibert et al. J. Am. Chem. Soc. 51 (1929) page 611 (Title: "Studies on Reactions Relating to Carbohydrates and Polysaccharides. XX. Comparison of Tendencies of Saturated and Unsaturated Aldehydes Toward Cyclic Acetal Formation"). This compound is shown to be prepared by reacting alpha methyl beta ethyl acrolein with ethylene glycol using a 40% sulfuric acid catalyst. The compound is indicated to have a boiling point of 170°-174° C. at 12 mm Hg pressure.

2-(1-ethyl-1-pentenal)-1,3-dioxolane and 2-(1-propenyl)-4-methyl-1,3-dioxolane are shown to be prepared by Heywood and Phillips, J. Org. Chem. 25 (1960) page 1699 entitled: "The Oxidation of Unsaturated Acetals and Acylals With Peracetic Acid".

None of the foregoing references discloses or implies the subject matter of the instant invention.

Furthermore, various heterocyclic compounds containing three, four or five sulfur atoms in the ring have been said to be flavorful or aroma-imparting. Thus, Chang et al in Chemistry and Industry for Nov. 23, 1968, pages 1639-1641, identified 3,5-dimethyl-1,2,4-trithiolane in the volatile flavor compounds of boiled beef; and Wada et al in U.S. Pat. No. 3,503,758 issued on Mar. 31, 1970, describes pentathiepane and various tetrathiepanes as having a good aroma and, therefore, useful as flavor enhancers. The tetra- and pentathiepanes possess a sweet, meaty flavor. Polyalkyl symmetrical trithianes have been disclosed in copending U.S. application Ser. No. 166,683 filed July 28, 1971, as having a sweet, nutty aroma and taste and suitable for fruit, net and meat flavors.

Five or six membered heterocyclic compounds having two sulfur atoms in the ring are disclosed to be useful in altering the flavor or aroma of foodstuffs in U.S. application Ser. No. 272,396 filed on July 17, 1972. Such dithio heterocyclic compounds in that case include dithiolanes and dithianes, which may be alkyl substituted or non-alkyl substituted. According to U.S. application Ser. No. 272,396, dithio heterocyclic compounds found suitable are represented by one of the following formulae:

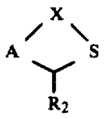 or 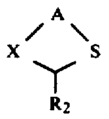

wherein X is

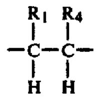 or 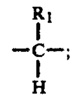;

and A is either

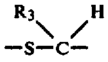 or 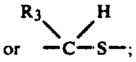;

and each of $R_1$ and $R_4$ is hydrogen or a lower alkyl radical of 1 to 3 carbon atoms.

Although a number of meta-dioxanes and meta-dioxolanes are indicated in the prior art to have specific organoleptic properties, such properties of the meta-dioxanes and meta-dioxolanes are different in kind from the aromas and tastes of the heterocyclic oxathio compounds of our invention. Thus, German Offenlegungsschrift No. 2,233,245 discloses 1,3 dioxolanes of the formula:

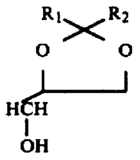

wherein $R_1$ or $R_2$ can be, interalia, ethyl or propyl as baked goods aromas.

Beilstein discloses the following:

| Compound Structure | Reference | Organoleptic Property |
|---|---|---|
| 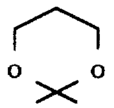 | E II 19:10 | Camphor-like smelling liquid |
| 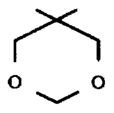 | E II 19:10 | Liquid of camphor-type odor |
| 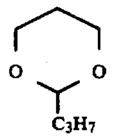 | E II 19:12 | Ether-like smelling oil |
| 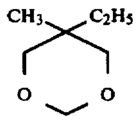 | E II 19:12 | Liquid of camphor-like smell |

-continued

| Compound Structure | Reference | Organoleptic Property |
|---|---|---|
| 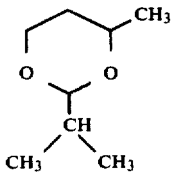 | E II 19:12 | Camphor-type smelling liquid |
| 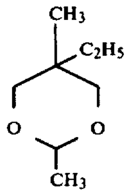 | E II 19:12 | Liquid of pleasant, camphor-like aroma |
| 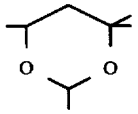 | E II 19:12 | Camphor-like smelling liquid |
| 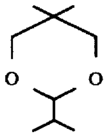 | E II 19:13 | Liquid of intense camphor-like odor |
| 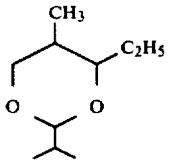 | E II 19:14 | Liquid with camphor-like odor |
| 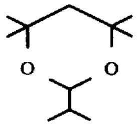 | E II 19:14 | Liquid with camphor-like odor (impure) |
| 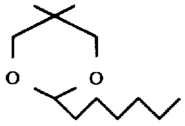 | E II 19:14 | Liquid with intense odor, reminiscent of heptanal |
| 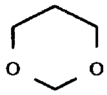 | E I 19:609 | Acetal-like smelling liquid |

Chem. Abstracts 69; 96605 Z discloses the following organoleptic properties for various metadioxanes:

| Compound Structure | Organoleptic Property |
|---|---|
| 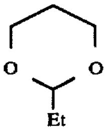 | Strong, vegetables |

-continued

| Compound Structure | Organoleptic Property |
|---|---|
| 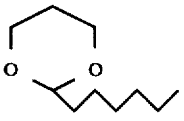 | Strong, grassy, jasmine |
| 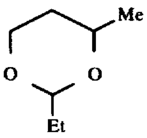 | Strong, vegetable |
| 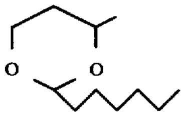 | Strong, grassy, jasmine |
| 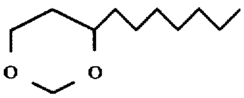 | Strong, jasmine |
| 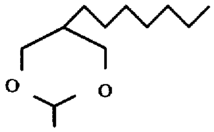 | Strong, jasmine |
| 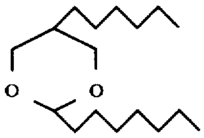 | Medium, jasmine |
| 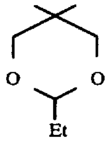 | Strong, sharp, vegetables |
| 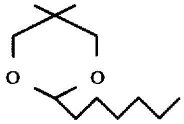 | Strong, jasmine |
| 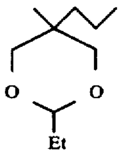 | Strong, musty, slightly chilly |
| 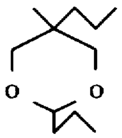 | Medium, musty, slightly chilly |

-continued

| Compound Structure | Organoleptic Property |
|---|---|
| 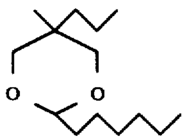 | Medium, musty, mushroom |
| 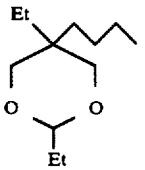 | Medium, vegetables, flower note |
| 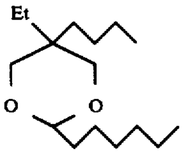 | Weak; gardenia scent |

Furthermore, in accordance with the disclosure of U.S. Pat. No. 4,031,257, it was found that certain 5 or 6 membered heterocyclic compounds having one sulfur atom and one oxygen atom in the ring (hereinafter called "oxathio heterocyclic compounds"), a number of which are novel compounds, are useful in altering, modifying or enhancing the flavor or aroma of a foodstuff, chewing gum or medicinal product. Such oxathio heterocyclic compounds include oxathiolanes and oxathianes, which may be alkyl substituted, carboxyalkyl substituted and/or acyl substituted. The oxygen atom and the sulfur atom in the ring are separated by one carbon atom. Thus, the oxathio heterocyclic compounds found suitable according to this invention may be represented by the following formula:

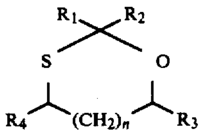

wherein n is 0 or 1; $R_1$ is hydrogen or $C_1$-$C_9$ alkyl; $R_2$ is hydrogen, lower alkyl, aryl, carboalkoxy or alkanoyl; or $R_1$ and $R_2$ taken together complete a carbocyclic ring having from five up to nine carbon atoms; $R_3$ and $R_4$ are the same or different and are each hydrogen or lower alkyl; with the sum of the carbon atoms in $R_1$, $R_2$, $R_3$ and $R_4$ being greater than or equal to 1; and the sum of the carbon atoms in $R_1$ and $R_2$ being less than or equal to nine.

Furthermore, it is disclosed in U.S. Pat. No. 4,159,347 that solid and liquid foodstuff, chewing gum, medicinal product and toothpaste compositions and flavoring compositions therefor having sweet, fruity, gooseberry, green, aniseed, licorice, floral and herbal aroma characteristics and sweet, fruity, gooseberry, green, spearmint, aniseed, licorice, floral and herbal flavor characteristics with albedo-like nuances may be provided by the utilization of cyclic acetals of 2-methyl-2-pentenal having the generic structure:

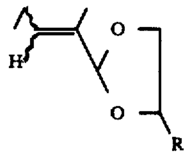

wherein R is selected from the group consisting of hydrogen and methyl and the wavy lines represent covalent bonds, and signify a "cis" or "trans" configuration of the dioxolane moiety with respect to the ethyl moiety; each moiety being bonded to the ethenyl group of the molecule.

Oxathiolanes, dioxolanes and dithiolanes are described in the following publication:

U.S. Pat. No. 4,042,601

U.S. Pat. No. 3,863,013

However, nothing existing in the prior art discloses the compounds described by the generic structure:

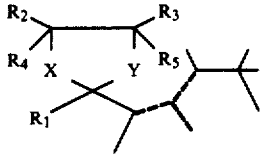

wherein $R_1$ represents $C_1$-$C_3$ lower alkyl; $R_2$, $R_3$, $R_4$ and $R_5$ represent the same or different hydrogen or $C_1$-$C_3$ lower alkyl; X and Y represent the same or different oxygen or sulfur; and one of the dashed lines represents a carbon-carbon double bond and the other of the dashed lines represent carbon-carbon single bonds.

BRIEF DESCRIPTION OF THE DRAWINGS

FIG. AA represents the GLC profile for the reaction product of Example A using a 70% sulfuric acid catalyst at 35° C.

FIG. AB represents the GLC profile for the reaction product of Example A using the Amberlyst® 15 acidic ion exchange resin catalyst at a temperature of 150° C.

FIG. AC represents the GLC profile for the reaction product of Example A, using an Amberlyst® 15 catalyst at 100° C.

FIG. AD represents the GLC profile for the reaction product of Example A, using a sulfuric acid catalyst and an alpha-methylstyrene diluent at 35° C. according to the conditions of United Kingdom Patent Specification 796,130 (crude reaction product).

FIG. AE represents the GLC profile for the reaction product of Example A, using a sulfuric acid catalyst, at 35° C. and an alpha-methyl styrene diluent according to the conditions of United Kingdom Patent Specification No. 796,130 (distilled reaction product). Distillation range: vapor temperature, 36°-40° C.; liquid temperature, 74°-94° C.; pressure, 4-5 mm/Hg.

FIG. BA represents the NMR spectrum for Peak 1 of the GLC profile of FIG. AE.

FIG. BB represents the infra-red spectrum for Peak 1 of the-GLC profile of FIG. AE.

FIG. CA represents the NMR spectrum for Peak 2 of the GLC profile of FIG. AE.

FIG. CB represents the infra-red spectrum for Peak 2 of the GLC profile of FIG. AE.

FIG. D represents the NMR spectrum for Peak 2 of the GLC profile of FIG. AB.

Figure 1:
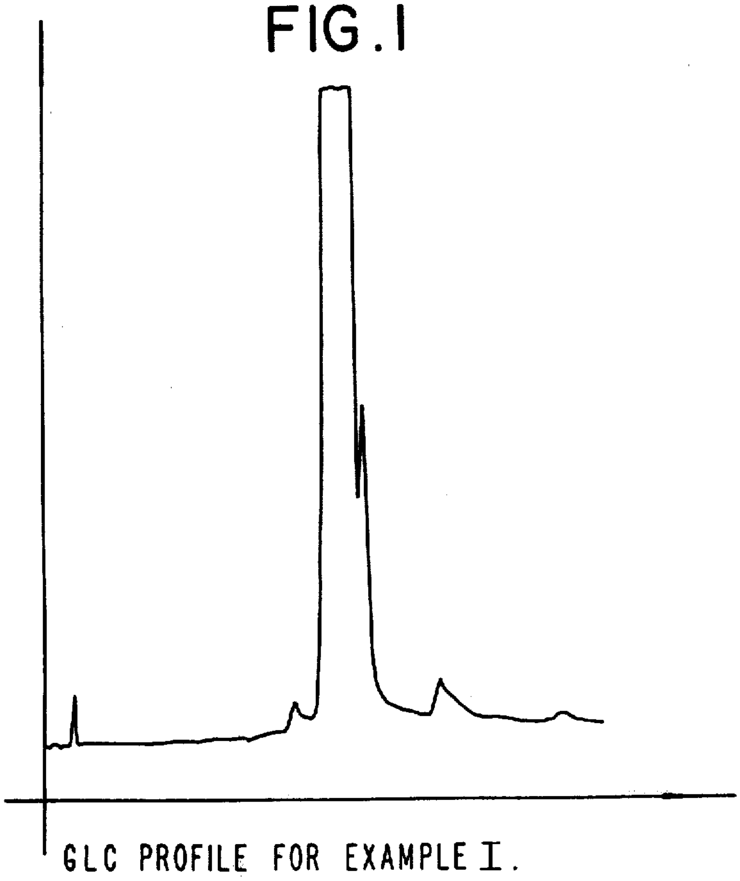

FIG. 1 sets forth the GLC profile for the reaction product of Example I, containing compounds defined according to the structure:

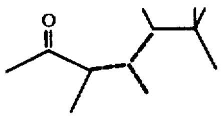

wherein in each molecule of the mixture, one of the dashed lines is a carbon-carbon double bond and the other of the dashed lines are carbon-carbon single bonds.

Figure 2A:
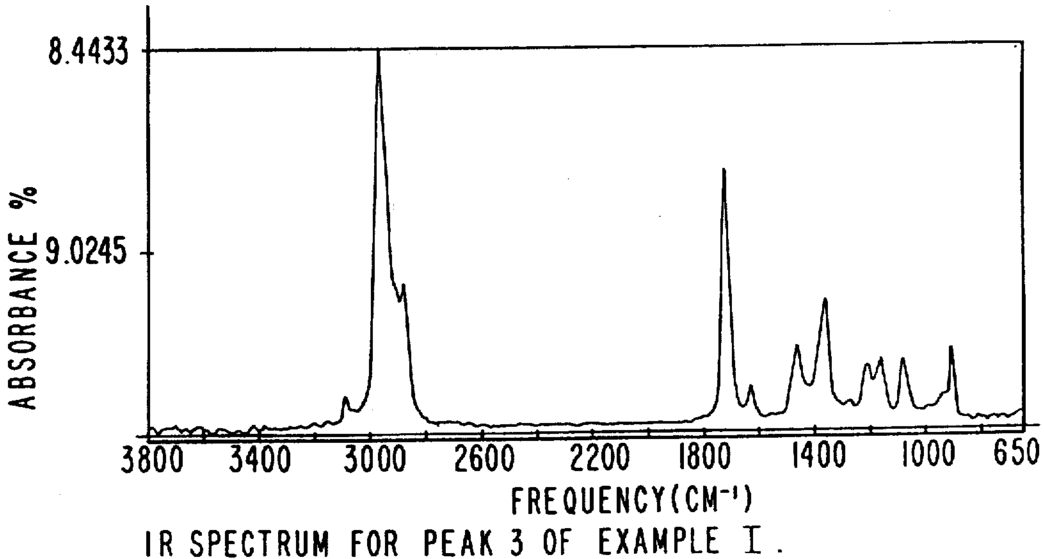

FIG. 2A represents the infra-red spectrum of Peak 3 of the GLC profile of FIG. 1.

Figure 2B:
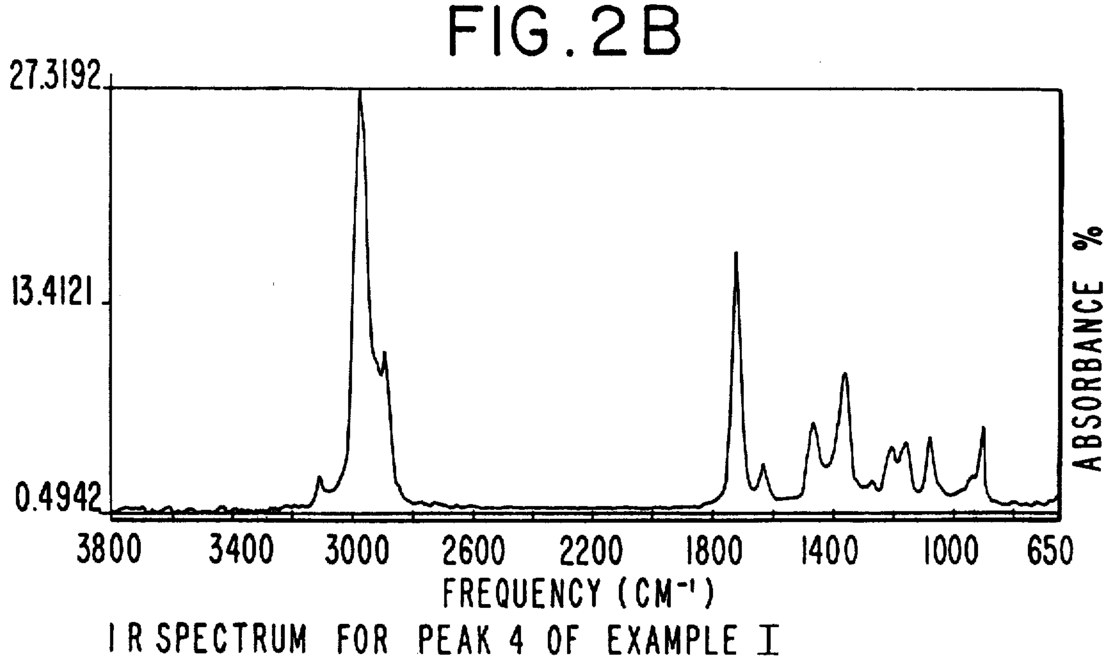

FIG. 2B represents the infra-red spectrum of Peak 4 of the GLC profile of FIG. 1.

Figure 2C:
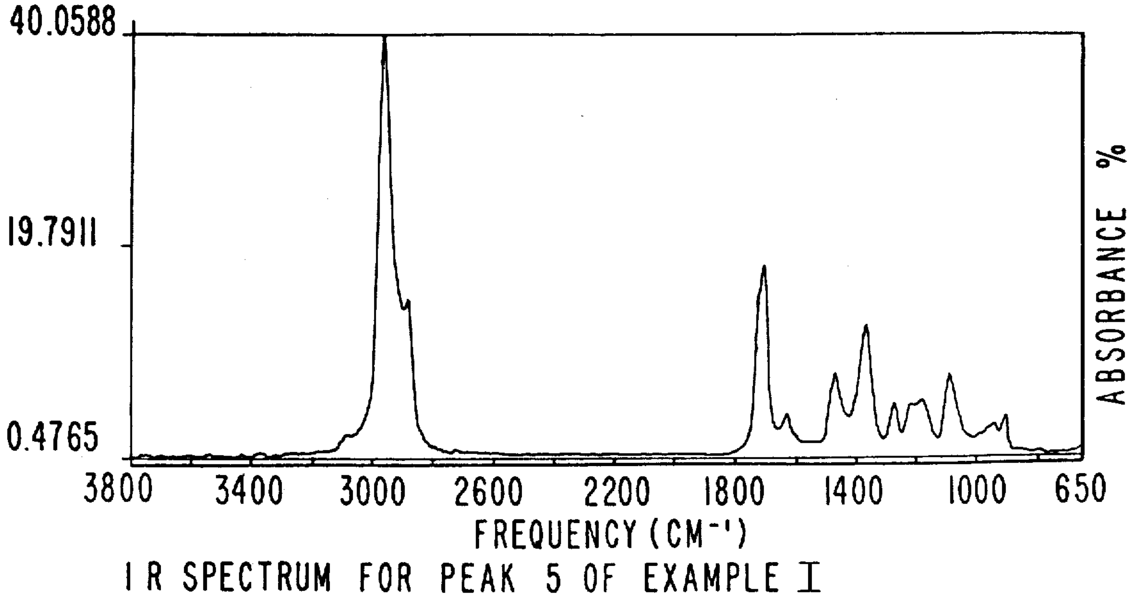

FIG. 2C represents the infra-red spectrum for Peak 5 of the GLC profile of FIG. 1.

Figure 2D:
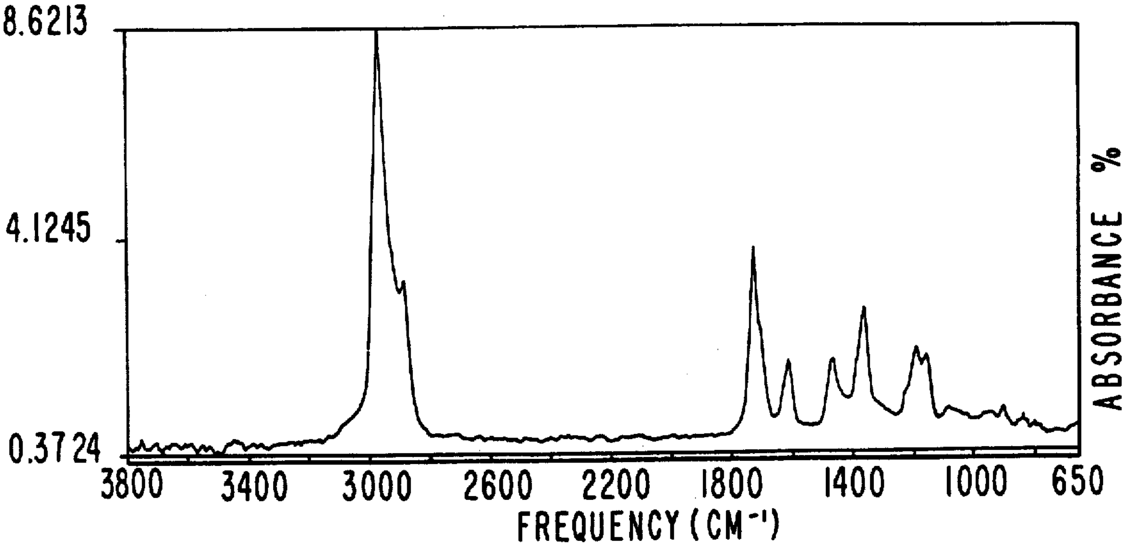

FIG. 2D represents the infra-red spectrum for Peak 6 of the GLC profile of FIG. 1.

Figure 2E:
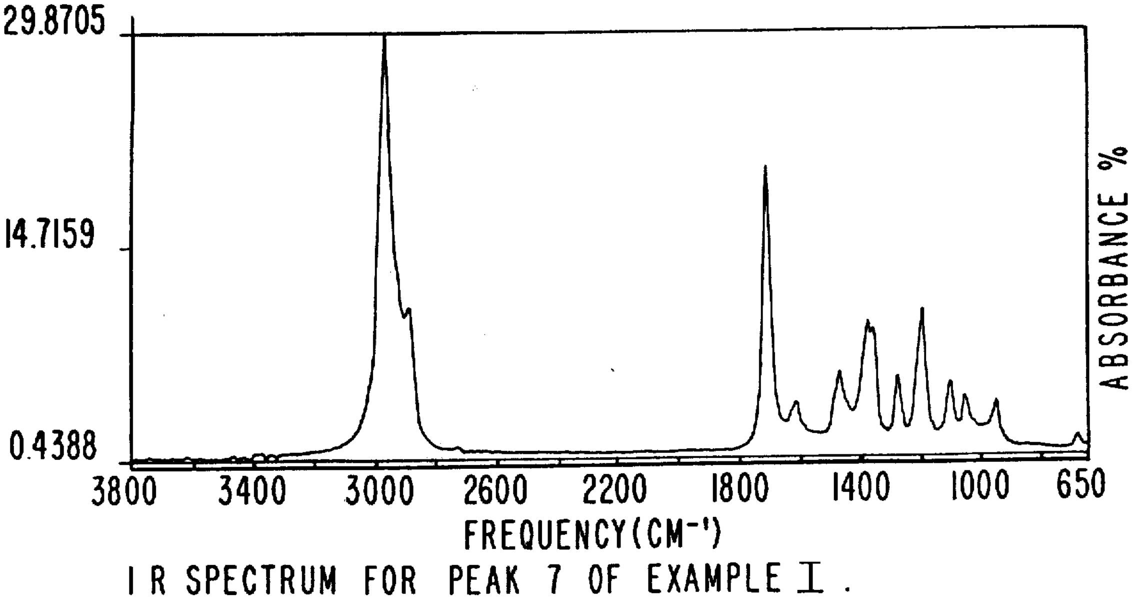

FIG. 2E represents the infra-red spectrum for Peak 7 of the GLC profile of FIG. 1.

Figure 2F:
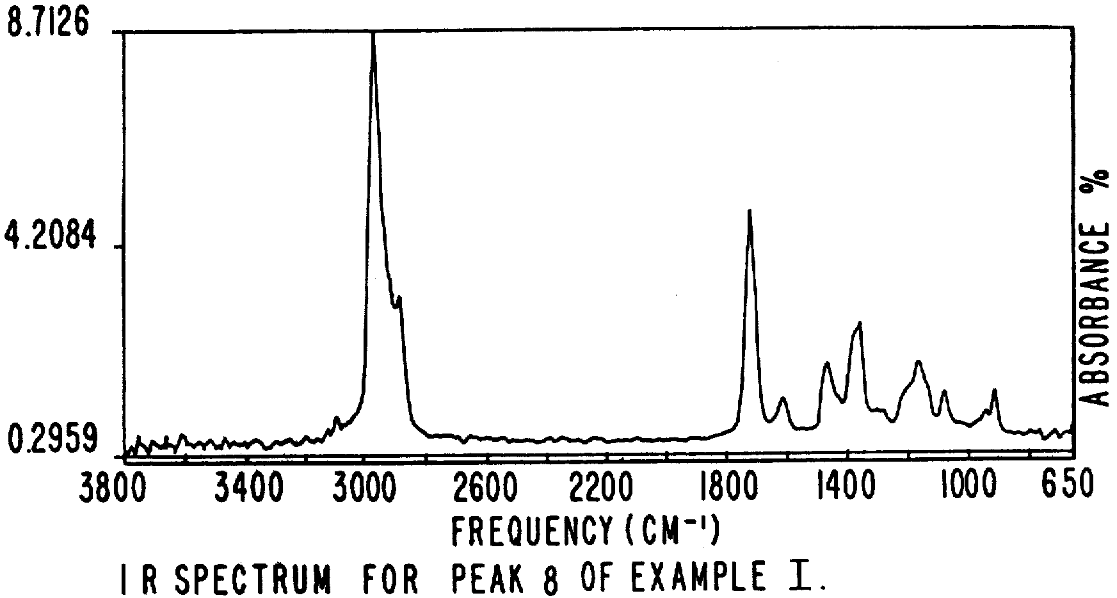

FIG. 2F represents the infra-red spectrum for Peak 8 of the GLC profile of FIG. 1.

Figure 2G:
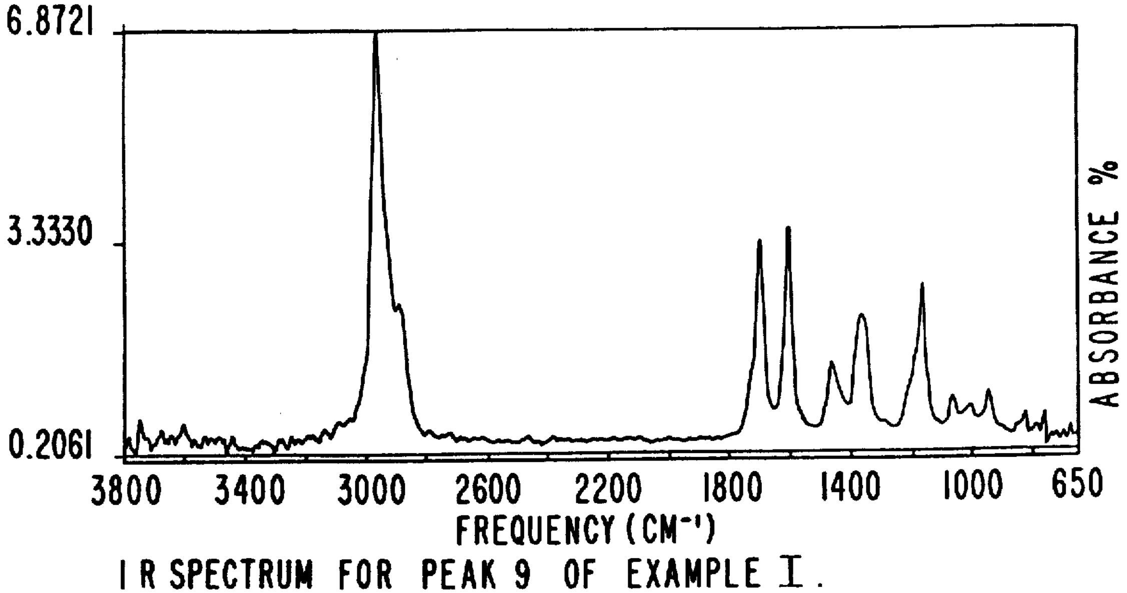

FIG. 2G represents the infra-red spectrum for Peak 9 of the GLC profile of FIG. 1.

Figure 2H:
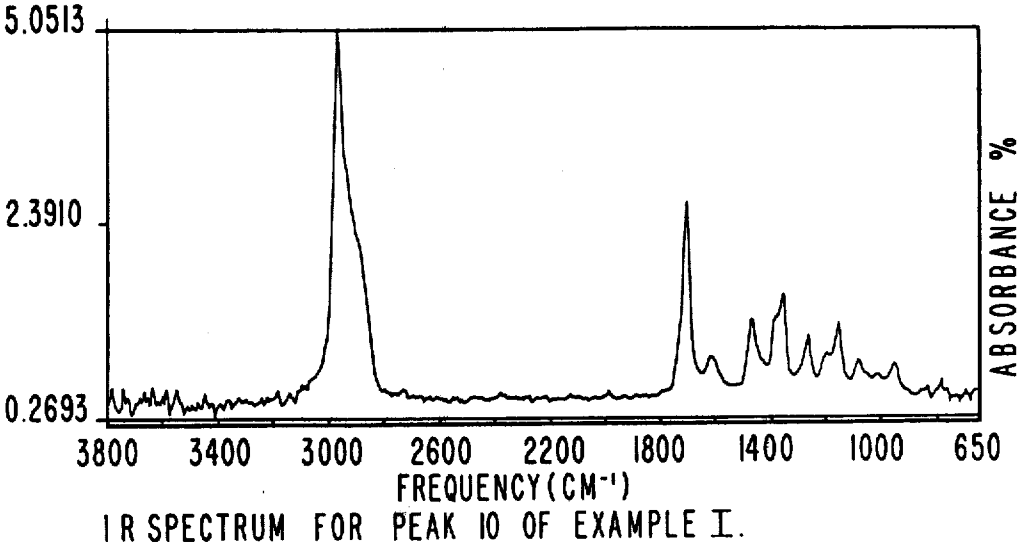

FIG. 2H represents the infra-red spectrum for Peak 10 of the GLC profile of FIG. 1.

Figure 2J:
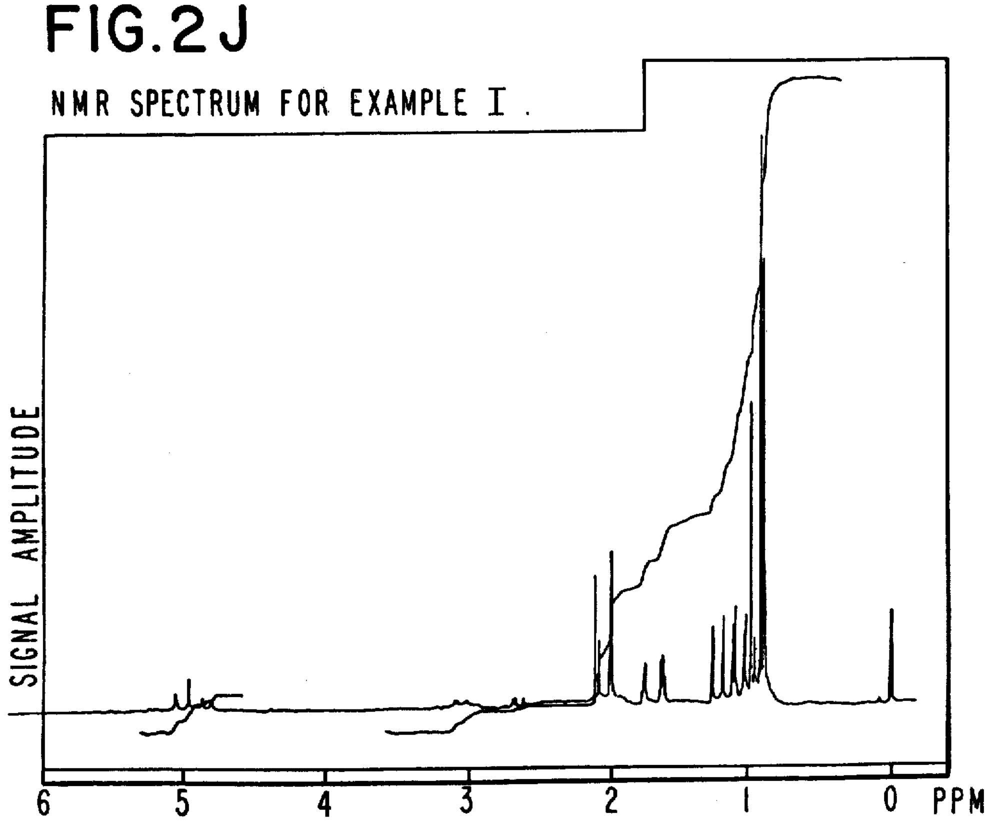

FIG. 2J represents the NMR spectrum for a mixture of compounds having the structures:

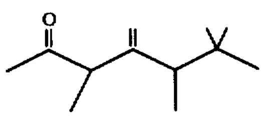

and

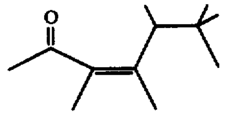

produced according to Example I.

Figure 2K:
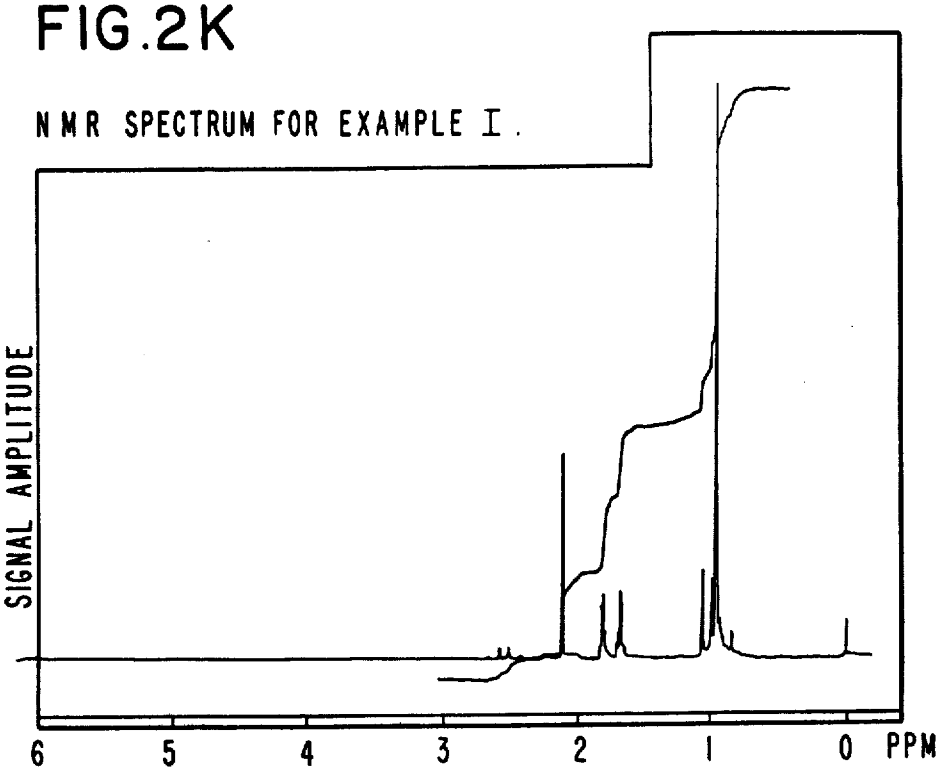

FIG. 2K represents the NMR spectrum for the compound having the structure:

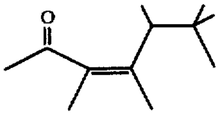

produced according to Example I.

Figure 2L:
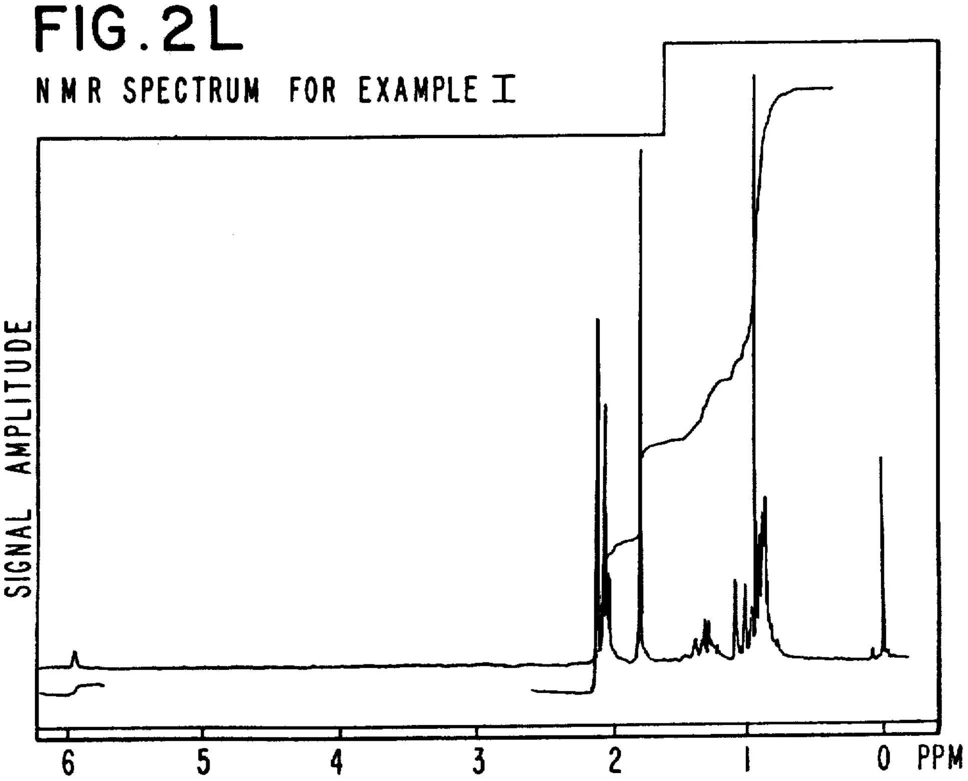

FIG. 2L represents the NMR spectrum for the compound containing the structure:

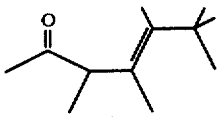

produced according to Example I.

Figure 3:
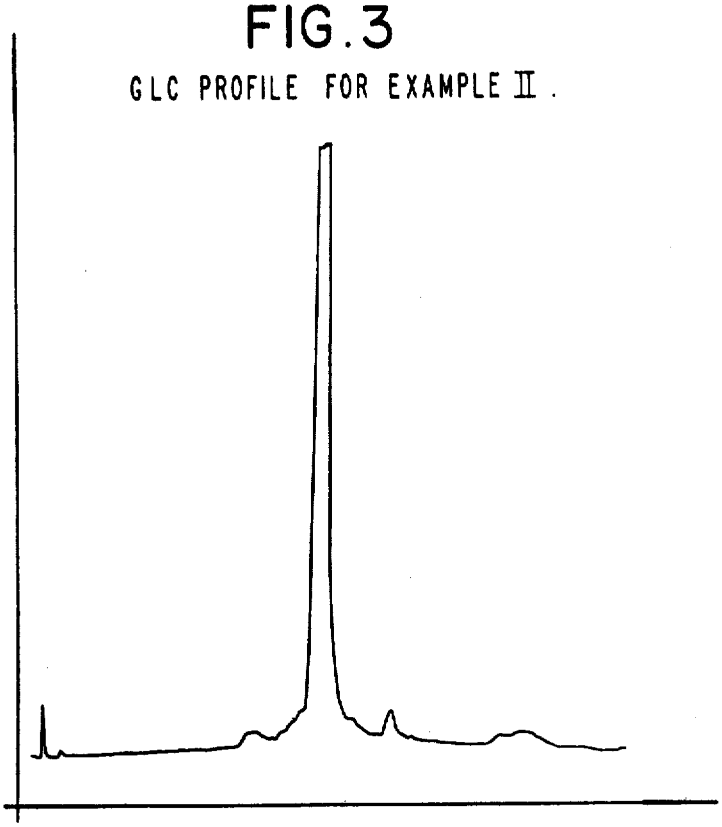

FIG. 3 represents the GLC profile for the reaction product of Example II containing a mixture of compounds, each of which is defined according to the generic structure:

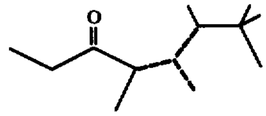

wherein in each molecule one of the dashed lines is a carbon-carbon double bond and each of the other of the dashed lines are carbon-carbon single bonds.

Figure 4:
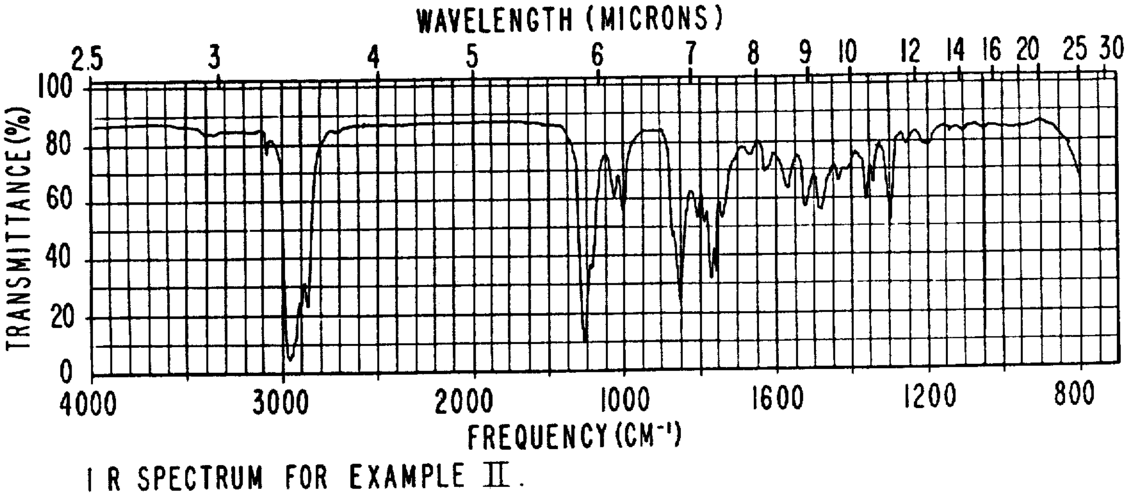

FIG. 4 represents the infra-red spectrum for the product produced according to Example II containing the compounds having the structures:

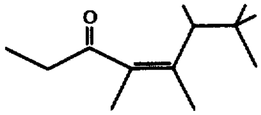

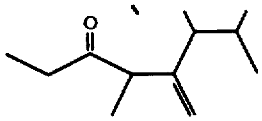

and

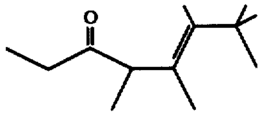

Figure 5:
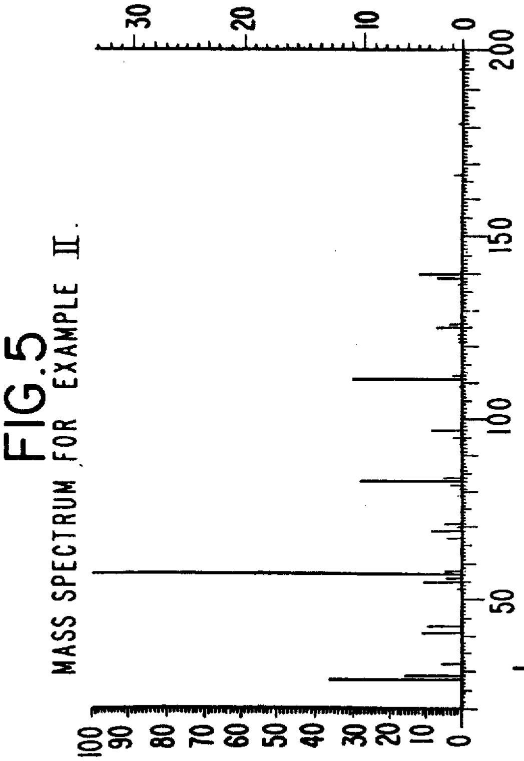

FIG. 5 represents the mass spectrum for the reaction product of Example II, containing the compounds having the structures:

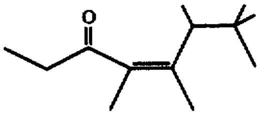

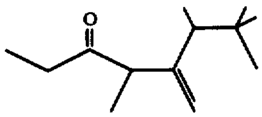

and

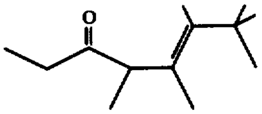

Figure 6:
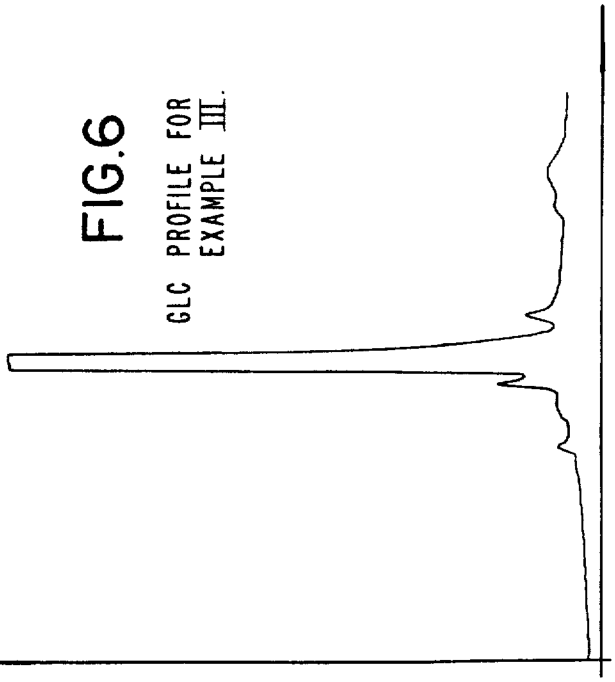

FIG. 6 represents the GLC profile for the reaction product of Example III containing compounds defined according to the generic structure:

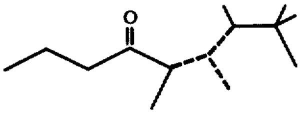

wherein in each of the molecules of the mixture, one of the dashed lines represents a carbon-carbon double bond and the other of the dashed lines represents carbon-carbon single bonds.

FIG. 7 represents the infra-red spectrum for the reaction product of Example III containing the compounds having the structures:

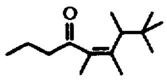

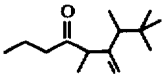

and

-continued

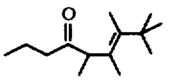

Figure 8:
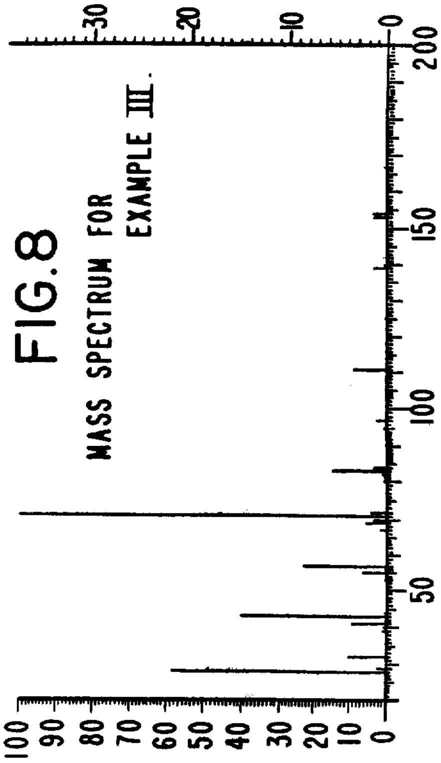

FIG. 8 represents the mass spectrum for the reaction product of Example III containing the compounds having the structures:

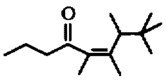
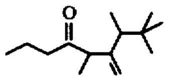

and

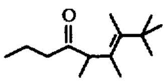

Figure 9:
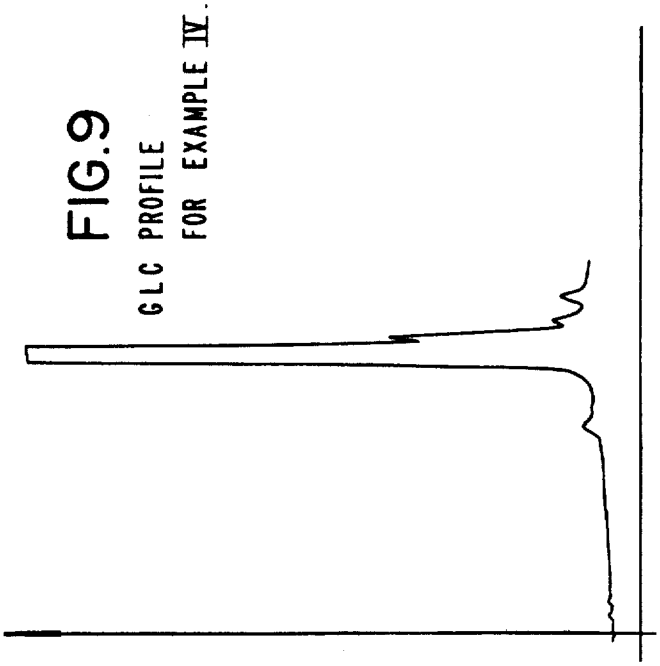

FIG. 9 represents the GLC profile for the reaction product of Example IV, containing a mixture of compounds, each of which is defined according to the generic structure:

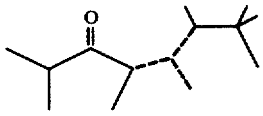

wherein in each of the molecules, one of the dashed lines represents a carbon-carbon double bond and each of the other of the dashed lines represents carbon-carbon single bonds.

FIG. 10 represents the infra-red spectrum for the reaction product of Example IV containing the compounds having the structures:

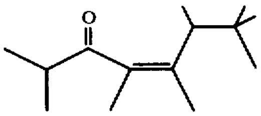
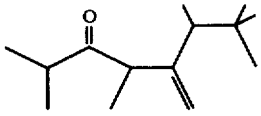

and

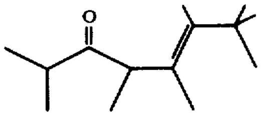

FIG. 11 represents the mass spectrum for the reaction product of Example IV containing the compounds having the structures:

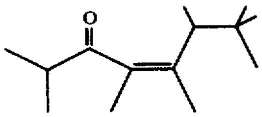
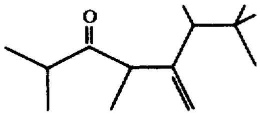

and

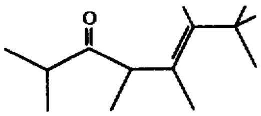

FIG. 12 represents the GLC profile for the reaction product of Example VA containing the structures defined according to the genus having the structure:

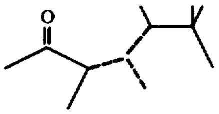

wherein in each of the molecules of the mixture, one of the dashed lines represents a carbon-carbon double bond and each of the other of the dashed lines represents carbon-carbon single bonds.

FIG. 13 represents the GLC profile for the reaction product of Example VB containing a mixture of compounds defined according to the structure:

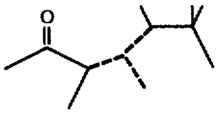

wherein in each of the molecules of the mixture, one of the dashed lines represents a carbon-carbon double bond and each of the other of the dashed lines represents carbon-carbon single bonds.

FIG. 14 represents the GLC profile for the reaction product of Example VIIA containing a mixture of compounds defined according to the genus having the structure:

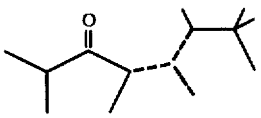

wherein in each of the molecules of the mixture, one of the dashed lines represents a carbon-carbon double bond and each of the other of the dashed lines represents carbon-carbon single bonds.

Figure 15:
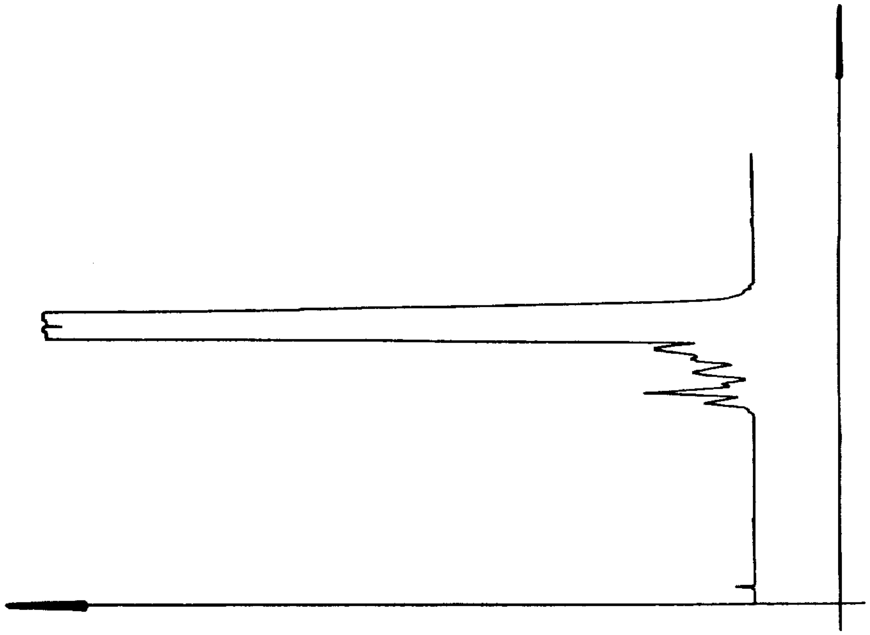

FIG. 15 sets forth the GLC profile for the reaction product produced according to Example IX(A) containing the compounds defined according to the generic structure:

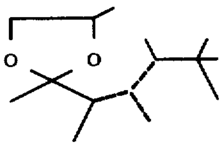

wherein one of the dashed lines in each of the molecules represents a carbon-carbon double bond and the other of the dashed lines in each of the molecules represents a carbon-carbon single bond.

FIG. 16 is the NMR spectrum for the mixture of compounds produced according to Example IX(A) containing the compounds defined according to the generic structure:

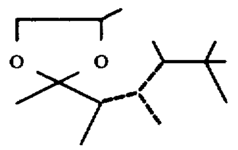

Figure 17A:
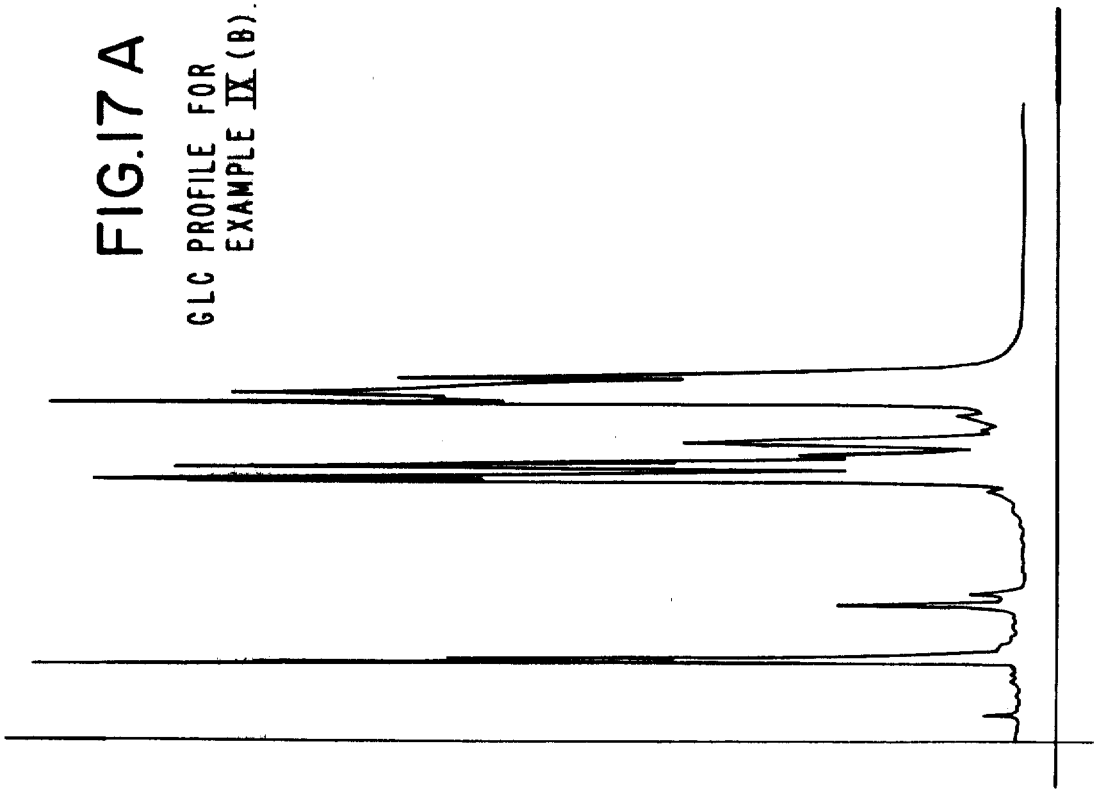
Figure 17:
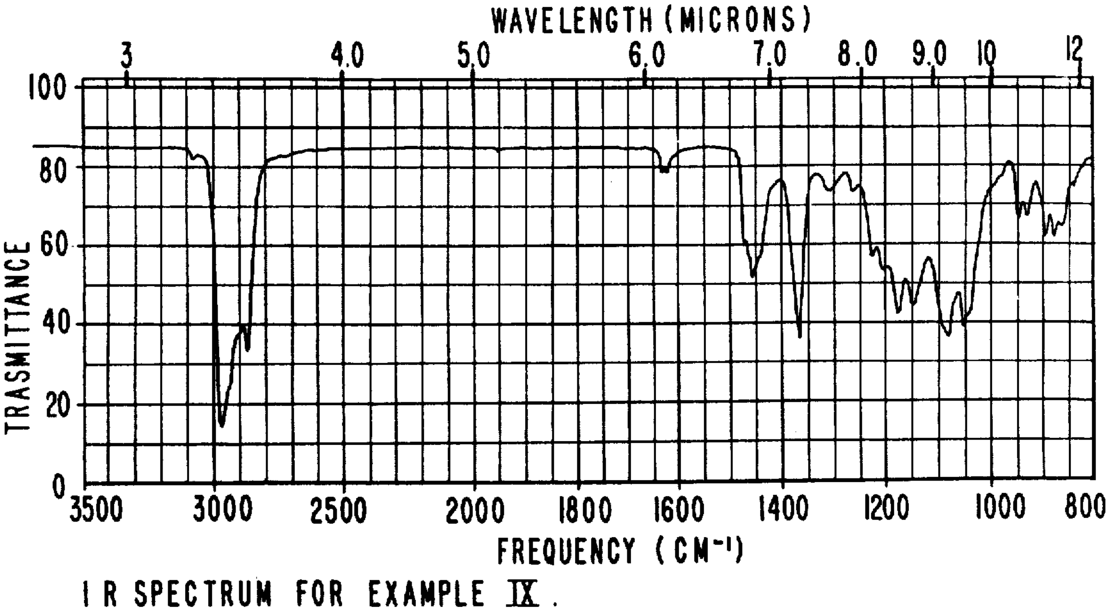

FIG. 17 is the infra-red spectrum for the product produced according to Example IX(A) containing the compounds defined according to the generic structure:

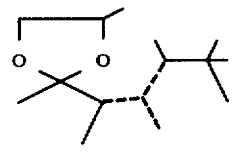

FIG. 17(A) is the GLC profile for the reaction product produced according to Example IX(B) containing the compounds defined according to the generic structure:

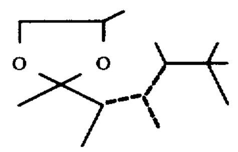

Figure 17B:
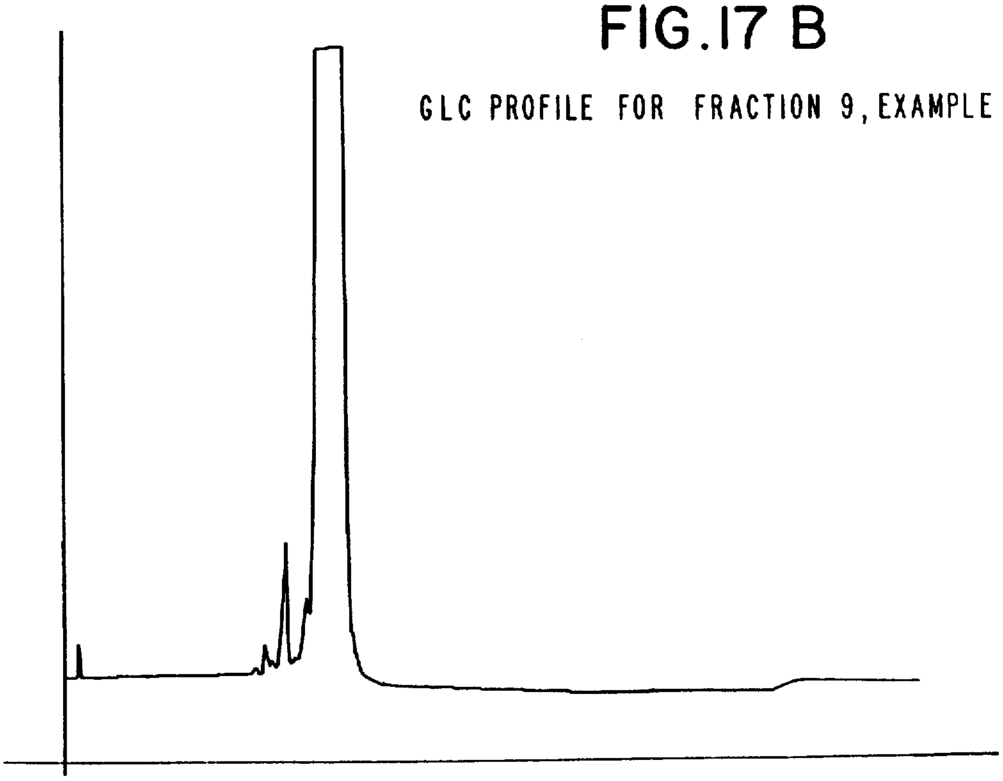

FIG. 17(B) is the GLC profile for the distillation product (Fraction 9) of the reaction product of Example IX(B) containing the compounds defined according to the generic structure:

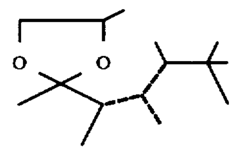

FIG. 18 is the GLC profile for the reaction product of Example X.

THE INVENTION

The instant invention provides compounds having the generic structure:

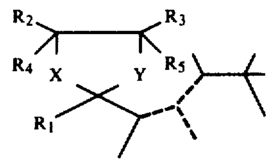

wherein $R_1$ represents $C_1$-$C_3$ lower alkyl; $R_2$, $R_3$, $R_4$ and $R_5$ represent the same or different hydrogen or $C_1$-$C_3$ lower alkyl; X and Y represent the same or different oxygen or surfur; and one of the dashed lines represents a carbon-carbon double bond and the other of the dashed lines represents carbon-carbon single bonds. These compounds are useful in augmenting or enhancing the aroma and/or taste of consumable materials including perfume compositions, colognes, perfumed articles, foodstuffs, chewing gum, toothpastes, medicinal products, chewing tobaccos, smoking tobacco articles and smoking tobacco compositions.

The class of compounds having the generic structure:

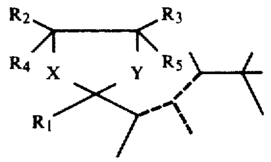

is defined in the group called "dioxolanes"; "dithiolanes" and "oxathiolanes". Thus, dithiolanes are compounds wherein both X and Y are sulfur. Dioxolanes are compounds wherein X and Y are both oxygen. Oxathiolanes are compounds wherein one of X and Y is sulfur and the other of X and Y is oxygen. Each of the compounds defined according to the generic structure:

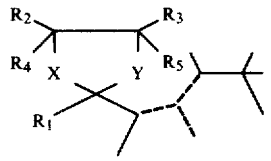

is derived using "diisoamylene" as a starting material.

Diisoamylene is indicated to be synthesized in the following references:

i—Murphy & Lane, Ind. Eng. Chem., Prod. Res. Dev., Vol. 14, No. 3, 1975 p. 167 (Title: Oligomerization of 2-Methyl-2-Butene in Sulfuric Acid and Sulfuric-Phosphoric Acid Mixtures).

ii—Whitmore & Mosher, Vol. 68, J. Am. Chem. Soc., February, 1946, p. 281 (Title: The Dopolymerization of 3,4,5,5-Tetramethyl-2-hexene and 3,5,5-Trimethyl-2-heptene in Relation to the Dimerization of Isoamylenes).

iii—Whitmore & Stahly, Vol. 67, J. Am. Chem. Soc., December, 1945, p. 2158 (Title: The Polymerization of Olefins. VIII The Depolymerization of Olefins in Relation to Intramolecular Rearrangements. II).

iv—U.S. Pat. No. 3,627,700, issued on Dec. 14, 1971, (Zuech).

v—U.S. Pat. No. 3,538,181, issued on Nov. 3, 1970, (Banks).

vi—U.S. Pat. No. 3,461,184, issued on Aug. 12, 1969 (Hay, et al.).

vii—Gurwitsch, Chemische Berichte, 1912, Vol. 2, p. 796 (Production of Di-isoamylene From Isoamylene Using Mercury Acetate Catalyst).

United Kingdom Pat. No. 796,130 published on June 4, 1958 discloses the synthesis of polyalkylindanes by means of, interalia, reacting alpha-methylstyrene with trimethylethene (2-methyl-butene-2) in the presence of an acid catalyst such as, sulfuric acid or boron trifluoride methyletherate. It is further indicated that such compounds are useful intermediates in the production of perfumery compounds. Apparently, however, the more volatile di-isoamylenes produced as side-products in the reaction 2-methyl-butene-2 with alpha-methylstyrene are discarded.

Briefly, our invention contemplates augmenting or enhancing fragrances of such consumable materials as perfumes, perfumed articles (e.g. solid or liquid anionic, cationic, nonionic or zwitterionic detergents, cosmetic powders, fabric softener compositions, dryer-added fabric softener articles, hair conditioners, and bleaching compositions including hypochlorite bleaches) and colognes by adding thereto a small, but effective, amount of at least one of the compounds defined according to the generic structure:

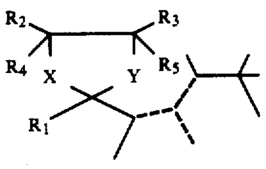

wherein $R_1$ represents $C_1$–$C_3$ lower alkyl; $R_2$, $R_3$, $R_4$ and $R_5$ represent the same or different hydrogen or $C_1$–$C_3$ lower alkyl; X and Y represents the same or different oxygen or sulfur; and one of the dashed lines represents a carbon-carbon double bond and the other of the dashed lines represent carbon-carbon single bonds.

Furthermore, our invention also contemplates augmenting or enhancing the aroma or taste of such consumable materials as foodstuffs, chewing gums, medicinal products, toothpastes and chewing tobaccos by adding thereto a small, but effective, amount of at least one of the compounds defined according to the generic structure:

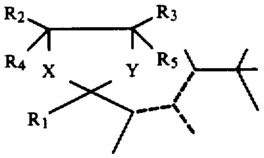

wherein $R_1$ represents $C_1$–$C_3$ lower alkyl; $R_2$, $R_3$, $R_4$ and $R_5$ represent the same or different hydrogen or $C_1$–$C_3$ lower alkyl; X and Y represent the same or different oxygen or sulfur; and one of the dashed lines represents a carbon-carbon double bond and the other of the dashed lines represent carbon-carbon single bonds.

Furthermore, our invention contemplates augmenting or enhancing the aroma or taste of smoking tobacco or smoking tobacco articles in both the main stream and the side stream both prior to and on smoking by adding to smoking tobacco or part of a smoking tobacco article such as a wrapper or filter a small, but effective, amount of at least one of the compounds defined according to the generic structure:

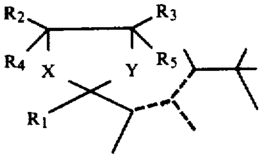

wherein $R_1$ represents $C_1$–$C_3$ lower alkyl; $R_2$, $R_3$, $R_4$ and $R_5$ represent the same or different hydrogen or $C_1$–$C_3$ lower alkyl; X and Y represent the same or different oxygen or sulfur; and one of the dashed lines represents a carbon-carbon double bond and the other of the dashed lines represent carbon-carbon single bonds.

The dioxolane, dithiolane and oxathiolane compounds of our invention augment or enhance pleasant cedar, amber-like, woody, sweet and patchouli-like aroma characteristics of perfumes, perfumed articles and colognes thereby causing one or more of said dioxolane, dithiolane or oxathiolane compounds to be useful particularly in patchouli-like fragrances. The great stability of such compounds particularly the dioxolane-type compounds causes them to be useful particularly in patchouli-fragranced hypochlorite type bleach compositions such as, for example, CLOROX®.

The dithiolane, dioxolane and oxathiolane compounds of our invention also augment or enhance the sweet, woody, vetiver-like, and cedar-like aroma and taste nuances of black tobacco and cigar tobacco both prior to and on smoking in both the main stream and the side stream.

The dioxolane, dithiolane and oxathiolane compounds of our invention also augment or enhance the aroma or taste of foodstuffs, chewing gums, medicinal products, toothpastes and chewing tobaccos by imparting or enhancing the nutty, earthy, woody-balsamic, walnut kernel-like and walnut skin flavor and aroma nuances thereof.

The dithiolanes, dioxolanes and oxathiolane compounds of our invention defined according to the generic structure:

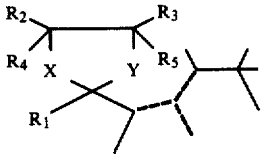

wherein $R_1$ represents $C_1$–$C_3$ lower alkyl; $R_2$, $R_3$, $R_4$ and $R_5$ represent the same or different hydrogen or $C_1$–$C_3$ lower alkyl; X and Y represent the same or different oxygen or sulfur; and one of the dashed lines represents a carbon-carbon double bond and the other of the dashed lines represents carbon-carbon single bonds, may be prepared by first preparing diisoamylene by means of dimerization of isoamylene having the structure:

whereby the compounds having the structures:

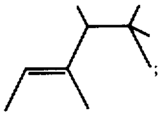; 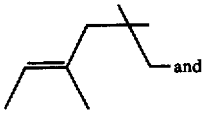 and 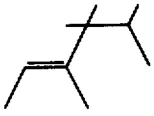

are formed. These compounds can also be defined according to the structure:

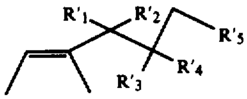

wherein $R'_1$, $R'_2$, $R'_3$, $R'_4$ and $R'_5$ represent hydrogen or methyl with the provisos that (i) at least one of $R'_1$ and $R'_2$ represents methyl, (ii) at least one of $R'_3$ and $R'_4$ represents methyl; (iii) the sum of the carbon atoms in $R'_1$, $R'_2$, $R'_3$, $R'_4$ and $R'_5$ is 3 and (iv) $R'_1$ and $R'_2$ represent hydrogen when $R'_5$ is methyl. These diisoamylene compounds may be prepared according to the procedures of the following references:

i—Murphy & Lane, Ind. Eng. Chem., Prod. Res. Dev., Vol. 14, No. 3, 1975 p. 167 (Title: Oligomerization of 2-Methyl-2-Butene in Sulfuric and Sulfuric-Phosphoric Acid Mixtures).

ii—Whitmore & Mosher, Vol. 68, J. Am. Chem. Soc., February, 1946, p. 281 (Title: The Depolymerization of 3,4,5,5-Tetramethyl-2-hexene and 3,5,5-Trimethyl-2-heptene in Relation to the Dimerization of Isoamylenes).

iii—Whitmore & Stahly, Vol. 67, J. Am. Chem. Soc., December, 1945, p. 2158 (Title: The Polymerization of Olefins. VIII The Depolymerization of Olefins in Relation to Intramolecular Rearrangements. II).

iv—U.S. Pat. No. 3,627,700, issued on Dec. 14, 1971, (Zuech).

v—U.S. Pat. No. 3,538,181, issued on Nov. 3, 1970, (Banks).

vi—U.S. Pat. No. 3,461,184, issued on Aug. 12, 1969 (Hay et al).

vii—Gurwitsch, Chemische Berichte, 1912, Vol. 2, p. 796 (Production of Di-isoamylene From Isoamylene Using Mercury Acetate Catalyst).

The resulting compounds are then acylated or thioacylated with an acylating agent such as an acylhalide or an acylanhydride or a thioacylhalide or a thioacylanhydride having the generic structure:

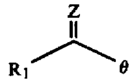
or
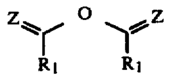

wherein Z represents oxygen or sulfur; wherein $R_1$ represents $C_1$-$C_3$ lower alkyl and wherein $\theta$ represents halogen which may be chloro or bromo, whereby a compound having the structure:

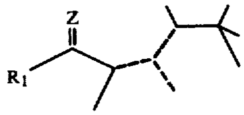

is formed wherein Z is one of oxygen or sulfur and one of the dashed lines is a carbon-carbon double bond and the other of the dashed lines in each of the molecules formed is a carbon-carbon single bond. Such compounds can be further defined according to one of the structures:

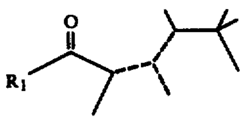
or
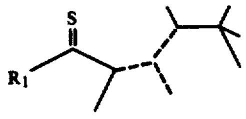

wherein $R_1$ is $C_1$-$C_3$ lower alkyl and one of the dashed lines in each of the molecules represents a carbon-carbon double bond and the other of the dashed lines in each of the molecules represents carbon-carbon single bonds.

These thiones or ketones, as the case may be, are then further reacted with either a thiirane, epoxide, glycol, dithiol or thiol-alcohol having one of the structures:

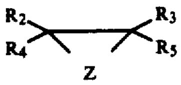
or
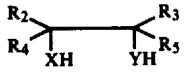

thereby forming a compound having the generic structure:

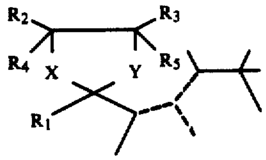

wherein $R_1$ represents $C_1$-$C_3$ lower alkyl; $R_2$, $R_3$, $R_4$ and $R_5$ represent the same or different hydrogen or $C_1$-$C_3$ lower alkyl; X and Y represent the same or different oxygen or sulfur; and one of the dashed lines represents a carbon-carbon double bond and the other of the dashed lines represents carbon-carbon single bonds.

The foregoing sequence of reactions is illustrated as follows:

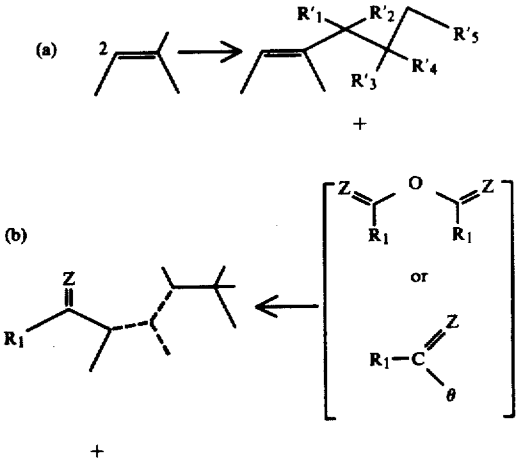

-continued (c) 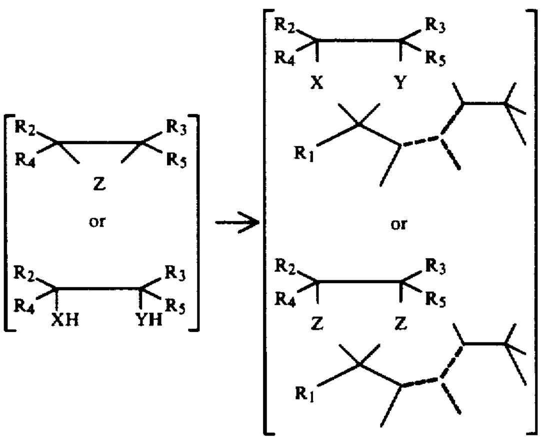

wherein $R_1$ represents $C_1$–$C_3$ lower alkyl; $R_2$, $R_3$, $R_4$ and $R_5$ represent the same or different hydrogen or $C_1$–$C_3$ lower alkyl; X and Y represent the same or different oxygen or sulfur; and one of the dashed lines represents a carbon-carbon double bond and the other of the dashed lines represents carbon-carbon single bonds and wherein Z represents one of X or Y and wherein $R'_1$, $R'_2$, $R'_3$, $R'_4$ and $R'_5$ represent hydrogen or methyl with the provisos that (i) at least one or $R'_1$ and $R'_2$ represents methyl; (ii) at least one of $R'_3$ and $R'_4$ represents methyl; (iii) the sum of the carbon atoms in $R'_1$, $R'_2$, $R'_3$, $R'_4$ and $R'_5$ is 3 and (iv) $R'_1$ and $R'_2$ represent hydrogen when $R'_5$ is methyl.

The compounds produced according to our invention may be in the form of mixtures of isomers; that is, mixtures of "cis" and "trans" isomers as well as mixtures of "stereoisomers". Thus, the compound having the structure:

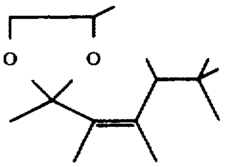

for example, may have the methyl group on the dioxolane ring either in "cis" or "trans" configuration about the said dioxolane ring as follows:

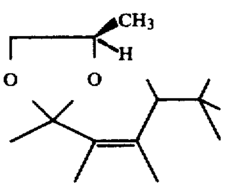

or

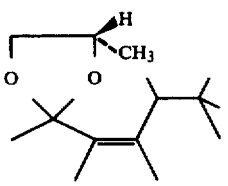

Furthermore, the double bond in the side chain of the dioxolane ring may be in either "cis" or "trans" configuration with respect to the methyl moieties bonded to the carbon atoms forming the carbon-carbon double bond as follows:

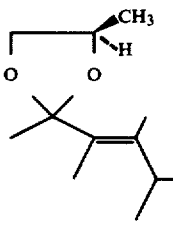

and

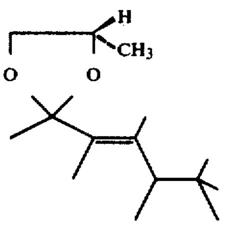

Furthermore, a "stereoisomer" of such a compound may be shown as follows:

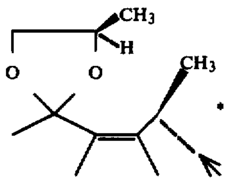

wherein the symbol:

" • "

represents the location of an asymetric carbon atom.

Furthermore, the foregoing reaction sequence may be more specifically illustrated by the following reaction wherein the thiirane or epoxide compound may be in either "cis" or "trans" configuration and wherein $R_4$ and $R_5$ represent hydrogen:

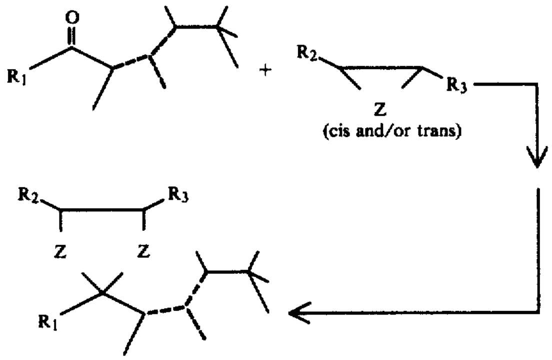

The reaction products of our invention which are oxathianes may also be prepared by first reacting the diisoamylene acylation derivatives with phosphorous pentasulfide to form a thioketone and then reacting the resulting thioketone with vicinal epoxides according to the reaction scheme:

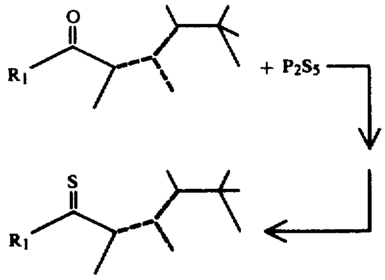

-continued

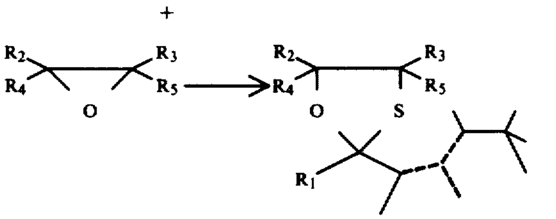

wherein $R_1$ represents $C_1$–$C_3$ lower alkyl; $R_2$, $R_3$, $R_4$ and $R_5$ represent the same or different hydrogen or $C_1$–$C_3$ lower alkyl; X and Y represent the same or different oxygen or sulfur; and one of the dashed lines represents a carbon-carbon double bond and the other of the dashed lines represents carbon-carbon single bonds.

When carrying out the reaction scheme:

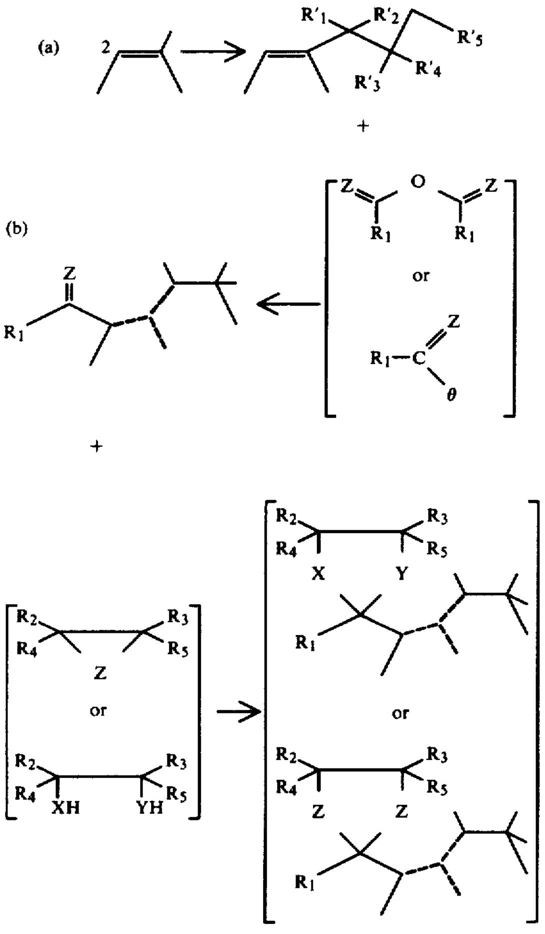

the diisoamylene material which is first produced may either be separated into constitutent isomers or may be used "as is" in the subsequent acylation reaction or thioacylation reaction. Thus, for example, the subsequent acylation reaction may be carried out on the mixture of diisoamylene molecules according to the reaction:

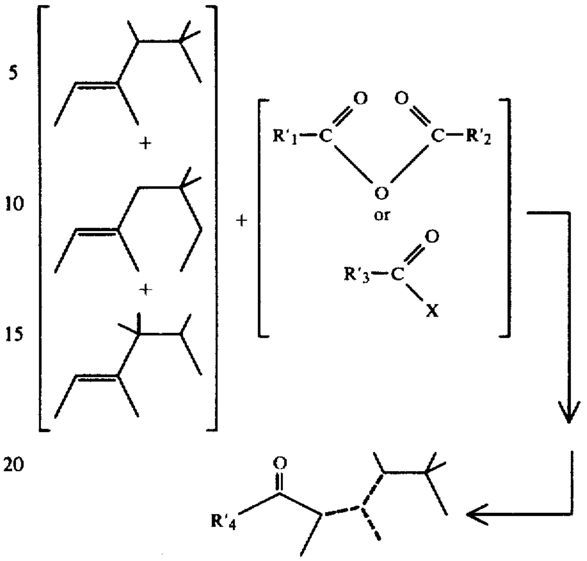

wherein the acylation is carried out using an organic acid anhydride or a mixed anhydride or an acyl halide or a thioacyl halide or an organic thioacid anhydride. In the foregoing reaction, $R_1'$, $R_2'$ and $R_3'$ represent the same or different $C_1$–$C_3$ alkyl, methyl, ethyl, n-propyl or i-propyl; and $\theta$ is chloro or bromo and one of the dashed lines in the reaction product represents a carbon-carbon double bond and each of the other dashed lines represent carbon-carbon single bonds. This reaction is carried out in the presence of an acid catalyst which may be either a Lewis acid or a mineral acid. When using Lewis acids such as boron trifluoride etherate, zinc chloride, aluminum chloride, zinc bromide, diethyl aluminum chloride, ethyl aluminum dichloride, stannic chloride or zinc bromide, the temperature of reaction may vary between 0° C. and 80° C., with a preferred reaction temperature of between 10° C. and 50° C. When using a mineral acid, such as methane sulfonic acid, sulfuric acid, phosphoric acid, polyphosphoric acid, or a mixtur of methane sulfonic acid and phosphorous pentoxide, the temperature of reaction may vary between 25° C. and 150° C. with a preferred reaction temperature of between 40° C. and 110° C.

The ratio of dimer of isoamylene:acylating agent or thioacylating agent (e.g., acetic anhydride) may vary between 1:1.1 and 2:1.0 with a preferable mole ratio of diisoamylene dimer:acylating agent being about 1:0.7. Various acyl anhydrides, thioacyl anhydrides, acyl halides or thioacyl halides may be used, for example:

Acetic anhydride
Thioacetic anhydride
Propionic anhydride
Thiopropionic anhydride
n-Butyric anhydride
n-Thiobutyric anhydride
Isobutyric anhydride
Thioisobutyric anhydride
Acetic propionic anhydride
Thioacetic thiopropionic anhydride
Acetic n-butyric anhydride
Thioacetic thio-n-butyric anhydride
Acetic i-butyric anhydride
Thioacetic thio-i-butyric anhydride Propionic i-butyric anhydride
Thiopropionic thioisobutyric anhydride
Propionic n-butyric anhydride
Thiopropionic thio-n-butyric anhydride
Acetyl chloride
Thioacetyl chloride
Acetyl bromide
Thioacetyl bromide
n-Propenyl chloride
Thio-n-propenyl chloride
n-propenyl bromide
Thio-n-propenyl bromide
n-Butyric chloride
Thio-n-butyric chloride
Isobutyric chloride
Thioisobutyric chloride
n-butyric bromide
Thio-n-butyric bromide The concentration of catalysts in the reaction mass may vary from 2.5 weight percent to 150 weight percent with a preferred concentration (Lewis acid or mineral acid) being between 5 and 10 percent by weight of the reaction mass.

Although an inert solvent may be used in the reaction mass (e.g., benzene, toluene, xylene, dihydrochloromethane or 1,2-dichlorobenzene) it is preferred that no solvents be used and that the reaction mass be carried out in the absence of solvent.

Although pressures greater than or less than atmospheric pressure may be used, no specific advantages are seen in using higher or lower pressures insofar as conversion, yield or time of reaction is concerned.

Accordingly, it is most preferred to use atmospheric pressure as a reaction condition in the acylation or thioacylation reaction.

In carrying out the reaction whereby the ketone is reacted with the epoxide or thiirane to form the oxathiolane, dithiolane or dioxolane according to the sequence:

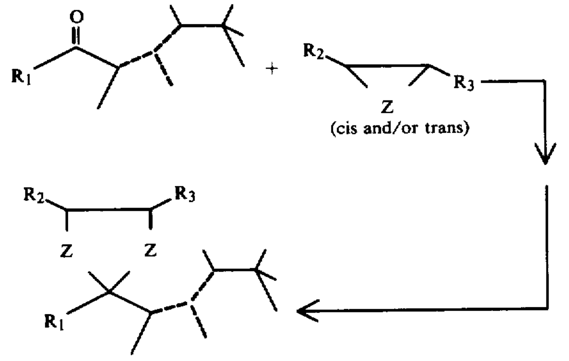

or in carrying out the reaction of the ketone or thioketone with the diol, dithiol or thiol alcohol according to the reaction sequence, for example:

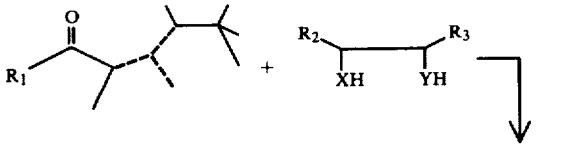

-continued

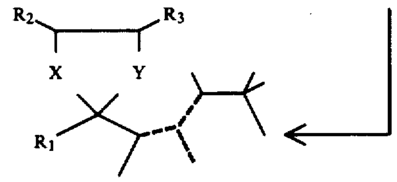

This reaction is carried out in the presence of an acid catalyst which, in this case, is a Lewis acid such as boron trifluoride, boron trifluoride etherate, zinc chloride, aluminum chloride, zinc bromide, diethyl aluminum chloride, ethyl aluminum dichloride, stannic chloride or zinc bromide. The temperature of reaction may vary between 0° and 80° C. with a preferred reaction temperature of between 10° C. and 50° C.

The mole ratio of acylated or thioacylated diisoamylene having the structure:

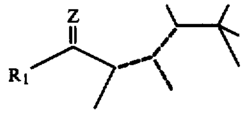

to epoxide or thiirane having the structure:

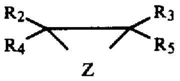

or glycol, dithiol or hydroxythiol having the structure:

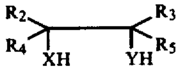

may vary from 1:1 of acylated of thioacylated diisoamylene: epoxide, thiirane, glycol, dithiol or thioalcohol up to 1:2.

The following table set forth reactants and dioxolane, oxathiolane, and dithiolane reaction products contemplated by our invention:

TABLE I

| Thiirane, Epoxide, Glycol, Thioalcohol or Dithiol Reactant | Acylated or Thioacylated Diisoamylene Reactant | Dioxolane, Dithiolane or Oxathiolane Reaction Product |
|---|---|---|
| 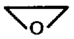 | 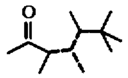 | 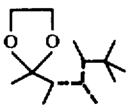 |
| 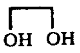 | 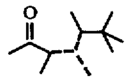 | 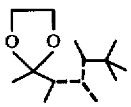 |
| 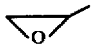 | 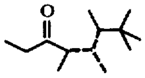 | 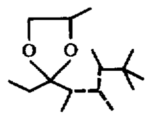 |

TABLE I-continued

| Thiirane, Epoxide, Glycol, Thioalcohol or Dithiol Reactant | Acylated or Thioacylated Diisoamylene Reactant | Dioxolane, Dithiolane or Oxathiolane Reaction Product |
|---|---|---|
| 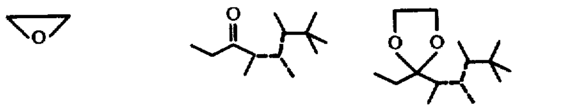 | | |
| 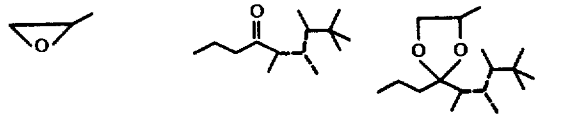 | | |
| 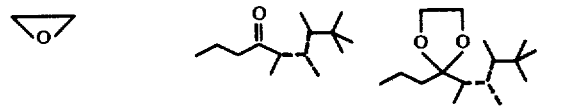 | | |
| 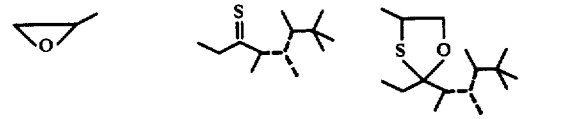 | | |
| 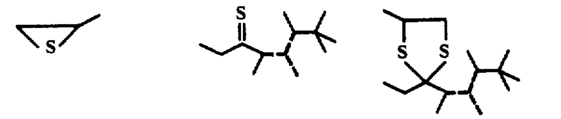 | | |
| 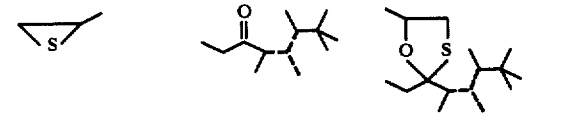 | | |
| 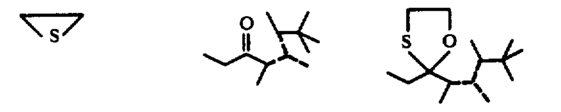 | | |
| 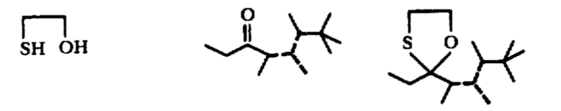 | | |
| 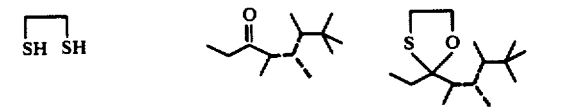 | | |
| 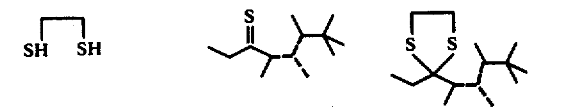 | | |
| 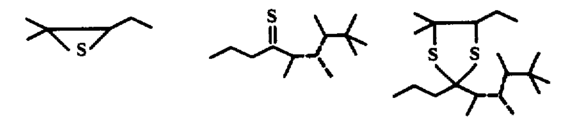 | | |

TABLE I-continued

| Thiirane, Epoxide, Glycol, Thioalcohol or Dithiol Reactant | Acylated or Thioacylated Diisoamylene Reactant | Dioxolane, Dithiolane or Oxathiolane Reaction Product |
|---|---|---|
| 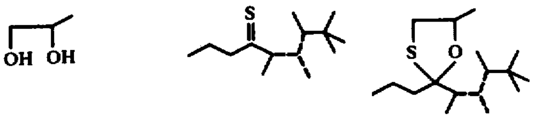 | | |
| 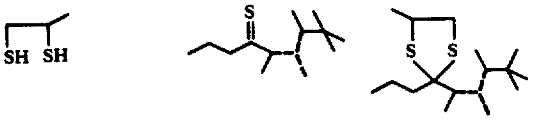 | | |
| 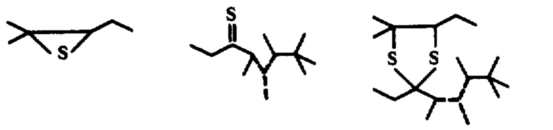 | | |
| 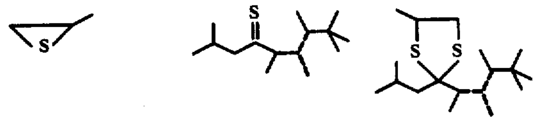 | | |
| 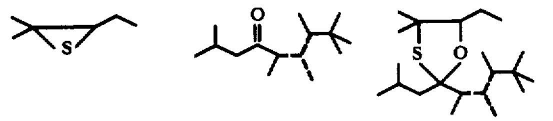 | | |
| 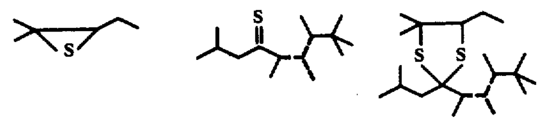 | | |
| 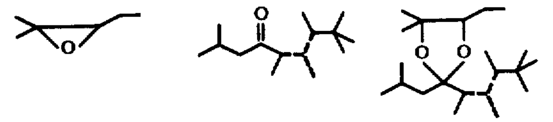 | | |
| 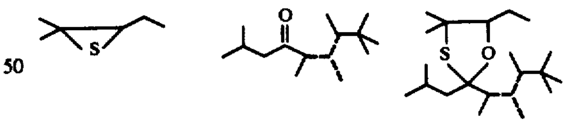 | | |
| 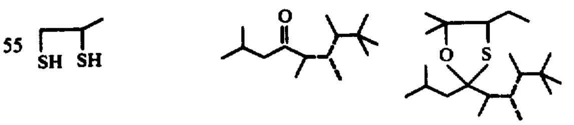 | | |
| 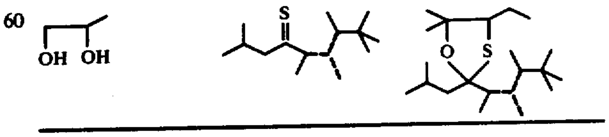 | | |

When a gaseous reactant is used such as thiirane having the structure:

or ethylene oxide having the structure:

the conditions of the reaction involve pressures substantially greater than atmospheric so that the reactant is in constant contact at whatever temperature the reaction is carried out with the other reactant. Thus, when ethylene oxide having the structure:

is reacted with the ketone mixture having the structure:

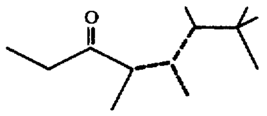

in order to yield the reaction product mixture having the structure:

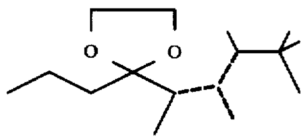

the reaction is preferably carried out at pressures of from about 2 up to about 10 atmospheres and temperatures of from about 50° C. up to about 100° C. in the presence of a Lewis acid such as stannic chloride or boron trifluoride etherate.

The individual oxathiolane, dioxolane, and dithiolane compounds of our invention can be obtained in purer form or in substantially purer form by conventional purification techniques. Thus, the product can be purified and/or isolated by distillation, extraction, crystallization, preparative chromatographic techniques and the like. It has been found desirable to purify the oxathiolane, dithiolane and dioxolane compounds by fractional distillation using vacuum.

It will be appreciated from the present disclosure that the dithiolane, oxathiolane and dioxolane compounds and mixtures thereof according to the present invention can be used to alter, vary, fortify, modify, enhance or otherwise improve the flavor of a wide variety of materials which are ingested, consumed or otherwise organoleptically sensed.

The term "alter" in its various forms will be understood herein to mean the supplying or imparting of a flavor character or note to an otherwise bland, relatively tasteless substance, or augmenting an existing flavor characteristic where the natural flavor is deficient in some regard or supplementing the existing flavor impression to modify the organoleptic character.

Such compounds are accordingly useful in flavoring compositions. A flavoring composition is taken to mean one which contributes a part of the overall flavor impression by supplementing or fortifying a natural or artificial flavor in a material or one which supplies substantially all the flavor and/or aroma character to a consumable article.

The term "enhance" is intended herein to mean the intensification of a particular aroma or taste nuance without changing the quality or nature of said nuance and without adding an additional aroma or taste nuance to the consumable material, the organoleptic properties of which are enhanced.

The term "foodstuff" as used herein includes both solid and liquid ingestable materials for man or animals which materials do, but need not, have nutritional value. Thus, foodstuffs include meats, gravies, soups, convenience foods, malt, alcoholic and other beverages, mild and dairy products, seafoods including fish, crustaceans, mollusks and the like, candies, vegetables, cereals, soft drinks, snacks, dog and cat foods, other veterinary products and the like.

As used herein, the term "medicinal product" includes both solids and liquids which are ingestible nontoxic materials which have medicinal value such as cough syrups, cough drops, aspirin and chewable medicinal tablets.

The term "chewing gum" is intended to mean a composition which comprises a substantially water-insoluble, chewable plastic gum base such as chicle, or substitutes therefor, including jelutong, guttakay, rubber or certain cosmetible natural or synthetic resins or waxes. Incorporated with the gum base in admixture therewith may be plasticizers or softening agents, e.g., glycerine; and a flavoring composition which incorporates one of the oxathiolanes, dithiolanes and dioxolanes of our invention, and in addition, sweetening agents which may be sugars, including sucrose or dextrose and/or artificial sweeteners such as cyclamates or saccharin. Other optional ingredients may also be present.

Substances suitable for use herein as co-ingredients or flavoring adjuvants are well known in the art for such use, being extensively described in the relevant literature. It is a requirement that any such material be "ingestibly" acceptable and thus non-toxic and otherwise non-deleterious particularly from an organoleptic standpoint whereby the ultimate flavor and/or aroma of the consumable material used is not caused to have unacceptable aroma and taste nuances. Such materials may in general be characterized as flavoring adjuvants or vehicles comprising broadly stabilizers, thickeners, surface active agents, conditioners, other flavorants and flavor intensifiers.

Stabilizer compounds include preservatives, e.g. sodium chloride, antioxidants, e.g., calcium and sodium ascorbate, ascorbid acid, butylated hydroxyanisole (mixture of 2- and 3-tertiary-butyl-4-hydroxyanisole), butylated hydroxytoluene (2,6-di-tertiary-butyl-4-methylphenol), propyl gallate and the like and sequestrants, e.g., citric acid.

Thickener compounds include carriers, binders, protective colloids, suspending agents, emulsifiers and the like, e.g., agar agar, carrageenan, cellulose and cellulose derivatives such as carboxymethyl cellulose and methyl cellulose; natural and synthetic gums such as gum arabic, gum tragacanth; gelatin, proteinaceous materials;

lipids; carbohydrates; starches, pectins and emulsifiers, e.g., mono and diglycerides of fatty acids, skim milk powder, hexoses, pentoses, disaccharides, e.g., sucrose, corn syrup and the like.

Surface active agents include emulsifying agents, e.g., fatty acids such as capric acid, caprylic acid, palmitic acid, myristic acid and the like, mono and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like; colorants, e.g., carminic acid, cochineal, tumeric and curcuma and the like; firming agents such as aluminum sodium sulfate, calcium chloride and calcium gluconate; texturizers, anti-caking agents, e.g., aluminum calcium sulfate and tribasic calcium phosphate; enzymes; yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include aldehydes, esters, natural oils, alcohols, sulfides, ketones, lactones, carboxylic acids and hydrocarbons such as heliotropin, terpineol-4, benzaldehyde, anisaldehyde, phenyl acetaldehyde, benzyl formate, benzyl acetate, cis-3-hexenyl benzoate, methyl hexanoate, hexanal, eucalyptol, eugenol, acetaldehyde, ethyl acetate, ethyl butyrate, turpentine gum oil, limonene, gum camphor, isobornyl acetate, borneol, cinnamic aldehyde, cuminic aldehyde, furfural, methyl cinnamate, cassia oil, vanillin, maltol, parahydroxybenzyl acetone, dimethyl sulfide, alpha-ionone, acetic acid, isobutyl acetate, acetone butyric acid, formic acid, valeric acid, amyl acetate, amyl butyrate, anethol, benzyl salicylate, diacetyl, dimethyl anthranilate, ethyl methylphenylglycidate, ethyl succinate, ethyl valerate, geraniol, cis-3-hexen-1-ol, 2-hexenyl acetate, 2-hexenyl butyrate, 4-(p-hydroxyphenyl)-2-butanone, betaionone, isobutyl cinnamate, jasmine, lemon essential oil, methyl butyrate, methyl caproate, methyl disolfide, methyl p-naphthyl ketone, orris butter, rose absolute, terpenyl acetate, gammaundecalactone, vanilla and alcohol.

The specific flavoring adjuvant selected for use may be either solid or liquid depending upon the desired physical form of the ultimate product, i.e., foodstuff, wherher simulated or natural, should, in any event, (i) be organoleptically compatible with the oxathiolanes, dithiolanes and dioxolane derivatives of our invention by not covering or spoiling the organoleptic properties (aroma and/or taste) thereof; (ii) be nonreactive with the oxathiolanes, dithiolanes or dioxolane derivatives of our invention and (iii) be capable of providing an environment in which the oxathiolanes, dithiolanes or dioxolane derivatives can be dispersed or admixed to provide homogeneous medium. In addition, selection of onr or more flavoring adjuvants, as well as the quantities thereof will depend upon the precise organoleptic character desired in the finished product. Thus, in the case of flavoring compositions, ingredient selection will vary in accordance with the foodstuff, chewing gum, medicinal product or toothpaste to which the flavor and/or aroma are to be imparted, modified, altered or enhanced. In contradistinction, in the preparation of solid products, e.g., simulated foodstuffs, ingredients capable of providing normally solid compositions should be selected such as various cellulose derivatives.

As will be appreciated by those skilled in the art, the amount of oxathiolanes, dithiolanes or dioxolanes employed in a particular instance can vary over a relatively wide range, depending upon the desired organoleptic effects to be achieved. Thus, correspondingly greater amounts would be necessary in those instances wherein the ultimate food composition to be flavored is relatively bland to the taste, whereas relatively minor quantities may suffice for purposes of enhancing the composition merely deficient in natural flavor or aroma. The primary requirement is that the amount selected to be effective, i.e., sufficient to alter, modify or enhance the organoleptic characteristics of the parent composition, whether foodstuff per se, chewing gum per se, medicinal product per se, toothpaste per se, or flavoring composition.

The use of insufficient quantities of oxathiolanes, dithiolanes and dioxolane derivatives ranging from small, but effective, amount, e.g., 0.05 ppm up to about 10 ppm will, of course, substantially vitiate any possibility of obtaining the desired results while excess quantities prove needlessly costly and, in extreme cases, may disrupt the flavor-aroma balance, thus proving self defeating. Accordingly, the terminology "effective amount" and "sufficient amount" is to be accorded a significance in the context of the present invention consistent with the obtention of desired flavoring effects.

Thus, and with respect to ultimate food compositions, chewing gum compositions, medicinal product compositions and toothpaste compositions, it is found that quantities of oxathiolanes, dithiolanes and dioxolanes ranging from a small, but effective amount, e.g., 0.05 ppm up to about 100 ppm based on total composition are suitable. Concentrations in excess of the maximum quantity stated are not normally recommended, since they fail to prove commensurate enhancement of organoleptic properties. In those instances, wherein the oxathiolanes, dithiolanes and dioxolanes are added to the foodstuff as an integral component of a flavoring cmposition, it is, of course, essential that the total quantity of flavoring composition employed be sufficient to yield an effective oxathiolane, dithiolane and dioxolanes concentration in the foodstuff product.

Food flavoring compositions prepared in accordance with the present invention preferably contain the oxathiolanes, dithiolanes and dioxolanes in concentrations ranging from about 0.1% up to about 15% by weight based on the total weight of the said flavoring composition.

The composition described herein can be prepared according to conventional techniques well known as typified by cake batters and fruit drinks and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing the oxathiolanes, dithiolanes and dioxolanes with, for example, gum arabic, gum tragacanth, carrageenan and the like, and thereafter spray-drying the resultant mixture whereby to obtain the particular solid product. Pre-prepared flavor mixes in powder form, e.g., a fruit-flavored powder mix are obtained by mixing the dried solid components, e.g., starch, sugar and the like and the oxathiolanes, dithiolanes and dioxolanes in a dry blender until the requisite degree of uniformity is achieved.

It is presently preferred to combine with the oxathiolanes, dithiolanes and dioxolanes of our invention, the following adjuvants:

Heliotropin;
Terpineol-4;
Benzaldehyde;
Anisaldehyde;
Phenyl acetaldehyde;
Benzyl formate;
Benzyl acetate;
Cis-3-hexenyl benzoate;
Methyl Hexanoate;
Hexanal;
Eucalyptol;
Eugenol;
Acetaldehyde;
Ethyl acetate;
Ethyl butyrate;
Turpentine gum oil;
Limonene;
Gum camphor;
Isobornyl acetate;
Borneol;
Cinnamic aldehyde;
Cuminic aldehyde;
Furfural;
Methyl cinnamate;
Cassia oil;
Vanillin;
Maltol;
Parahydroxybenzylacetone;
Dimethyl sulfide;
Alpha-ionone;
Acetic acid;
Isobutyl acetate;
Acetone;
Butyric acid;
Formic acid;
Valeric acid;
Amyl acetate;
Amyl butyrate;
Anethol;
Benzyl salicylate;
Diacetyl;
Dimethyl anthranilate;
Ethyl methylphenylglycidate;
Ethyl succinate;
Ethyl valerate;
Geraniol;
Cis-3-hexen-1-ol;
2-Hexenyl acetate;
2-Hexenyl butyrate;
Hexyl butyrate;
4-(p-Hydroxyphenyl)-2-butanone;
Beta-ionone;
Isobutyl cinnamate;
Jasmine;
Lemon essential oil;
Methyl butyrate;
Methyl capronate;
Methyl disulfide;
Methyl p-naphthyl ketone;
Orris butter;
Rose absolute;
Terpenyl acetate;
Gamma-undecalactone;
Vanilla; and
Alcohol.

An additional aspect of our invention provides an organoleptically improved smoking tobacco product and additives therefor, as well as methods of making the same which overcome problems heretofore encountered in which specific desired sweet, woody, oriental, spicy and fruity flavor characteristics of natural "Turkish-like" tobacco (prior to smoking and on smoking in the mainstream and in the sidestream) are created or enhanced or modified or augmented and may be readily controlled and maintained at the desired uniform level regardless of variations in the tobacco components of the blend.

This invention further provides improved tobacco additives and methods whereby various desirable natural aromatic tobacco flavoring characteristics with sweet, woody, oriental type, camphoraceous, fruity and spicy, as well as peppery taste and aroma nuances may be imparted to smoking tobacco products, and may be readily varied and controlled to produce the desired uniform flavoring characteristics.

In carrying out this aspect of our invention, we add to smoking tobacco materials or a suitable substitute therefor e.g., dried lettuce leaves, an aroma and flavor additive containing as an active ingredient one or more oxathiolanes, dithiolanes and dioxolanes of our invention.

In addition to the oxathiolanes, dithiolanes and dioxolanes of our invention other flavoring and aroma additives may be added to the smoking tobacco material or substitute therefor either separately or in mixture with the oxathiolanes, dithiolanes and dioxolanes as follows:

I. Synthetic Materials

Beta-ethyl-cinnamaldehyde;
Eugenol;
Dipentene;
Damascenone;
Maltol;
Ethyl maltol;
Delta undecalactone;
Delta decalactone;
Benzaldehyde;
Amyl acetate;
Ethyl butyrate;
Ethyl valerate;
Ethyl acetate;
2-Hexenol-1;
2-Methyl-5-isopropyl-1,3-nonadiene-8-one;
2,6-Dimethyl-2,6-undecadiene-10-one;
2-Methyl-5-isopropylacetophenone;
2-Hydroxy-2,5,5,8*a*-tetramethyl-1-(2-hydroxyethyl)-decahydronaphthalene;
Dodecahydro-3*a*6,6,9*a*-tetramethyl-naphtho-(2,1 furan
4-Hydroxyhexanoic acid, gamma lactone; and
Polyisoprenoid hydrocarbons defined in Example V of U.S. Pat. No. 3,589,372 issued on June 29, 1971.

II. Natural Oils

Celery seed oil;
Coffee extract;
Bergamot Oil;
Cocoa extract;
Nutmeg Oil; and
Origanum oil.

An aroma and flavoring concentrate containing one or more oxathiolanes, dithiolanes and dioxolanes of our invention and, if desired, one or more of the above indicated additional flavoring additives may be added to the smoking tobacco material, to the filter or to the leaf or paper wrapper. The smoking tobacco material may be shredded, cured, cased and blended tobacco material or tobacco substitutes (e.g., lettuce leaves) or mixtures thereof. The proportions of flavoring additives may be varied in accordance with taste but insofar as enhancement or the imparting of natural and/or sweet notes and/or woody notes and/or oriental-like notes and/or camphoraceous notes and/or fruity notes and/or spicy notes and/or peppery notes, we have found that satisfactory results are obtained in the proportion by weight of the sum total of oxathiolanes, dithiolanes and dioxolane derivative(s) to smoking tobacco material is between 50 ppm and 1,500 ppm (0.015%-0.15%). We have further found that satisfactory results are obtained if the proportion by weight of the sum total of oxathiolanes, dithiolanes and dioxolane derivatives used to flavoring material is between 1,500 and 15,000 ppm (0.15%-1.5%).

Any convenient method for incorporating the oxathiolanes, dithiolanes and dioxolane derivative(s) into the tobacco product may be employed. Thus, the oxathiolanes, dithiolanes and dioxolane derivative(s) taken alone or along with other flavoring additives may be dissolved in a suitable solvent such as ethanol, diethyl ether and/or volatile organic solvents and the resulting solution may either be spread on the cured, cased and blended tobacco material or the tobacco material may be dipped into such solution. Under certain circumstances, a solution of the oxathiolanes, dithiolanes and dioxolane derivative(s) taken alone or taken further together with other flavoring additives as set forth above, may be applied by means of a suitable applicator such as a brush or roller on the paper or leaf wrapper for the smoking product, or it may be applied to the filter by either spraying or dipping, or coating.

Furthermore, it will be apparent that only a portion of the tobacco or substitute therefor need be treated and the thus treated tobacco may be blended with other tobaccos before the ultimate tobacco product is formed. In such cases, the tobacco treated may have the oxathiolanes, dithiolanes and dioxolane derivative(s) in excess of the amounts or concentrations above indicated so that when blended with other tobaccos, the final product will have the percentage within the indicated range.

In accordance with one specific example of our invention, an aged, cured and shredded domestic burley tobacco is sprayed with a 20% ethyl alcohol solution of the compound having the structure:

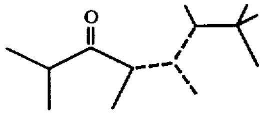

in an amount to provide a tobacco composition containing 800 ppm by weight of said compound on a dry basis. Thereafter, the alcohol is removed by evaporation and the tobacco is manufactured into cigarettes by the usual techniques. The cigarette, when treated as indicated has a desired and pleasing aroma which is defined as woody and peppery with oriental and fruity and spicy undertones detectable in the main and the sidestreams when the cigarette is smoked. This aroma is described as being sweeter, more aromatic, more Turkish tobacco-like and having sweet, fruity, peppery, woody and oriental nuances which cause the burley tobacco to equate Turkish-like.

While our invention is particularly useful in the manufacture of smoking tobacco, such as cigarette tobacco, cigar tobacco and pipe tobacco, other tobacco products, formed from the sheeted tobacco dust or fines may also be used. Likewise, the oxathiolanes, dithiolanes and dioxolane derivative(s) of our invention can be incorporated with materials such as filter tip materials (e.g., cellulose acetate filters wherein sweet, woody, oriental, spicy and/or fruity effects are desired), seam paste, packaging materials and the like which are used along with tobacco to form a product adapted for smoking. Furthermore, the oxathiolanes, dithiolanes and dioxolane derivative(s) can be added to certain tobacco substitutes of natural or synthetic origin (e.g., dried lettuce leaves) and, accordingly, by the term "tobacco" as used throughout this specification is meant any composition intended for human consumption by smoking or otherwise, whether composed of tobacco, of tobacco plant parts, or substitute materials, or both.

The oxathiolanes, dithiolanes and dioxolane derivative(s) of our invention and one or more auxiliary perfume ingredients including, for example, hydrocarbons, alcohols, ketones, aldehydes, nitriles, esters, lactones, synthetic essential oils and/or natural essential oils may be admixed so that the combined odors of the individual components produce a pleasant and desired fragrance, particularly and preferably in the woody, patchouli-like, amber and/or cedarwood fragrances. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low-boiling fresh-smelling materials.

In perfume compositions, it is the individual components which contribute to their particular olfactory characteristics, however, the overall sensory effect of the perfume composition will be at least the sum total of the effects of each of the ingredients. Thus, one or more of the oxathiolanes, dithiolanes and dioxolane derivative(s) of our invention can be used to alter, modify or enhance the aroma characteristics of a perfume composition, for example, by utilizing or moderating the olfactory reaction contributed by another ingredient in the composition.

The amount of oxathiolane, dithiolane and dioxolane derivative(s) of our invention which will be effective in perfume compositions as well as in perfumed articles and colognes depends on many factors, including the other ingredients, their amounts and the effects which are desired. It has been found that perfume compositions containing as little as 0.01% of oxathiolane, dithiolane and/or dioxolane derivative(s) or even less (e.g., 0.005%) can be used to impart pleasant cedar, amber, woody, sweet patchouli-like aromas to soaps, cosmetics, detergents (including solid or liquid anionic, cationic, nonionic and switterionic detergents) or other products. The amount employed can range up to 70% of the fragrance components and will depend on considerations of cost, nature of the end product, the effect desired on the finished product and the particular fragrance sought.

The oxathiolane, dithiolane and dioxolane derivative(s) of our invention are useful (taken alone or together with other ingredients in perfume compositions) in detergents and soaps, space odorants and deodorants, perfumes, colognes, toilet water, bath preparations, such as lacquers, brilliantines, pomades and shampoos; cosmetic preparations such as creams, deodorants, hand lotions and sun screens; powders such as talcs, dusting powders, face powders and the like. As little as 0.05% of the oxathiolane, dithiolane and/or dioxolane derivative(s) will suffice to impart a pleasant cedar, amber, sweet, patchouli-like aroma to perfumed articles which are desired to have a woody aroma. Generally no more than 3% of the oxathiolane, dithiolane and/or dioxolane derivative(s) based on the ultimate end product (e.g., the perfumed article) is required.

In addition, the perfume composition or fragrance composition of our invention can contain a vehicle or carrier for the oxathiolane, dithiolane and/or dioxolane derivative(s). The vehicle can be a liquid such as a non-toxic alcohol, a non-toxic glycol or the like. The carrier can also be an absorbent solid, such as a gum (e.g., gum arabic), or components for encapsulating the composition (such as gelatin).

It will thus be apparent that the oxathiolane, dithiolane and dioxolane derivative(s) of our invention can be utilized to alter, modify or enhance sensory properties, particularly organoleptic properties such as flavor(s) and/or fragrance(s) of a wide variety of consumable materials.

The following Example A sets forth procedures for preparing precursors of the unsaturated branched ketone precursors which are useful in producing the oxathiolanes, dithiolanes and dioxolanes of our invention.

The following Examples I-VIII set forth procedures for preparing the unsaturated branched-chain ketone precursors of the dioxolanes, oxathiolanes and dithiolanes of our invention.

The following Examples IX and X set forth procedures for preparing dioxolanes of our invention.

The remainder of the examples set forth the uses of the oxathiolanes, dioxolanes and dithiolanes of our invention for their organoleptic properties.

It will be understood that these examples are illustrative and that the invention is to be considered restricted thereto only as indicated in the appended claims.

All parts and percentages given herein are by weight unless otherwise specified.

EXAMPLE A

PREPARATION OF DI-ISOAMYLENE DERIVATIVES

Reaction:

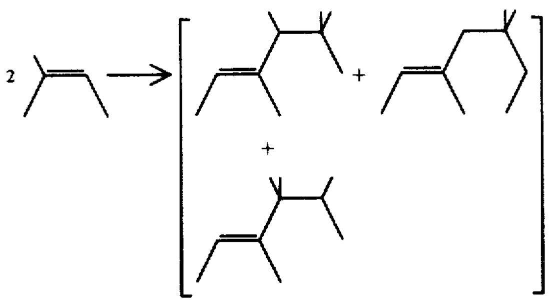

(wherein in each of the molecules indicated, one of the dashed lines is a carbon-carbon double bond and the other of the dashed lines are carbon-carbon single bonds).

Di-isoamylene is prepared according to one of the procedures set forth in the following references:

i-Murphy & Lane, Ind. Eng. Chem., Prod. Res. Dev., Vol. 14, No. 3, 1975 p. 167 (Title: Oligomerization of 2-Methyl-2-Butene in Sulfuric and Sulfuric-Phosphoric Acid Mixtures).

ii-Whitmore & Mosher, Vol. 68, J. Am. Chem. Soc., February, 1946, p. 281 (Title: The Depolymerization of 3,4,5,5-Tetramethyl-2-hexene and 3,5,5-Trimethyl-2-heptene in Relation to the Dimerization of Isoamylenes).

iii-Whitmore & Stahly, Vol. 67, J. Am. Chem. Soc., December, 1945, p. 2158 (Title: The Polymerization of Olefins. VIII The Depolymerization of Olefins in Relation to Intramolecular Rearrangements. II).

iv-U.S. Pat. No. 3,627,700, issued on Dec. 14, 1971, (Zuech).

v-U.S. Pat. No. 3,538,181, issued on Nov. 3, 1970, (Banks).

vi-U.S. Pat. No. 3,461,184, issued on Aug. 12, 1969 (Hay et al).

vii-Gurwitsch, Chemische Berichte, 1912, Vol. 2, p. 796 (Production of Di-isoamylene From Isoamylene Using Mercury Acetate Catalyst).

As an illustration, and not by way of limitation, the following example sets forth the preparation of diisoamylenes useful in producing the unsaturated branched-chain ketones which are useful in producing the fragrances, foodstuff flavor formulations, other flavor formulation and aromatized tobaccos of our invention.

EXAMPLE A-1

Over a period of ten hours, 2-methyl-2-butene is pumped through a 5'×5/8 (0.625 inch) tube packed with 15.0 g of polystyrene sulfonic acid catalyst, at a temperature of 100° C. and at a pressure of 400 psig.

The resulting material was distilled in a fractionation column in order to separate the diisoamylene from the higher molecular weight polymers which are formed during the reaction as by-products. This material distills at 36°-40° C. vapor temperature; 74°-94° C. liquid temperature and 4-5 mm/Hg pressure. This material will be used in the syntheses in the following examples.

FIG. AA represents the GLC profile for the reaction product of Example A using a 70% sulfuric acid catalyst at 35%C.

FIG. AB represents the GLC profile for the reaction product of Example A using an Amberlyst® 15 acidic ion exchange resin catalyst at a temperature of 150° C.

FIG. AC represents the GLC profile for the reaction product of Example A, using an Amberlyst® 15 catalyst at 100° C.

FIG. AD represents the GLC profile for the reaction product of Example A, using a sulfuric acid catalyst and an alpha-methylstyrene diluent at 35° C. according to the conditions of United Kingdom Patent Specification 796,130 (crude reaction product).

FIG. AE represents the GLC profile for the reaction product of Example I, using a sulfuric acid catalyst, at 35° C. and an alpha-methyl styrene diluent according to the conditions of United Kingdom Patent Specification 796,130 (distilled reaction product). Distillation range: 36°-40° C. vapor temperature; 74°-94° C. liquid temperature and 4-5 mm/Hg pressure.

FIG. BA represents the NMR spectrum for Peak 1 of the GLC profile of FIG. AE.

FIG. BB represents the infra-red spectrum for Peak 1 of the GLC profile of FIG. AE.

FIG. CA represents the NMR spectrum for Peak 2 of the GLC profile of FIG. AE.

FIG. CB represents the infra-red spectrum for Peak 2 of the GLC profile of FIG. AE.

FIG. D represents the NMR spectrum for Peak 2 of the GLC profile of FIG. AB.

EXAMPLE I

PREPARATION OF ACETYL DERIVATIVE OF DIISOAMYLENE

Reaction:

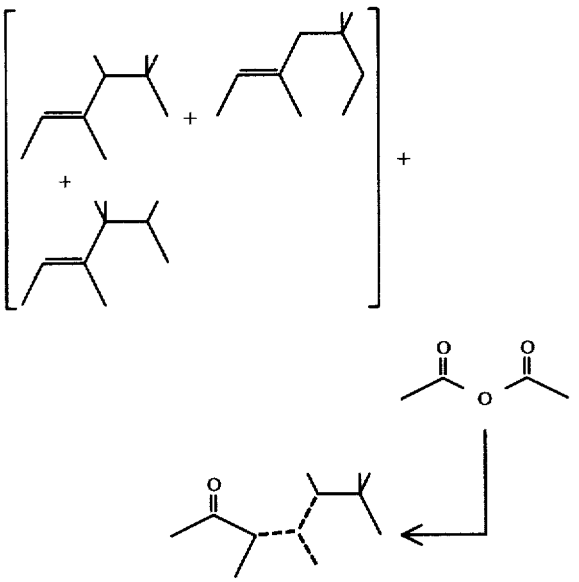

wherein in each of the structures containing dashed lines, these structures represent mixtures of molecules wherein in each of the molecules, one of the dashed lines represents a carbon-carbon double bond and each of the other of the dashed lines represent carbon-carbon single bonds.

Into a 2-liter reaction flask equipped with stirrer, thermometer, reflex condenser and heating mantle, is placed 1000 g of acetic anhydride and 80 g of boron trifluoride diethyl etherate. The resulting mixture is heated to 80° C. and, over a period of 40 minutes, 690 g of diisoamylene prepared according to the illustration in Example A-1, supra is added. The reaction mass is maintained at 82°-85° C. for a period of 5.5 hours, whereupon it is cooled to room temperature. The reaction mass is then added to one liter of water and the resulting mixture is stirred thereby yielding two phases; an organic phase and an aqueous phase. The organic phase is separated from the aqueous phase and neutralized with two liters of 12.5% sodium hydroxide followed by one liter of saturated sodium chloride solution. The resulting organic phase is then dried over anhydrous sodium sulfate and distilled in a one plate distillation column, yielding the following fractions:

| Fraction No. | Vapor Temp. (°C.) | Liquid Temp. (°C.) | mm/Hg Pressure | Weight of Fraction (g.) |
|---|---|---|---|---|
| 1 | 33/68 | 62/77 | 8/8 | 161 |
| 2 | 69 | 79 | 4 | 100 |
| 3 | 72 | 86 | 3.0 | 191 |
| 4 | 88 | 134 | 3.0 | 189 |

The resulting material is then distilled on a multi-plate fractionation column, yielding the following fractions at the following reflux ratios:

| Fraction No. | Vapor Temp. (°C.) | Liquid Temp. (°C.) | mm/Hg Pressure | Reflux Ratio R/D | Weight of Fraction (g.) |
|---|---|---|---|---|---|
| 1 | 30/65 | 62/83 | 5/5 | 9:1 | 30.8 |
| 2 | 68 | 84 | 5 | 9:1 | 52.8 |
| 3 | 68 | 85 | 5 | 9:1 | 34 |
| 4 | 69 | 87 | 5 | 9:1 | 43 |
| 5 | 69 | 87 | 5 | 9:1 | 34 |
| 6 | 71 | 88 | 4 | 4:1 | 41 |
| 7 | 70 | 88 | 5 | 4:1 | 36.5 |
| 8 | 71 | 91 | 5 | 4:1 | 42 |
| 9 | 73 | 95 | 3 | 4:1 | 42.5 |
| 10 | 80 | 106 | 3 | 4:1 | 39 |
| 11 | 80 | 142 | 3 | 4:1 | 50.8 |
| 12 | 80 | 220 | 3 | 4:1 | 24 |

Fractions 5-9 of the above distillation are bulked and are utilized in the following examples as a reactant.

GLC, NMR, IR and mass spectral analyses yield the information that the resulting material is a mixture of cis and trans isomers having a generic structure:

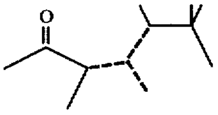

wherein in each of the molecules, one of the dashed lines is a carbon-carbon double bond and the other of the dashed lines is a carbon-carbon single bond and, primarily, this mixture contains the molecular species (cis and trans isomers) as follows:

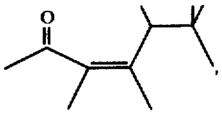
,
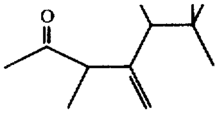
and

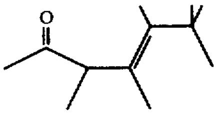

FIG. 1 sets forth the GLC profile for the reaction product of Example I, containing compounds defined according to the structure:

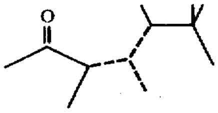

wherein in each molecule of the mixture, one of the dashed lines is a carbon-carbon double bond and the other of the dashed lines are carbon-carbon single bonds.

FIG. 2A represents the infra-red spectrum of Peak 3 of the GLC profile of FIG. 1.

FIG. 2B represents the infra-red spectrum of Peak 4 of the GLC profile of FIG. 1.

FIG. 2C represents the infra-red spectrum for Peak 5 of the GLC profile of FIG. 1.

FIG. 2D represents the infra-red spectrum for Peak 6 of the GLC profile of FIG. 1.

FIG. 2E represents the infra-red spectrum for Peak 7 of the GLC profile of FIG. 1.

FIG. 2F represents the infra-red spectrum for Peak 8 of the GLC profile of FIG. 1.

FIG. 2G represents the infra-red spectrum for Peak 9 of the GLC profile of FIG. 1.

FIG. 2H represents the infra-red spectrum for Peak 10 of the GLC profile of FIG. 1.

FIG. 2J represents the NMR spectrum for a mixture of compounds having the structures:

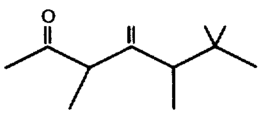

and

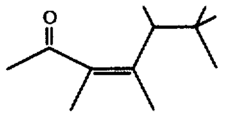

produced according to Example I.

FIG. 2K represents the NMR spectrum for the compound having the structure:

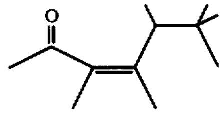

produced according to Example I.

FIG. 2L represents the NMR spectrum for the compound containing the structure:

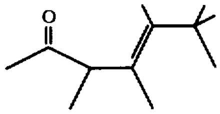

produced according to Example 1.

EXAMPLE II

PREPARATION OF PROPIONYL DERIVATIVE OF DIISOAMYLENES

Reaction:

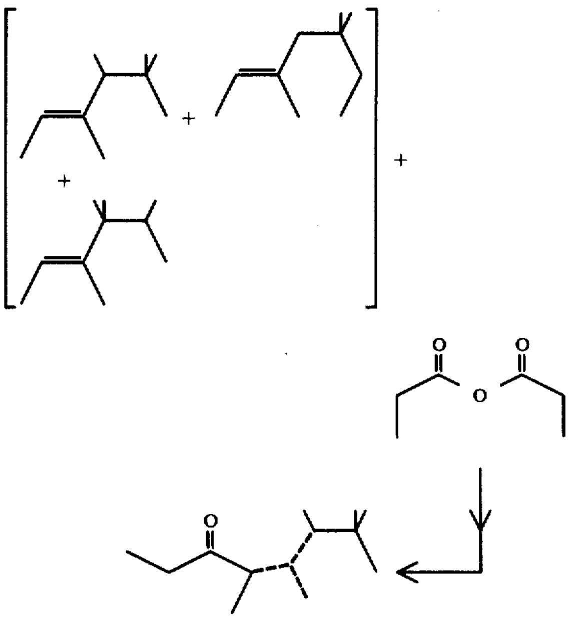

wherein in each of the structures containing dashed lines, these structures represent mixtures of molecules wherein in each of the molecules, one of the dashed lines represents a carbon-carbon double bond and each of the other of the dashed lines represent carbon-carbon single bonds.

Into a 5-liter reaction flask equipped with reflux condenser, addition funnel, thermometer, "Thermowatch", heating mantle and nitrogen purge accessory is placed 1000 g (7.45 moles) of propionic anhydride, 94% and 91.4 ml (0.745 moles) of boron trifluoride etherate. The resulting mixture is heated to 65° C. Over a twenty-five minute period, 1,501 ml (7.45 moles) of the diisoamylene prepared according to the illustration of Example A-1 is added while maintaining the reaction mass at 65°-70° C. The reaction mass is then stirred for a period of thirty minutes at 65° C. whereupon it is cooled and poured into a 3 liter separatory funnel. 75 ml water is then added, followed by 75 ml 50% aqueous sodium hydroxide and another 25 ml water. The reaction mass is then poured into a 4 liter beaker and cooled to room temperature using a dry ice-isopropyl alcohol bath. The reaction mass is then added to a 5-liter separatory funnel and the lower aqueous layer is removed. The upper organic phase is washed with 500 cc of saturated sodium chloride. The organic phase is then washed with 500 cc 5% sodium hydroxide followed by 500 cc saturated sodium chloride, followed by 500 cc of 5% sodium hydroxide. The pH of the oil is now in a range of 6-7. The oil is then again washed with 500 cc saturated sodium chloride.

The aqueous phase is extracted with 400 ml diethyl ether. The resulting material is then distilled on a two inch splash column yielding the following fractions:

| Fraction No. | Vapor Temp. (°C.) | Liquid Temp. (°C.) | mm/Hg Pressure | Weight of Fraction (g.) |
|---|---|---|---|---|
| 1 | 25/75 | 60/85 | 50/50 | 144 |
| 2 | 74 | 87 | 38 | 184 |
| 3 | 34 | 40 | 4 | 186 |

-continued

| Fraction No. | Vapor Temp. (°C.) | Liquid Temp. (°C.) | mm/Hg Pressure | Weight of Fraction (g.) |
|---|---|---|---|---|
| 4 | 55 | 78 | 3 | 212 |
| 5 | 87 | 94 | 3 | 181 |
| 6 | 95 | 114 | 3 | 210 |
| 7 | 170 | 155 | 3 | 80 |
| 8 | 160 | 225 | 3 | 42 |

Fractions 5, 6 and 7 are then bulked for redistillaton and the bulked material is distilled on a one-inch Goodloe Silver Mirror Column, yielding the following fractions:

| Fraction No. | Vapor Temp. (°C.) | Liquid Temp. (°C.) | mm/Hg Pressure | Reflux Ratio R/D | Weight of Fraction (g.) |
|---|---|---|---|---|---|
| 1 | 17/60 | 81/90 | 3/1.4 | 1:4 | 42 |
| 2 | 58 | 89 | 1.0 | 4:1 | 48 |
| 3 | 63 | 93 | 1.0 | 4:1 | 37 |
| 4 | 68 | 94 | 1.0 | 4:1 | 48 |
| 5 | 70 | 94 | 1.0 | 4:1 | 43 |
| 6 | 72 | 95 | 1.8 | 2:1 | 39 |
| 7 | 72 | 94 | 1.7 | 2:1 | 87 |
| 8 | 74 | 108 | 1.6 | 2:1 | 48 |
| 9 | 82 | 135 | 1.6 | 2:1 | 48 |
| 10 | 110 | 220 | 1.0 | 2:1 | 37 |

Fractions 2-10 are then bulked and redistilled on a 1-foot Goodloe Silver Mirror Column, again yielding the following fractions:

| Fraction No. | Vapor Temp. (°C.) | Liquid Temp. (°C.) | mm/Hg Pressure | Reflux Ratio R/D | Weight of Fraction (g.) |
|---|---|---|---|---|---|
| 1 | 52/58 | 83/85 | 1.4/1.2 | 4:1 | 46 |
| 2 | 59 | 86 | 1.1 | 4:1 | 50 |
| 3 | 61 | 89 | 1.1 | 4:1 | 53 |
| 4 | 61 | 89 | .9 | 4:1 | 57 |
| 5 | 61 | 91 | .8 | 4:1 | 44 |
| 6 | 61 | 91 | .8 | 4:1 | 41 |
| 7 | 65 | 101 | .8 | 4:1 | 42 |
| 8 | 68 | 115 | .8 | 4:1 | 49 |
| 9 | 74 | 135 | .8 | 4:1 | 17 |
| 10 | 88 | 230 | .8 | 4:1 | 17 |

Fractions 3-7 of the foregoing distillation are bulked and these fractions are used for subsequent reactions.

The resulting material is analyzed using GLC, IR, mass spectral and NMR analyses, yielding information that the resulting material is a mixture of compounds defined according to the generic structure:

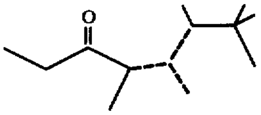

wherein in each molecule of the mixture, one of the dashed lines is a carbon-carbon double bond and each of the other of the dashed lines are carbon-carbon single bonds.

FIG. 3 represents the GLC profile for the reaction product of Example II containing a mixture of compounds, each of which is defined according to the generic structure:

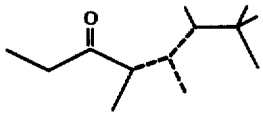

wherein in each molecule one of the dashed lines is a carbon-carbon double bond and each of the other of the dashed lines are carbon-carbon single bonds.

FIG. 4 represents the infra-red spectrum for the product produced according to Example II containing the compounds having the structures:

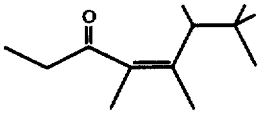

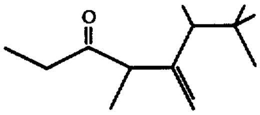

and

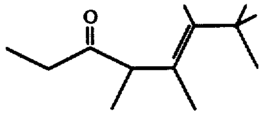

FIG. 5 represents the mass spectrum for the reaction product of Example II, containing the compounds having the structures:

EXAMPLE III

PREPARATION OF n-BUTYRYL DERIVATIVE OF DIISOAMYLENE

Reaction:

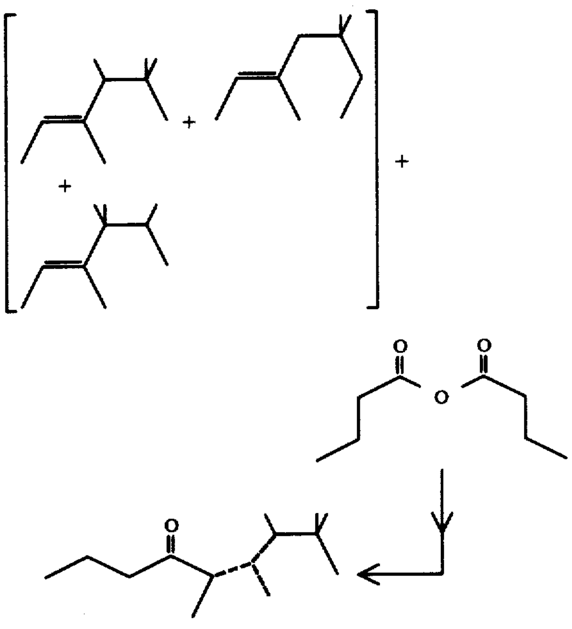

wherein in each of the structures containing dashed lines, these structures represent mixtures of molecules wherein in each of the molecules, one of the dashed lines represents a carbon-carbon double bond and each of the other of the dashed lines represent carbon-carbon single bonds.

Into a 5-liter reaction flask equipped with electric stirrer, heating mantle, thermometer, 24/40 "Y" joint, addition funnel and reflux condenser is added 960 g of n-butyric anhydride, followed by 105 ml boron trifluoride. The resulting mixture is heated to 65° C. and a Thermowatch is attached (reaction must not exceed a pot temperature of 65° C.).

The reaction mass is heated to 65° C. and dropwise addition of 1,725 ml of diisoamylene, prepared according to the illustration of Example A-1 is added over a period of 3.5 hours while maintaining the reaction mass at a temperature of 65° C.

At the end of the addition, the reaction mass is cooled to 38° C. and then transferred to a 5-liter separatory funnel. 75 ml of 50% aqueous sodium hydroxide and 100 ml water are then added to the reaction mass. The reaction mass now exists in two phases; an aqueous phase and an organic phase. The organic phase is washed with one liter of saturated sodium chloride solution thereby creating a pH of 4–5. The reaction mass is then washed with 1-liter of 12.5% sodium hydroxide, stirred for fifteen minutes, and then separated. The resulting organic phase is then dried over anhydrous magnesium sulfate and distilled on a 1-inch Stone column yielding the following fractions:

| Fraction No. | Vapor Temp. (°C.) | Liquid Temp. (°C.) | mm/Hg Pressure |
|---|---|---|---|
| 1 | 40/46 | 63/65 | 30/20 |
| 2 | 66 | 77 | 40 |
| 3 | 66 | 77 | 35 |
| 4 | 66 | 87 | 33 |
| 5 | 69 | 90 | 20 |
| 6 | 64 | 100 | 15 |
| 7 | 95 | 110 | 2 |
| 8 | 97 | 110 | 2 |
| 9 | 125 | 160 | 2 |

The resulting fractions 7, 8 and 9 are bulked and redistilled on a 2 foot stainless steel column yielding the following fractions:

| Fraction No. | Vapor Temp. (°C.) | Liquid Temp. (°C.) | mm/Hg Pressure | Reflux Ratio R/D | Weight of Fraction (g.) |
|---|---|---|---|---|---|
| 1 | 47/74 | | 1.8 | 4:1 | 53 |
| 2 | 74 | 105 | 1.4 | 4:1 | 85 |
| 3 | 74 | 107 | 1.4 | 4:1 | 96 |
| 4 | 74 | 107 | 1.4 | 4:1 | 89 |
| 5 | 70 | 105 | 1.0 | 4:1 | 66 |
| 6 | 75 | 110 | 1.0 | 4:1 | 44 |
| 7 | 84 | 165 | 1.0 | 4:1 | 66 |
| 8 | 80 | 220 | 1.0 | 4:1 | 12 |

Fractions 3 and 4 of the foregoing distillation are bulked for use as reactants in subsequent examples.

FIG. 6 represents the GLC profile for the reaction product of Example III containing compounds defined according to the generic structure:

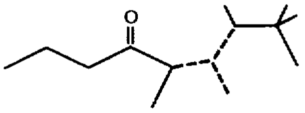

wherein in each of the molecule of the mixture, one of the dashed lines represents a carbon-carbon double bond and the other of the dashed lines represents carbon-carbon single bonds.

FIG. 7 represents the infra-red spectrum for the reaction product of Example III containing the compounds having the structures:

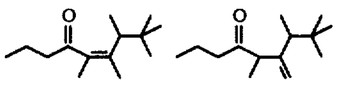

and

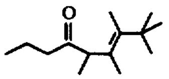

FIG. 8 represents the mass spectrum for the reaction product of Example III containing the compound having the structures:

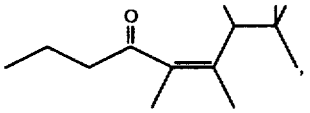

,

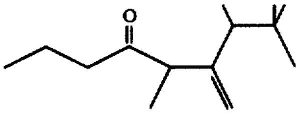

and

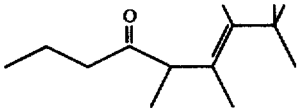

EXAMPLE IV

PREPARATION OF ISOBUTYRYL DERIVATIVE OF DIISOAMYLENE

Reaction:

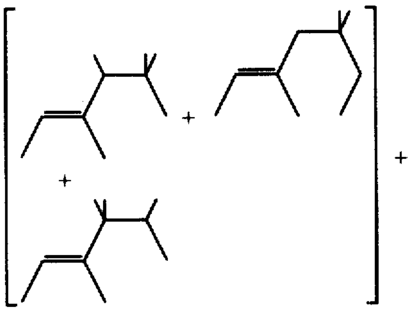

-continued

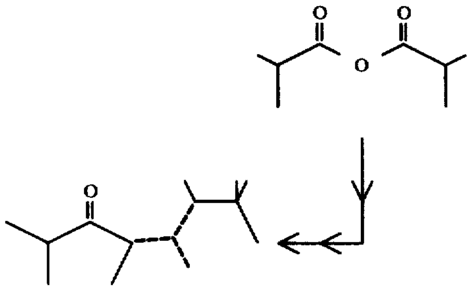

wherein in each of the structures containing dashed lines, these structures represent mixtures of molecules wherein in each of the molecules, one of the dashed lines represents a carbon-carbon double bond and each of the other of the dashed lines represent carbon-carbon single bonds.

Into a 5-liter reaction flask, equipped with reflux condenser, addition funnel, thermometer, Thermowatch, heating mantle and nitrogen purge accessory is placed 1361 g (8.6 moles) of isobutyric anhydride. 105 ml (0.86 moles) of boron trifluoride etherate is then added to the isobutyric anhydride. The resulting mixture is then heated to 65° C. Over a period of 4 hours, 1725 g (8.6 moles) of diisoamylene prepared according to the illustration of Example A-1 is added to the reaction mass, while maintaining the reaction mass at a temperature of 83°-85° C.

The reaction mass is then cooled to room temperature and is added to a 5-liter separatory funnel. 75 ml of 50% sodium hydroxide (aqueous) and 100 ml water is then added to the reaction mass thus yielding two phases, an aqueous phase and an organic phase. The lower aqueous phase is removed and the organic phase is washed as follows:

A—1 liter saturated sodium chloride
B—1 liter 5% aqueous sodium hydroxide
C—1 liter saturated sodium chloride
D—1 liter 12.5% sodium hydroxide
E—1 liter 12.5% sodium hydroxide The reaction mass is then distilled on a two inch splash column packed with stones yielding the following fractions:

| Fraction No. | Vapor Temp. (°C.) | Liquid Temp. (°C.) | mm/Hg mm/Hg Pressure | Weight of Fraction (g.) |
|---|---|---|---|---|
| 1 | 29/54 | 54/68 | 29/24 | Starting Material |
| 2 | 51 | 68 | 14 | " |
| 3 | 90 | 68 | 11 | " |
| 4 | 64 | 98 | 11 | " |
| 5 | 92/94 | 102/108 | 7/5 | 378 |
| 6 | 135 | 165 | 5 | 257 |

Fractions 5 and 6 of the resulting distillate are then bulked and redistilled yielding the following fractions:

| Fraction No. | Vapor Temp. (°C.) | Liquid Temp. (°C.) | mm/Hg Pressure | Reflux Ratio R/D | Weight of Fraction (g.) |
|---|---|---|---|---|---|
| 1 | 15/45 | 88/92 | 3/2.5 | 4:1 | 21 |
| 2 | 60 | 99 | 2.4 | 4:1 | 13 |
| 3 | 67 | 98 | 2.4 | 4:1 | 35 |
| 4 | 69 | 97 | 2.2 | 4:1 | 49 |
| 5 | 70 | 99 | 2.2 | 4:1 | 59 |
| 6 | 70 | 101 | 2.2 | 4:1 | 50 |
| 7 | 70 | 101 | 2.0 | 4:1 | 37 |
| 8 | 84 | 112 | 1.7 | 4:1 | 33 |
| 9 | 84 | 112 | 1.7 | 4:1 | 63 |
| 10 | 78 | 119 | 1.8 | 4:1 | 37 |
| 11 | 84 | 122 | 1.7 | 4:1 | 51 |
| 12 | 92 | 121 | 1.7 | 4:1 | 43 |
| 13 | 101 | 156 | 1.6 | 4:1 | 27 |
| 14 | 121 | 178 | 1.6 | 4:1 | 85 |
| 15 | 110 | 220 | 1.6 | 4:1 | 33 |

Fractions 3-9 of this distillation are then rebulked and redistilled on a 12 inch Goodloe Silver Mirror column yielding the following fractions:

| Fraction No. | Vapor Temp. (°C.) | Liquid Temp. (°C.) | mm/Hg Pressure | Reflux Ratio R/D | Weight of Fraction (g.) |
|---|---|---|---|---|---|
| 1 | 47/60 | 84/92 | 1.6/1.2 | 4:1 | |
| 2 | 67 | 93 | 1.2 | 4:1 | 50 |
| 3 | 67 | 94 | 1.2 | 4:1 | 50 |
| 4 | 67 | 95 | 1.2 | 4:1 | 52 |
| 5 | 67 | 95 | 1.2 | 4:1 | 50 |
| 6 | 67 | 98 | 1.2 | 4:1 | 57 |
| 7 | 67 | 101 | 1.2 | 4:1 | 57 |
| 8 | 72 | 212 | 1.2 | 4:1 | 42 |

Fractions 4-7 of the foregoing distillation are bulked and are utilized as reactants in the following examples.

The resulting reaction product is analyzed by means of GLC, NMR, IR and mass spectral analyses and this confirms that the reaction product is a mixture of compounds defined according to the generic structure:

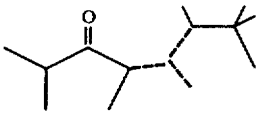

wherein in each of the molecules, one of the dashed lines is a carbon-carbon double bond and the other two of the dashed lines represent carbon-carbon single bonds. The major components of this mixture are compounds having the structures:

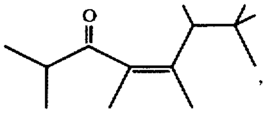
,
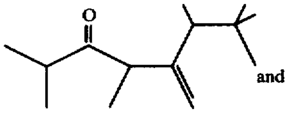
and
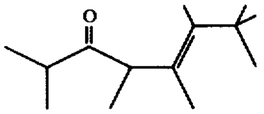

FIG. 9 represents the GLC profile for the reaction product of Example IV, containing a mixture of compounds, each of which is defined according to the generic structure:

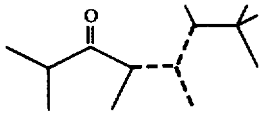

wherein in each of the molecules, one of the dashed lines represents a carbon-carbon double bond and each of the other of the dashed lines represent carbon-carbon single bonds.

FIG. 10 represents the infra-red spectrum for the reaction product of Example IV containing the compounds having the structures:

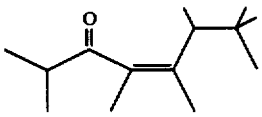 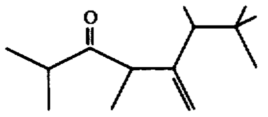

and 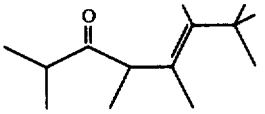

FIG. 11 represents the mass spectrum for the reaction product of Example IV containing the compounds having the structures:

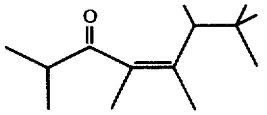 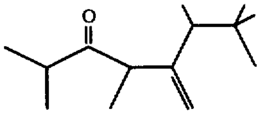

and 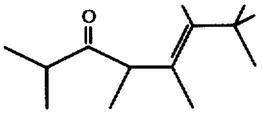

EXAMPLE V

PREPARATION OF ACETYL DERIVATIVE OF DIISOAMYLENE

Reaction:

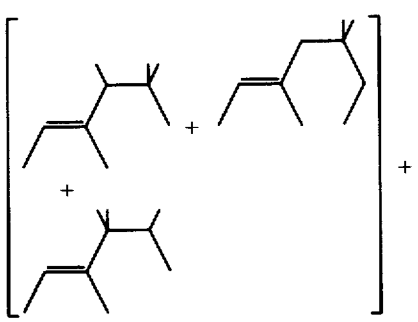

-continued

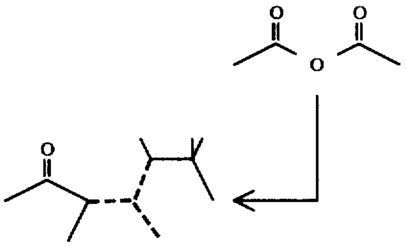

EXAMPLE VA

Into a 5-liter reaction flask equipped with electric stirrer, thermometer, addition funnel, 24/42 y-tube, condenser, heating mantle and nitrogen purge accessories are added 41 ml of 70% methane sulfonic acid followed by 30 g of phosphorous pentoxide. The resulting mixture exotherms to 60° C.

Over a period of 7 minutes, 235 ml acetic anhydride is added to the reaction mass while maintaining same at a temperature of 65° C. Over a period of 30 minutes while maintaining the reaction temperature at 80° C., 516 ml of diisoamylene prepared according to the illustration of Example A-1 is added dropwise to the reaction mass. At the end of the addition of the diisoamylene, GLC analysis indicates 42% product.

The reaction mass is added to a 5 gallon open head separatory flask containing 1 liter of water.

The resulting mixture is washed with 1 liter of 12% sodium hydroxide followed by 1 liter of saturated sodium chloride solution. 100 ml toluene is added to help separation.

GLC, NMR, IR and mass spectral analyses yield the information that the resulting organic phase is a mixture of compounds defined according to the generic structure:

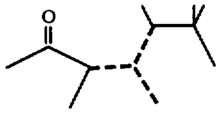

wherein in each of the molecules one of the dashed lines is a carbon-carbon double bond and the other two of the dashed lines represent carbon-carbon single bonds.

The resulting reaction product is then dried over anhydrous magnesium sulfate and distilled on a 3-inch stone column yielding the following fractions:

| Fraction No. | Vapor Temp. (°C.) | Liquid Temp. (°C.) | mm/Hg Pressure |
|---|---|---|---|
| 1 | 65/65 | 103/92 | 113/35 |
| 2 | 60 | 80 | 1 |
| 3 | 52 | 89 | 1 |
| 4 | 61 | 134 | 1 |
| 5 | 73 | 140 | 1 |

Fraction 2, 3 and 4 are bulked and used as reactants in the following examples.

FIG. 12 represents the GLC profile for the reaction product of Example VA containing structures defined according to the genus having the structure:

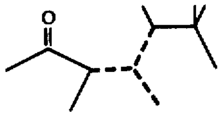

wherein in each of the molecules of the mixture, one of the dashed lines represents a carbon-carbon double bond and each of the other of the dashed lines represent carbon-carbon single bonds.

EXAMPLE VB

To a 500 ml reaction flask equipped with reflux condenser, addition funnel, thermometer, Thermowatch, heating mantle, cooling bath and nitrogne purge accessories, is added 406 ml of acetic anhydride and 30 ml boron trifluoride etherate. The reaction mass is heated to 60° C. and while maintaining the reaction mass at 60° over a period of 30 minutes, diisoamylene, prepared according to the illustration of Example A-1 is added. The resulting reaction mass is then heated, with stirring at 60° C. for a period of 12 hours. At the end of the 12 hour period, the reaction mass is distilled yielding the following fractions:

| Fraction No. | Vapor Temp. (°C.) | Liquid Temp. (°C.) | mm/Hg pressure | Weight of Fraction (g.) |
|---|---|---|---|---|
| 1 | 50/58 | 60/70 | 2.5 | 330 |
| 2 | 67 | 87 | 1.4 | 329 |
| 3 | 71 | 88 | 3.0 | 65 |
| 4 | 90 | 115 | 3.0 | 195 |

Fractions 2 and 3 are bulked for subsequent reaction.

The resulting mass, by GLC, IR, NMR and mass spectral analyses consist of compounds defined according to the generic structure:

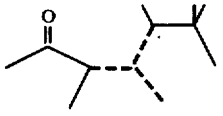

wherein in each of the molecules one of the dashed lines is a carbon-carbon double bond and the other two of the dashed lines represent carbon-carbon single bonds.

FIG. 13 sets forth the GLC profile for the reaction product of this Example VB.

EXAMPLE VI

PREPARATION OF PROPIONYL DERIVATIVE OF DIISOAMYLENE

Reaction:

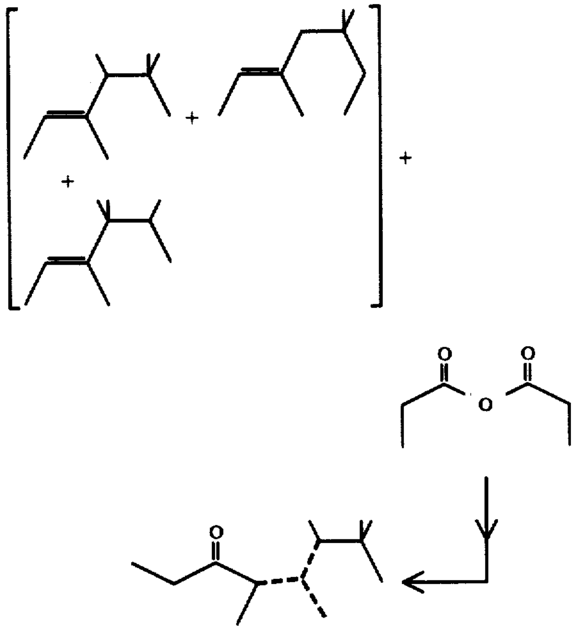

Into 5000 ml reaction flask equipped with reflux condenser, addition funnel, thermometer, Thermowatch, heating mantle, cooling bath and nitrogen purge accessory, is added 415 ml propionic anhydride, 11 g of methane sulfonic acid and 35 ml of boron trifluoride etherate. The reaction mass is heated to 60° C. and over a period of 30 minutes, 1850 ml of diisoamylene prepared according to the illustration of Example A-1 is added. The reaction mass is then stirred at 60° C. for a period of 12 hours. At the end of the 12 hour period, the reaction mass is distilled on a Goodloe fractionation column to yield a mixture of compounds having the generic structure:

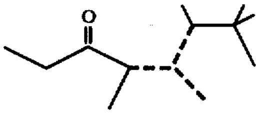

wherein in each of the molecules therein one of the dashed lines represents a carbon-carbon double bond and each of the other of the dashed lines represents a carbon-carbon single bond. The reaction structures are confirmed by GLC, NMR, IR and mass spectral analyses.

The product distills at a vapor temperature of 68°-70° C. and a pressure of 1.0 mm/Hg. This product is utilized as a reactant in the following examples, infra.

EXAMPLE VIIA

PREPARATION OF ISOBUTYRO DERIVATIVE OF DIISOAMYLENE

Reaction:

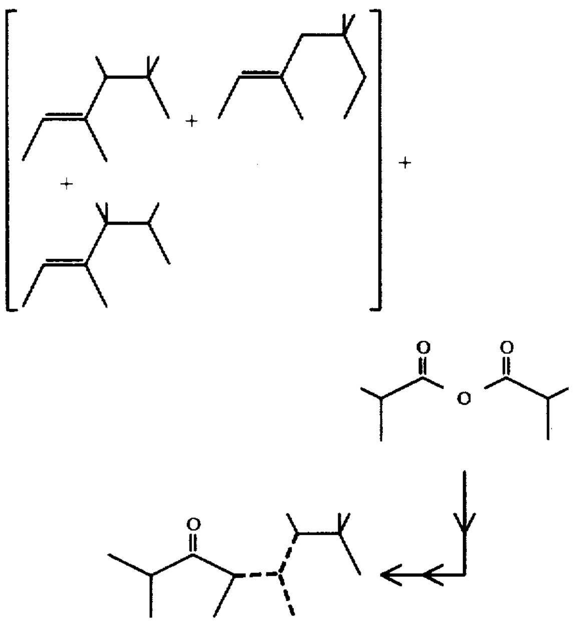

wherein in each of the structures containing dashed lines, these structures represent mixtures of molecules wherein in each of the molecules, one of the dashed lines represents a carbon-carbon double bond and each of the other of the dashed lines represent carbon-carbon single bonds.

Into a 5000 ml reaction flask equipped with reflux condenser, addition funnel, thermometer, Thermowatch, heating mantle, cooling bath and nitrogen gas purge accessory, is added 953 ml (6.0 moles) of isobutyric anhydride; 183 g of polyphosphoric acid and 135 ml 70% methane sulfonic acid. The reaction mass exotherms to 65° C.

Over a period of 20 minutes, while maintaining the reaction mass at 65° C. 1725 g (8.6 moles) of diisoamylene prepared according to the illustration of Example A-1 is added to the reaction mass. The reaction mass is then heated to 85° C. and maintained at that temperature for a period of 10 hours. At the end of the 10 hour period, the reaction mass is cooled and 100 g of sodium acetate and 1 liter of water are added thereto. The resulting mixture is added to a 5 liter separatory funnel and the organic layer is then washed as follows:

A—1 liter 12.5% sodium hydroxide
B—2 liter 12.5% sodium hydroxide
C—1 liter of saturated sodium chloride The reaction mass is then distilled on a 1 foot Goodloe column yielding the following fractions:

| Fraction No. | Vapor Temp. (°C.) | Liquid Temp. (°C.) | mm/Hg Pressure | Reflux Ratio R/D | Weight of Fraction (g.) |
|---|---|---|---|---|---|
| 1 | 35/50 | 88/93 | 1.8/.08 | 4:1 | 41 |
| 2 | 63 | 100 | 0.8 | 4:1 | 48 |
| 3 | 63 | 105 | 0.6 | 4:1 | 73 |
| 4 | 66 | 114 | 0.6 | 4:1 | 44 |
| 5 | 100 | 145 | 0.6 | 4:1 | 42 |
| 6 | 101 | 225 | 0.6 | 4:1 | 29 |

Fractions 3-5 are bulked and the bulking is utilized for subsequent reactions.

GLC, NMR, IR and mass spectral analyses confirm the information that the resulting product is a mixture of compounds defined according to the generic structure:

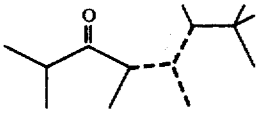

wherein in each molecule of the mixture, one of the dashed lines is a carbon-carbon double bond and the other two of the dashed lines represent carbon-carbon single bonds.

FIG. 14 sets forth the GLC profile for the reaction product of this Example VIIA. (Conditions: SF 96 column, six foot×¼ inch; operated at 180° C. isothermal).

EXAMPLE VIIB

Into a 5000 ml reaction flask equipped with reflux condenser, addition funnel, thermometer, Thermowatch, heating mantle, cooling bath and nitrogen gas purge accessory, is added 953 g (6.0 moles) of isobutyric anhydride and 105 ml (0.86 moles) of boron trifluoride etherate. The reaction mass is heated to 65° C. and over a period of 30 minutes 1725 ml (8.6 moles) of diisoamylene prepared according to the illustration of Example A-1 is added. The reaction mass is then heated to 63°-65° C. and maintained with stirring at that temperature for a period of 12 hours.

The reaction mass is then cooled to room temperature and 82 g of sodium acetate are added. The reaction mass is then poured into a 5 liter separatory funnel and washed as follows:

A—1 liter water
B—1 liter 12.5% aqueous sodium hydroxide
C—1 liter 12.5% aqueous sodium hydroxide
D—1 liter 12.5% aqueous sodium hydroxide
E—1 liter saturated sodium chloride The organic layer is then dried over anhydrous sodium sulfate and distilled on a 12 inch Goodloe column yielding the following fractions:

| Fraction No. | Vapor Temp. (°C.) | Liquid Temp. (°C.) | mm/Hg Pressure | Reflux Ratio R/D | Weight of Fraction (g.) |
|---|---|---|---|---|---|
| 1 | 55/67 | 85/92 | 2.4/1.5 | 4:1 | 50 |
| 2 | 72 | 95 | 1.5 | 4:1 | 72 |
| 3 | 73 | 98 | 1.5 | 4:1 | 83 |
| 4 | 75 | 104 | 1.4 | 4:1 | 69 |
| 5 | 80 | 112 | 1.4 | 4:1 | 69 |
| 6 | 80 | 112 | 1.4 | 4:1 | 12 |
| 7 | 108 | 140 | 1.4 | 2:3 | 69 |
| 8 | 116 | 180 | 1.4 | 2:3 | 61 |
| 9 | 110 | 225 | 1.4 | 2:3 | 9 |

Fractions 4-7 are bulked and the resulting bulked product is utilized for reactions in subsequent examples.

GLC, NMR, IR and mass spectral analyses confirm that the resulting product is a mixture of compounds defined according to the generic structure:

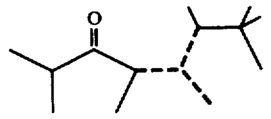

wherein in each of the molecules in the mixture one of the dashed lines represents a carbon-carbon double bond and the other of the dashed lines represent carbon-carbon single bonds.

EXAMPLE VIII

PREPARATION OF n-BUTYRO DIISOAMYLENE AND DERIVATIVES

Reaction:

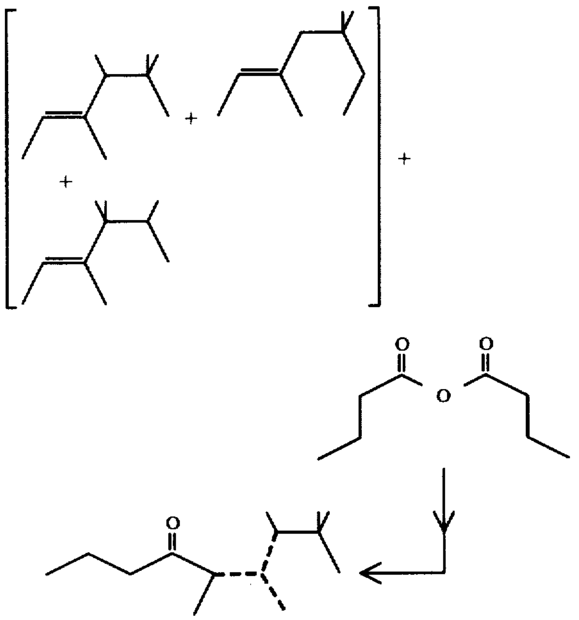

wherein in each of the structures containing dashed lines, these structures represent mixtures of molecules wherein in each of the molecules, one of the dashed lines represents a carbon-carbon double bond and each of the other of the dashed lines represent carbon-carbon single bonds.

Into a 5 liter reaction flask equipped with electric stirrer, thermometer, addition funnel "y" tube, condenser, heating mantle and nitrogen purge accessory are added 55 ml of 70% methane sulfonic acid and 30 g of phosphorous pentoxide. The reaction mass exotherms to 60° C. while maintaining the reaction mass at 65° C. over a period of 10 minutes, 400 ml n-butyric anhydride is added to the reaction mass. Over a period of 40 minutes while maintaining the reaction mass at 84° C., 400 ml of diisoamylene prepared according to the illustration of Example A-1 is added to the reaction mass. The reaction mass is stirred for a period of 4 hours at 84° C.

The reaction mass is then transferred to a 5 gallon open head separatory flask containing 2 liters water. The reaction mass is washed as follows:

A—1 liter 12% aqueous sodium hydroxide

B—1 liter saturated sodium chloride solution

The reaction mass is then distilled on a 12 inch Goodloe Silver Mirror column to yield a mixture of compounds defined according to the generic structure:

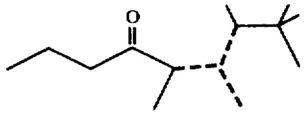

wherein in each of the molecules of the mixture, one of the dashed lines represents carbon-carbon double bond and the other of the dashed lines represent carbon-carbon single bonds. The foregoing is confirmed by GLC, NMR, IR and mass spectral analyses.

The resulting material distills at a vapor temperature of 70°-75° C. and a pressure of 1.0 mm/Hg. The resulting material is utilized as a reactant in the following examples.

EXAMPLE IX

PREPARATION OF PROPYLENE KETAL OF ACETYL DIISOAMYLENE

EXAMPLE IX(A)

Reaction:

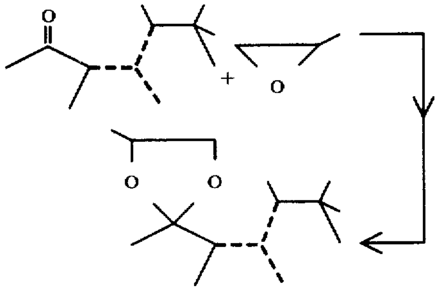

Into a 2000 ml reaction flask equipped with stirrer, heating mantle, addition funnel, reflux condenser, thermometer, cooling bath and nitrogen blanket supply apparatus is added 365 grams (2.0 moles) of acetyl diisoamylene prepared according to Example I (bulked fractions 5-9 resulting from the distillation in the multiplate fractionation column); 300 ml of anhydrous toluene and 24 ml boron trifluoride etherate (0.2 moles). The resulting mixture is heated to 50° C. and while maintaining the reaction mass at 50° C., over a period of 1 hour, 250 ml (3.6 moles) of propylene oxide is added while maintaining the reaction temperature at 79°-89° C.

The reaction mass is then cooled and stirred for another 12 hours while maintaining the temperature at 30° C.

1 liter of 5% aqueous sodium hydroxide is then added to the reaction mass. The reaction mass is transferred to a separatory funnel and the organic layer is washed with two 1 liter saturated sodium chloride portions. The reaction mass is then distilled on a 2" splash column yielding the following fractions:

| Fraction Number | Vapor Temp. °C. | Liquid Temp. °C. | Head Vac. mm. Hg | Reflux Ratio R/D | Weight of Fraction |
|---|---|---|---|---|---|
| 1 | 33/79 | 78/92 | 4.5/2.8 | RO | |

-continued

| Fraction Number | Vapor Temp. °C. | Liquid Temp. °C. | Head Vac. mm. Hg | Reflux Ratio R/D | Weight of Fraction |
|---|---|---|---|---|---|
| 2 | 78 | 89 | 2.0 | RO | |
| 3 | 70 | 88 | 1.6 | RO | |
| 4 | 70 | 88 | 1.6 | RO | |
| 5 | 75 | 100 | 1.6 | RO | 87 |
| 6 | 71 | 117 | 1.6 | RO | 43 |
| 7 | 85 | 137 | 1.6 | RO | 27 |
| 8 | 103 | 163 | 1.1 | RO | 19 |
| 9 | 155 | 205 | 1.1 | RO | |
| 10 | 185 | 230 | 1.1 | RO | |

Fractions 2-7 are bulked and utilized for their organoleptic properties as stated in the following examples.

GLC, NMR, IR and mass spectral analysis yield the information that the resulting product is a mixture of compounds having the structures:

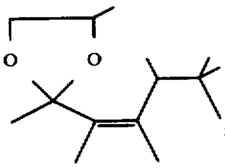
;
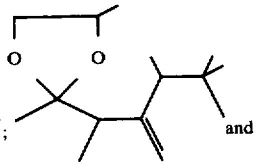
and

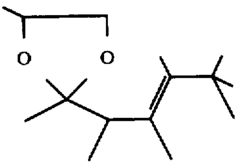

FIG. 15 sets forth the GLC profile for the reaction product produced according to Example IX(A) containing the compounds defined according to the generic structure:

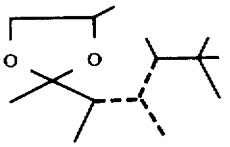

wherein one of the dashed lines in each of the molecules represents a carbon-carbon double bond and the other of the dashed lines in each of the molecules represents a carbon-carbon single bond.

FIG. 16 is the NMR spectrum for the mixture of compounds produced according to Example IX(A) containing the compounds defined according to the generic structure:

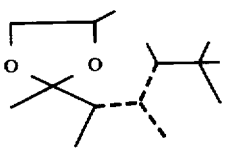

FIG. 17 is the infra-red spectrum for the product produced according to Example IX(A) containing the compounds defined according to the generic structure:

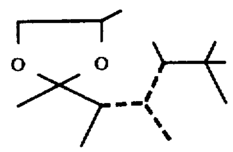

EXAMPLE IX(B)

Reaction:

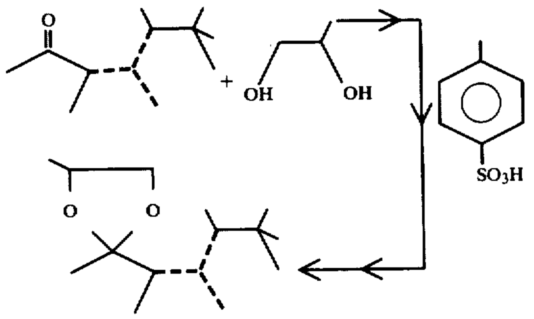

Into a 2000 ml reaction flask equipped with stirrer, heating mantle, addition funnel, reflux condenser, thermometer, cooling bath and nitrogen blanket supply apparatus is added 595 grams (3.0 moles) of acetyl diisoamylene prepared according to Example I (bulked fractions 5–9 of the distillation on the multi-plate fractionation column); 265 ml (3.5 moles) of propylene glycol; 500 ml of anhydrous toluene and 3.0 grams of para-toluene sulfonic acid.

The resulting mixture is heated to reflux in order to azeotrope off the water of reaction. The refluxing is continued for a period of one hour at 125° C. while collecting water of reaction in a Bidwell trap. After a period of 14 hours, 53 ml water is collected and the reaction mass is cooled to room temperature.

The reaction mass is transferred to a separatory funnel and is washed with one 500 ml volume of 10% aqueous sodium hydroxide; and three 500 ml volumes of saturated sodium chloride solution. The solvent is then stripped off on a rotary evaporater and the stripped crude is transferred to a distillation flask whereupon the product is first distilled to yield the following fractions:

| Fraction Number | Vapor Temp. °C. | Liquid Temp. °C. | Head Vac. mm. Hg | Reflux Ratio R/D |
|---|---|---|---|---|
| 1 | 35/75 | 90/87 | 3.8/2.5 | RO |
| 2 | 77 | 87 | 3.5 | RO |
| 3 | 79 | 90 | 3.5 | RO |
| 4 | 81 | 94 | 3.5 | RO |
| 5 | 85 | 98 | 3.5 | RO |
| 6 | 88 | 100 | 3.5 | RO |
| 7 | 90 | 105 | 3.5 | RO |
| 8 | 94 | 200 | 3.5 | RO |

on a 2" splash column. Fractions 5, 6, 7 and 8 are then redistilled on the same 2" splash column to yield the following fractions:

| Fraction Number | Vapor Temp. °C. | Liquid Temp. °C. | Head Vac. mm. Hg | Reflux Ratio R/D | Weight of Fraction |
|---|---|---|---|---|---|
| 1 | 78/70 | 83/85 | 3/3 | | 22 |
| 2 | 82 | 88 | 3 | RO | 22 |
| 3 | 85 | 90 | 3 | RO | 26 |
| 4 | 87 | 91 | 3 | R | 24 |
| 5 | 87 | 91 | 3 | | 42 |
| 6 | 87 | 91 | 3 | | 51 |
| 7 | 94 | 98 | 3 | RO | 46 |
| 8 | 98 | 102 | 3 | RO | 50 |
| 9 | 98 | 102 | 3 | RO | 40 |
| 10 | 95 | 120 | 3 | RO | 16 |
| 11 | 210 | 240 | 3 | RO | 10 |

Fractions 2-10 are bulked and used for their organoleptic properties in the following examples.

FIG. 17(A) represents the GLC profile for the reaction product prior to distillation containing a mixture of compounds having the structure:

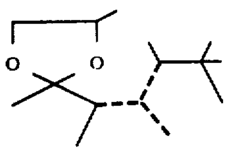

FIG. 17(B) is the GLC profile for Fraction 9 of the distillation product of the reaction product of this example containing a mixture of compounds having the generic structure:

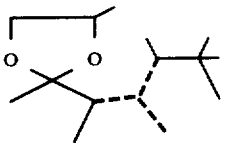

wherein in the mixture one of the dashed lines in each compound represents a carbon-carbon double bond and each of the other of the dashed lines represent carbon-carbon single bonds.

EXAMPLE X

PREPARATION OF ETHYLENE KETAL OF ACETYL DIISOAMYLENE

Reaction:

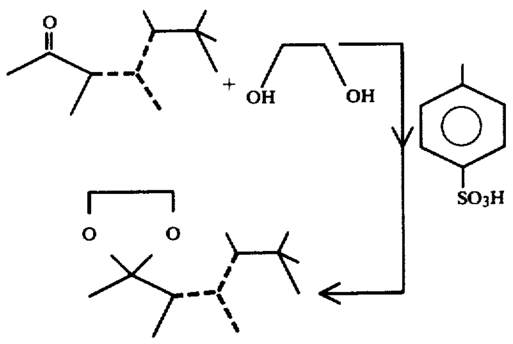

Into a 3 liter reaction flask equipped with heating mantle, stirrer, thermometer, reflux condenser and apparatus for provision of nitrogen blanket is added 1000 ml (4.7 moles) of acetyl diisoamylene produced according to Example I (bulked fractions 5-9 of the last distillation on the multiplate column), 310 grams (5.0 moles) of ethylene glycol; 1000 ml of anhydrous toluene and 0.4 grams of paratoluene sulfonic acid. The resulting mixture is heated to reflux (138° C.) while trapping out water of reaction using a Bidwell trap. The refluxing is continued for a period of 10.5 hours yielding a total of 65 ml water.

The reaction mass is cooled to room temperature and 200 ml of 10% aqueous sodium hydroxide is added to the reaction mass. The reaction mass is stirred and transferred to a separatory funnel. The aqueous layer is separated from the upper organic phase and the upper organic phase is then washed with three 500 ml portions of saturated aqueous sodium chloride solution.

The solvent (toluene) is stripped off of the reaction mass using a rotary evaporator and the crude reaction product is distilled on a 2" splash column yielding the following fractions:

| Fraction Number | Vapor Temp. °C. | Liquid Temp. °C. | Head Vac. mm. Hg | Reflux Ratio R/D | Weight of Fraction |
|---|---|---|---|---|---|
| 1 | 55/67 | 73/73 | 3/3 | RO | 83 |
| 2 | 67 | 73 | 3 | RO | 70 |
| 3 | 67 | 73 | 3 | RO | 89 |
| 4 | 69 | 75 | 3 | RO | 99 |
| 5 | 69 | 75 | 3 | RO | 95 |
| 6 | 75 | 80 | 3 | RO | 66 |

Fractions 2-6 are bulked and utilized for their organoleptic properties in examples set forth infra.

GLC, NMR, IR and mass spectral analyses yield the information that the resulting product is a mixture of compounds defined according to the generic structure:

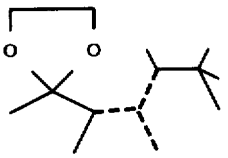

wherein in each of the molecules of the mixture, one of the dashed lines is a carbon-carbon double bond and the other of the dashed lines is a carbon-carbon single bond. Each of the constituents of this reaction mass may be trapped out using preparative GLC to yield the following compounds:

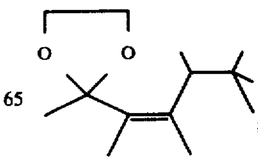
;
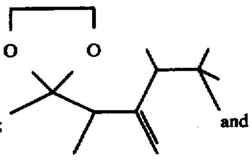
and

-continued

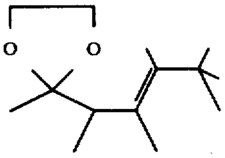

FIG. 18 is the GLC profile for the reaction product of Example X.

EXAMPLE XI

The dioxolanes produced according to Example IX(A), IX(B) and X have very lone-lasting cedary, ambery, woody, sweet and patchouli-like aroma nuances which may be utilized to a great extent in inexpensive, functional products. The following pine fragrance demonstrates the use of these materials in perfume compositions. In each of the cases the ketals of Examples IX(A), IX(B) and X are used in an amount of 47.9%.

| | Parts by Weight Example | |
|---|---|---|
| Ingredients | XIA | XIB |
| Isobornyl acetate | 100 | 100 |
| Camphor | 10 | 10 |
| Terpineol | 25 | 25 |
| Fir Balsam Absolute (50% in Diethyl Phthalate) | 20 | 20 |
| Coumarin | 4 | 4 |
| Linalool | 30 | 30 |
| Anethol | 2 | 2 |
| Fenchyl Alcohol | 10 | 10 |
| Lemon Terpenes Washed | 50 | 50 |
| Borneol | 5 | 5 |
| Galbanum Oil | 5 | 5 |
| Turpentine Russian | 150 | 150 |
| Pinus Pumilionus | 50 | 50 |
| Eucalyptol | 50 | 50 |
| 2,2,6-trimethyl-1-cyclohexene-1-carboxaldehyde | 5 | 5 |
| Maltol 1% in Diethyl Phthalate | 5 | 5 |
| Product produced according to either Example IX(A) or IX(B), a mixture of products defined by the structure: 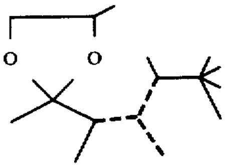 wherein in each of the molecules in the mixture one of the dashed lines represents a carbon-carbon double bond and each of the other of the dashed lines represent carbon-carbon single bonds (in Example IX(A) bulked fractions 2-7 and in Example IX(B) bulked fractions 2-10). | 479 | 0 |
| Product produced according to either Example IX(A) or IX(B), a mixture of products defined by the structure: 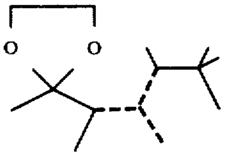 wherein in each of the molecules in the mixture one of the dashed lines represents a carbon-carbon double bond and each of the other of the dashed lines represent carbon-carbon single bonds (in Example IX(A) bulked fractions 2-7 and in Example IX(B) bulked fractions 2-10). | 0 | 479 |

EXAMPLE XII

PREPARATION OF A COSMETIC POWDER PREPARATION

A cosmetic powder is prepared by mixing in a ball mill, 100 grams of the 2,4-dimethyl-2-(1,2,3,4,4-pentamethyl)-pentenyl-1,3-dioxolane isomer mix prepared according to either Example IX(A) or IX(B) (in Example IX(A) bulked fractions 2-7 and in Example IX(B) bulked fractions 2-10). The resulting cosmetic powder has a pleasant cedary, ambery, woody, sweet, patchouli aroma.

EXAMPLE XIII

PERFUMED LIQUID DETERGENT

Concentrated liquid detergents (Lysine salt of n-dodecylbenzene sulfonic acid as more specifically described in U.S. Pat. No. 3,948,818 issued on Apr. 6, 1976) with a pleasant cedar, amber, woody, sweet and patchouli aroma profile are prepared containing 0.10%, 0.15%, 0.20%, 0.25%, 0.30% and 0.35% of 2,4-dimethyl-2-(1,2,3,4,4-pentamethyl)-pentenyl-1,3-dioxolane isomer mix prepared according to either Example IX(A) or IX(B). They are prepared by adding and homogeneously mixing the appropriate quantity of the mixture prepared according to either Example IX(A) or IX(B) (in Example IX(A) bulked fractions 2-7 and in Example IX(B) bulked fractions 2-10) in the liquid detergent. The detergents all possess excellent intense pleasant cedary, ambery, woody, sweet and patchouli aroma profiles, the intensity increasing with greater concentrations of the dioxolane isomer mixture prepared according to either Example IX(A) or IX(B).

EXAMPLE XIV

PREPARATION OF A COLOGNE AND HANDKERCHIEF PERFUME

The 2,4-dimethyl-2-(1,2,3,4,4-pentamethyl)-pentenyl-1,3-dioxolane isomer mixture prepared according to either Example IX(A) or IX(B) (in Example IX(A) bulked fractions 2-7 and in Example IX(B) bulked fractions 2-10) is incorporated into colognes at concentrations of 2.0%, 2.5%, 3.0%, 3.5%, 4.0%, 4.5% and 5.0% in 75%, 80%, 85% and 90% aqueous food grade ethanol; and into handkerchief perfumes at concentrations of 15%, 20%, 25% and 30% in 80%, 85%, 90% and 95% aqueous food grade ethanol solutions. Distinctive and definitive long-lasting cedary, ambery, woody, sweet and patchouli aroma profiles are imparted to the cologne and to the handkerchief perfume compositions at all levels indicated.

EXAMPLE XV

PREPARATION OF SOAP COMPOSITION

One hundred grams of soap chips (IVORY®, produced by the Procter & Gamble Company, Cincinnati, Ohio) are admixed with 1 gram of the 2,4-dimethyl-2-(1,2,3,4,4-pentamethyl)-pentenyl-1,3-dioxolane mixture produced according to Example IX(A) or IX(B) (in Example IX(A) bulked fractions 2-7 and in Example IX(B) bulked fractions 2-10) until a homogeneous composition is obtained. The homogeneous composition is then heated under 3 atmospheres pressure at 180° C. for a period of 3 hours and the resulting liquid is placed in a soap mold. The resulting soap cake, on cooling, manifests an excellent long-lasting pleasant cedary, ambery, woody, sweet and patchouli aroma.

EXAMPLE XVI

PREPARATION OF A SOLID DETERGENT COMPOSITION

Detergents are prepared from the following ingredients according to Example I of Canadian Pat. No. 1,007,948:

| Ingredient | Percent by Weight |
|---|---|
| Neodol® 45-11 (a $C_{14}$-$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is a phosphate-free detergent. A total of 100 grams of said detergent is admixed with 0.10, 0.15, 0.20 and 0.25 grams of the 2,4-dimethyl-2-(1,2,3,4,4-pentamethyl)-pentenyl-1,3-dioxolane isomer mix prepared according to either Example IX(A) or IX(B) (in Example IX(A) bulked fractions 2-7 and in Example IX(B) bulked fractions 2-10). Each of the detergent samples has an excellent pleasant, cedary, ambery, woody, sweet and patchouli aroma profile.

EXAMPLE XVII

DRYER-ADDED FABRIC SOFTENER ARTICLE

Utilizing the procedure of Example I at column 15 of U.S. Pat. No. 3,632,396, a non-woven cloth substrate useful as a dryer-added fabric softening article of manufacture prepared wherein the substrate, the substrate coating and the outer coating and the perfuming material are as follows:

1. a water "dissolvable" paper ("Dissolvo Paper")
2. Adogen 448 (m.p. about 140° F.) as the substrate coating; and
3. An outer coating having the following formulation (m.p. about 150° F.):

57% $C_{20-22}$ HAPS
22% isopropyl alcohol
20% antistatic agent
1% of the 2,4-dimethyl-2-(1,2,3,4,4-pentamethyl)-pentenyl-1,3-dioxolane isomer mix prepared according to either Example IX(A) or IX(B) (in Example IX(A) bulked fractions 2-7 and in Example IX(B) bulked fractions 2-10).

Fabric softening compositions containing the dioxolane mixture prepared according to either Example IX(A) or IX(B) (in Example IX(A) bulked fractions 2-7 and in Example IX(B) bulked fractions 2-10) consist essentially of a substrate having a weight of about 3 grams per 100 square inches of substrate coating, of about 1.85 grams per 100 square inches of substrate, and an outer coating of about 1.4 grams per 100 square inches of substrate, thereby providing a totally aromatized substrate and outer coating weight ratio of about 1:1 by weight of the substrate. A pleasant cedary, ambery, woody, sweet and patchouli faint aroma profile is imparted to the head space in the dryer on operation thereof using the said drier-added fabric softening non-woven fabric.

In the following examples, Aromox® DMC-W and Aromox® DMMC-W are 30% aqueous solutions of dimethyl cocoamine oxide; and Aromox® NCMDW is a 40% aqueous solution of N-cocomorpholine oxide produced by Armac Division of AKZO of Chicago, Ill.

EXAMPLE XVIII

Four drops of the 2,4-dimethyl-2-(1,2,3,4,4-pentamethyl)-pentenyl-1,3-dioxolane isomer mix prepared according to either Example IX(A) or IX(B) (in Example IX(A) bulked fractions 2-7 and in Example IX(B) bulked fractions 2-10) is added to 2 grams of Aromox® DMC-W to produce a clear premix. The clear premix is added to 200 grams of Clorox® with stirring resulting in a clear stable single phase solution. Sufficient 1 M aqueous NaOH is added to bring the pH of the mixture up to 12.8. The solution remains substantially stable at 120° F. for a period of seven days. When the 5% aqueous sodium hypochlorite solution is used as a laundry bleach, the resulting laundry on dry-out in an atmosphere of 65% relative humidity yields substantially no characteristic "hypochlorite" odor but does have a faint, pleasant, cedar, amber, woody, sweet and patchouli aroma. Furthermore, no such characteristic "hypochlorite" aroma is retained on the hands of the individual handling such laundry in both the wet and the dry states.

EXAMPLE XIX

Aromox® DMMC-W in various quantities is mixed with 0.1 gram of the 2,4-dimethyl-2-(1,2,3,4,4-pentamethyl-1-pentenyl)-1,3-dioxolane isomer mix prepared according to either Example IX(A) or IX(B) (in Example IX(A) bulked fractions 2-7 and in Example IX(B) bulked fractions 2-10). The resulting premixes are then added to 200 grams of an aqueous 5% sodium hypochlorite solution. Sufficient 12.5 M aqueous NaOH is added to bring the pH of the mixture up to 13. The following results are obtained:

| Percentage Aromox® DMMC-W | Clarity of hypochlorite solution after addition of premix |
|---|---|
| 0.23% | Clear after three days |
| 0.15% | Clear after three days |
| 0.08% | Initially slightly turbid; two phases exist after three days |

When the 5% sodium hypochlorite solutions are used as laundry bleaches, the resulting laundry batches on dry-out in an atmosphere of 65% relative humidity yield substantially no characteristic "hypochlorite" odor but do have faint, pleasant, cedary, amber, woody, sweet, and patchouli aroma profiles. Furthermore, no such characteristic "hypochlorite" aromas are retained on the hands of the individuals handling the laundry batches in both the wet and the dry states.

EXAMPLE XX

Two grams of Aromox® DMMC-W is admixed with eight drops of the 2,4-dimethyl-2-(1,2,3,4,4-pentamethyl-1-pentenyl)-1,3-dioxolane isomer mix produced according to either Example IX(A) or IX(B) (in Example IX(A) bulked fractions 2-7 and in Example IX(B) bulked fractions 2-10). The premix is then added with stirring to 200 grams of a 7% aqueous solution of lithium hypochlorite. Sufficient 3 M aqueous LiOH is added to bring the pH of the solution of 13.4. The mixture is then heated to 120° F. and maintained at that temperature with stirring for a period of 1 week. The resulting solution remains clear in a single phase. When used as a laundry bleach, the resulting bleached laundry on dry-out in an atmosphere of 50% relative humidity retains a "clean fresh" pleasant, cedary, amber, woody, sweet, patchouli aroma profile; whereas without the use of the 1,3-dioxolane derivative prepared according to Example IX, the bleached laundry has a faint, characteristic disagreeable "hypochlorite" aroma.

EXAMPLE XXI

Two grams of Aromox® DMMC-W is admixed with eight drops of the 2,4-dimethyl-2-(1,2,3,4,4-pentamethyl-1-pentenyl)-1,3-dioxolane isomer mix prepared according to either Example IX(A) or IX(B) (in Example IX(A) bulked fractions 2-7 and in Example IX(B) bulked fractions 2-10). This premix is then added, with stirring, to 200 grams of a mixture containing 4.5% aqueous sodium hypochlorite and 4.5% aqueous lithium hypochlorite. Sufficient 4 M aqueous LiOH is added to bring the pH of the solution to 13.4. The mixture is then heated to 120° F. and maintained at that temperature for a period of one week. The resulting solution remains clear in a single phase. When used as a laundry bleach, the resulting bleached laundry on dry-out in an atmosphere of 50% relative humidity retains a "clean fresh", pleasant, cedary, amber, woody, sweet and patchouli aroma profile whereas without the use of the 1,3-dioxolane derivative prepared according to Example IX(A) or IX(B), the bleached laundry has a faint characteristic disagreeable "hypochlorite" aroma.

EXAMPLE XXII

Two grams of Aromox® DMMC-W is admixed with eight drops of 2,4-dimethyl-2-(1,2,3,4,4-pentamethyl-1-pentenyl)-1,3-dioxolane isomer mix prepared according to either Example IX(A) or IX(B) (in Example IX(A) bulked fractions 2-7 and in Example IX(B) bulked fractions 2-10). This premix is then added with stirring to 200 grams of a mixture containing 4.5% aqueous sodium hypochlorite and 4.5% aqueous lithium hypochlorite. Sufficient 2 M aqueous NaOH is added to bring the pH of the solution to 13.4. The mixture is then heated to 110° F. and maintained at that temperature with stirring for a period of 2 weeks. The resulting solution remains clear as a single phase when used as a laundry bleach. The resulting bleached laundry, on dry-out in an atmosphere of 50% relative humidity retains a pleasant, cedar, amber, woody, sweet and patchouli aroma profile whereas without the use of the 1,3-dioxolane composition prepared according to either Example IX(A) or IX(B), the bleached laundry has a faint characteristic disagreeable "hypochlorite" aroma.

EXAMPLE XXIII

Four drops of a 50:50 mixture containing 50 weight percent of 2,4-dimethyl-2-(1,2,3,4,4-pentamethyl-1-pentenyl)-1,3-dioxolane isomer mixture prepared according to either Example IX(A) or IX(B) (in Example IX(A) bulked fractions 2-7 and in Example IX(B) bulked fractions 2-10) and 50% of acetyl diisoamylene prepared according to Example I is added to 1.5 grams of Aromox® NCMDW to produce a clear premix. The clear premix is added to 200 grams of Clorox® with stirring resulting in a clear, stable, single phase solution. Sufficient 1 M aqueous NaOH is added to bring the pH of the mixture up to 12.8. The solution remains substantially stable at 120° F. for a period of 7 days. When the 5% aqueous sodium hypochlorite solution is used as a laundry bleach, the resulting laundry on dry-out in an atmosphere of 65% relative humidity yields substantially no characteristic "hypochlorite" odor but does have a faint, pleasant, cedar, amber, woody, sweet, patchouli aroma profile. Furthermore, no such characteristic "hypochlorite" aroma is retained on the hands of the individual handling such laundry in both the wet and the dry states.

EXAMPLE XXIV

Four drops of the dioxolane prepared according to Example X (bulked distillation fractions 2-6) is added to 1 gram of n-undecyl dimethyl amine oxide to produce a clear premix. The clear premix is added to 200 grams of CLOROX® with stirring resulting in a clear stable single phase solution. Sufficient 1 M aqueous NaOH is added to bring the pH of the mixture up to 12.8. The solution remains substantially stable at 120° F. for a period of seven days. When the 5% aqueous sodium hypochlorite solution is used as a laundry bleach, the resulting laundry on dry-out in an atmosphere of 65% relative humidity yields substantially no characteristic "hypochlorite" aroma but does have a faint, pleasant, cedar-like, amber, patchouli-like aroma. Furthermore, no such characteristic "hypochlorite" aroma is retained on the hands of the individual handling such laundry in both the wet and the dry states.

EXAMPLE XXV

Four drops of a 50:50 mixture of the dioxolane of either Example IX(A) or IX(B) (in Example IX(A) bulked fractions 2-7 and in Example IX(B) bulked fractions 2-10) and the dioxolane of Example X (bulked distillation fractions 2-6) is added to 1 gram of n-dodecyl dimethyl amine oxide to produce a clear premix. The clear premix is added to 200 grams of Clorox® with stirring resulting in a clear, stable, single phase solution. Sufficient 1 M aqueous NaOH is added to bring the pH of the mixture up to 12.8. The solution remains substantially stable at 120° F. for a period of 7 days. When the 5% aqueous sodium hypochlorite solution is used as a laundry bleach, the resulting laundry on dry-out in an atmosphere of 65% relative humidity yields substantially no characteristic "hypochlorite" odor but does have a very warm, pleasant, cedar, amber, woody, vetiver-like, sweet and patchouli aroma.

Furthermore, no such characteristic "hypochlorite" aroma is retained on the hands of the individual handling such laundry in both the wet and the dry states.

EXAMPLE XXVI

One gram of the dioxolane of Example X (bulked distillation fractions 2-6) is intimately admixed with 1 gram of n-tridecyl dimethylamine oxide. This premix is then added with stirring to 200 grams of a 7% aqueous solution of lithium hypochlorite. Sufficient 3 M aqueous LiOH is added to bring the pH of the solution to 13.4. The mixture is then heated to 120° F. and maintained at that temperature with stirring for a period of one week. The resulting solution remains clear in a single phase. When used as a laundry bleach, the resulting bleached laundry on dry-out in an atmosphere of 50% relative humidity retains a clean, fresh, cedar, amber, woody, sweet, patchouli-like aroma whereas without the use of the dioxolane composition mixture of Example X and either Example IX(A) or IX(B) (in Example IX(A) bulked fractions 2-7 and in Example IX(B) bulked fractions 2-10), the bleached laundry has a faint characteristic disagreeable "hypochlorite" aroma.

EXAMPLE XXVII

FLAVOR COMPOSITION

The following basic walnut flavor formulation is prepared:

| Ingredients | Parts by Weight |
|---|---|
| Ethyl-2-methyl butyrate | 10 |
| Vanillin | 40 |
| Butyl valerate | 40 |
| 2,3-Diethyl pyrazine | 5 |
| Methyl cyclopentenolone | 80 |
| Benzaldehyde | 60 |
| Valerian oil Indian (1% in 95% aqueous ethanol alcohol) | 0.5 |
| Propylene glycol | 764.5 |

The 1,3-dioxolane derivative isomer mixture prepared according to either Example IX(A) or IX(B) (in Example IX(A) bulked fractions 2-7 and in Example IX(B) bulked fractions 2-10) is added to the above formulation at the rate of 1.5%. This formulation is compared to a formulation which does not have such 1,3-dioxolane derivative mixture added to it at the rate of 20 ppm in water. The formulation containing the 1,3-dioxolane derivative mixture has a "woody, balsamic", fresh, walnut kernel and walnut skin-like taste and, in addition, has a fuller mouth feel and longer lasting taste. The flavor that has added to it the 1,3-dioxolane isomer mixture prepared according to either Example IX(A) or IX(B) is preferred by a group of flavor panelists and they consider it to be a substantially improved walnut flavor.

EXAMPLE XXVIII

BEVERAGE

The addition of the 1,3-dioxolane derivative isomer mixture prepared according to the process of Example X (bulked distillation fractions 2-6) is added at the rate of 0.3 ppm to a commercial cola beverage giving the beverage a fuller "woody, balsamic" long-lasting taste. The dioxolane derivative mixture adds to the pleasant top-notes of the beverage. When comparing the cola beverage containing the 1,3-dioxolane isomer mixture to one having the same formula but not containing the dioxolane derivative isomer mixture, a five member bench panel prefers the beverage containing the 1,3-dioxolane isomer mixture.

EXAMPLE XXIX

TOBACCO FLAVOR FORMULATION

Cigarettes are produced using the following tobacco formulation:

| Ingredients | Parts by Weight |
|---|---|
| Bright | 40.1 |
| Burley | 24.9 |
| Maryland | 1.1 |
| Turkish | 11.6 |
| Stem (flue-cured) | 14.2 |
| Glycerine | 2.8 |
| $H_2O$ | 5.3 |

At the rate of 0.2%, the following tobacco flavor formulation is applied to all of the cigarettes produced with the above tobacco formulation.

| Ingredients | Parts by Weight |
|---|---|
| Ethyl butyrate | .05 |
| Ethyl valerate | .05 |
| Maltol | 2.00 |
| Cocoa Extract | 26.00 |
| Coffee Extract | 10.00 |
| Ethyl alcohol (95%) | 20.00 |
| $H_2O$ | 41.90 |

To 50% of the cigarettes, 10 and 20 ppm of the 1,3-dioxolane derivative isomer mixture prepared according to either Example IX(A) or IX(B) (in Example IX(A) bulked fractions 207 and in Example IX(B) bulked fractions 2-10) are added. These cigarettes are hereinafter called "experimental" cigarettes and the cigarettes without the 1,3-dioxolane derivative isomer mixture are hereinafter called "control" cigarettes. The control and experimental cigarettes are then evaluated by paired comparison and the results are as follows:

a. In aroma, the experimental cigarettes are found to be more aromatic.

b. In smoke flavor, the experimental cigarettes are found to be more aromatic, more sweet, more bitter, more green, richer and slightly less harsh in the mouth and more cigarette tobacco-like than the control cigarettes.

The experimental cigarettes containing 20 ppm of the 1,3-dioxolane derivative isomer mixture prepared according to either Example IX(A) or IX(B) are found to be woody, slightly chemical and mouth-coating in the smoke flavor. All cigarettes, both control and experimental, are evaluated for smoke flavor with a 20 mm cellulose acetate filter. The dioxolane derivative prepared according to either Example IX(A) or IX(B) enhances the tobacco-like taste of the blended cigarette. When the dioxolane derivative of either Example IX(A) or IX(B) is replaced by the dioxolane derivative prepared according to Example X, (bulked distillation fractions 2-6), closely similar results are obtained.

What is claimed is:

1. A process for augmenting or enhancing the aroma of a perfume composition or a cologne comprising the ste of adding to a perfume base or a cologne base an aroma augmenting or enhancing quantity of at least one dioxolane, oxathiolane or dithiolane compound defined according to the structure:

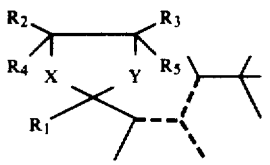

wherein $R_1$ represents $C_1$–$C_4$ lower alkyl; $R_2$, $R_3$, $R_4$ and $R_5$ represent hydrogen or $C_1$–$C_3$ lower alkyl; X and Y are the same or different and each represents oxygen or sulfur and wherein one of the dashed lines represents a carbon-carbon double bond and each of the other of the dashed lines represent carbon-carbon single bonds.

2. The process of claim 1 wherein the compound added has the structure:

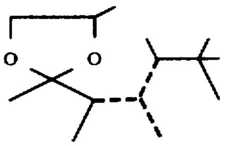

3. The process of claim 1 wherein the compound added to the perfume base or the cologne has the structure:

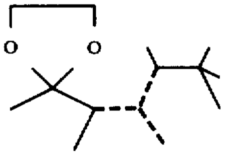

4. A process for augmenting or enhancing the aroma of a perfume as defined according to claim 1 wherein there is added to a perfume an aroma augmenting or enhancing quantity of a composition of matter comprising a major proportion of compounds defined according to a structure selected from the group consisting of:

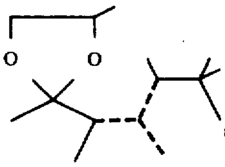

and

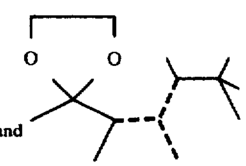

wherein in the mixture in each of the molecules one of the dashed lines represents a carbon-carbon double bond and each of the other of the dashed lines represent carbon-carbon single bonds, said composition of matter produced according to the process comprising the steps of:

(a) dimerization of isoamylene having the structure:

in the presence of an acid catalyst to form a mixture containing a major proportion of a mixture of compounds defined according to the structure:

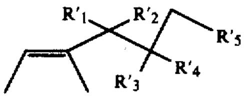

wherein (i) at least one of $R_3'$ and $R_4'$ represents methyl; (ii) the sum of the carbon atoms in $R_1'$, $R_2'$, $R_3'$, $R_4'$ and $R_5'$ is 3; and (iii) $R_1'$ and $R_2'$ represent hydrogen when $R_5'$ is methyl;

(b) reacting the resulting diisoamylene mixture with a compound selected from the group consisting of an alkanoyl halide having 2 or 3 carbon atoms and an alkanoic acid anhydride having 4 to 6 carbon atoms to form a mixture containing a major proportion of compounds defined according to the structure:

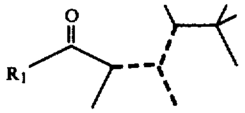

wherein $R_1$ is $C_1$ or $C_2$ alkyl and wherein in the mixtures in each of the molecules one of the dashed lines represents a carbon-carbon double bond and the other of the dashed lines represent carbon-carbon single bonds; and (c) reacting the resulting mixture with a compound selected from the group consisting of 1,2-propylene glycol; 1,2-propylene oxide; 1,2-ethylene glycol; and 1,2-ethylene oxide at a temperature of between 0° C. and 80° C. in the presence of a Lewis acid catalyst.

5. The process of claim 4 wherein in the process to produce the composition of matter, the reaction between the alkanoyl halide or the alkanoic acid anhydride with the diisoamylene mixture is carried out in the presence of a Lewis acid or a mineral acid at a temperature of between 0° C. and 50° C. with the mole ratio of diisoamylene mixture: acylating agent being between 1:1.1 and 2:1.0 and the concentration of catalyst being between 5 and 10% by weight of the reaction mass.

* * * * *